(12) United States Patent
Hastings

(10) Patent No.: US 9,326,751 B2
(45) Date of Patent: May 3, 2016

(54) CATHETER GUIDANCE OF EXTERNAL ENERGY FOR RENAL DENERVATION

(75) Inventor: Roger Hastings, Maple Grove, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 148 days.

(21) Appl. No.: 13/295,182

(22) Filed: Nov. 14, 2011

(65) Prior Publication Data

US 2012/0123243 A1 May 17, 2012

Related U.S. Application Data

(60) Provisional application No. 61/414,735, filed on Nov. 17, 2010.

(51) Int. Cl.
*A61B 5/05* (2006.01)
*A61B 8/12* (2006.01)
(Continued)

(52) U.S. Cl.
CPC .............. *A61B 8/12* (2013.01); *A61B 8/0841* (2013.01); *A61B 8/4488* (2013.01); *A61B 17/2202* (2013.01); *A61B 19/5244* (2013.01); *A61N 7/02* (2013.01); *A61B 8/445* (2013.01); *A61B 2017/00106* (2013.01); *A61B 2018/00404* (2013.01); *A61B 2018/00434* (2013.01); *A61B 2018/00511* (2013.01); *A61B 2019/5251* (2013.01); *A61B 2019/5263* (2013.01); *A61B 2019/5276* (2013.01); *A61B 2019/5285* (2013.01); *A61B 2019/5429* (2013.01); *A61B 2019/5458* (2013.01);
(Continued)

(58) Field of Classification Search
CPC ................ A61B 2019/5458; A61B 2019/5263

USPC .................................. 600/411, 421, 424, 427
See application file for complete search history.

(56) References Cited

U.S. PATENT DOCUMENTS

| 164,184 A | 6/1875 | Kiddee |
|---|---|---|
| 1,167,014 A | 1/1916 | O'Brien |

(Continued)

FOREIGN PATENT DOCUMENTS

| DE | 10038737 A1 | 2/2002 |
|---|---|---|
| EP | 1053720 A1 | 11/2000 |

(Continued)

OTHER PUBLICATIONS

Baun, Principles of General & Vascular Sonography, Chapter 2, "Interaction with Soft Tissue", pp. 23-34.
(Continued)

*Primary Examiner* — Long V Le
*Assistant Examiner* — Ellsworth Weatherby
(74) *Attorney, Agent, or Firm* — Kacvinsky Daisak Bluni PLLC

(57) ABSTRACT

An in vivo apparatus includes a flexible shaft having a proximal end, a distal end, and a length sufficient to access a patient's renal artery relative to a percutaneous access location. An energy guide apparatus is provided at the distal end of the shaft and dimensioned for deployment within the renal artery. An ex vivo apparatus includes an arrangement configured to localize the energy guide apparatus within the renal artery, and an energy source configured to direct ablative energy to target tissue located a predetermined distance from the localized energy guide apparatus. The target tissue includes perivascular renal nerve tissue adjacent the renal artery.

1 Claim, 13 Drawing Sheets

(51) Int. Cl.

| | | |
|---|---|---|
| *A61B 8/08* | (2006.01) | |
| *A61B 8/00* | (2006.01) | |
| *A61B 17/22* | (2006.01) | |
| *A61B 19/00* | (2006.01) | |
| *A61N 7/02* | (2006.01) | |
| *A61B 17/00* | (2006.01) | |
| *A61B 18/00* | (2006.01) | |
| *A61N 5/10* | (2006.01) | |
| *A61N 7/00* | (2006.01) | |

(52) U.S. Cl.
CPC ...... *A61B 2019/5466* (2013.01); *A61N 2005/1051* (2013.01); *A61N 2005/1058* (2013.01); *A61N 2007/003* (2013.01); *A61N 2007/0052* (2013.01)

(56) References Cited

U.S. PATENT DOCUMENTS

| | | | |
|---|---|---|---|
| 2,505,358 A | 4/1950 | Gusberg et al. | |
| 2,701,559 A | 2/1955 | Cooper | |
| 3,108,593 A | 10/1963 | Glassman | |
| 3,108,594 A | 10/1963 | Glassman | |
| 3,540,431 A | 11/1970 | Mobin | |
| 3,952,747 A | 4/1976 | Kimmell | |
| 3,996,938 A | 12/1976 | Clark, III | |
| 4,046,150 A | 9/1977 | Schwartz et al. | |
| 4,290,427 A | 9/1981 | Chin | |
| 4,402,686 A | 9/1983 | Medel | |
| 4,483,341 A | 11/1984 | Witteles et al. | |
| 4,574,804 A | 3/1986 | Kurwa | |
| 4,587,975 A | 5/1986 | Salo et al. | |
| 4,649,936 A | 3/1987 | Ungar et al. | |
| 4,682,596 A | 7/1987 | Bales et al. | |
| 4,709,698 A | 12/1987 | Johnston et al. | |
| 4,765,331 A | 8/1988 | Petruzzi et al. | |
| 4,770,653 A | 9/1988 | Shturman | |
| 4,784,162 A | 11/1988 | Ricks et al. | |
| 4,785,806 A | 11/1988 | Deckelbaum et al. | |
| 4,790,310 A | 12/1988 | Ginsburg et al. | |
| 4,799,479 A | 1/1989 | Spears | |
| 4,823,791 A | 4/1989 | D'Amelio et al. | |
| 4,830,003 A | 5/1989 | Wolff et al. | |
| 4,849,484 A | 7/1989 | Heard | |
| 4,862,886 A | 9/1989 | Clarke et al. | |
| 4,887,605 A | 12/1989 | Angelsen et al. | |
| 4,784,132 B1 | 3/1990 | Fox et al. | |
| 4,920,979 A | 5/1990 | Bullara et al. | |
| 4,938,766 A | 7/1990 | Jarvik | |
| 4,955,377 A | 9/1990 | Lennox et al. | |
| 4,976,711 A | 12/1990 | Parins et al. | |
| 5,034,010 A | 7/1991 | Kittrell et al. | |
| 5,052,402 A | 10/1991 | Bencini et al. | |
| 5,053,033 A | 10/1991 | Clarke et al. | |
| 5,071,424 A | 12/1991 | Reger et al. | |
| 5,074,871 A | 12/1991 | Groshong et al. | |
| 5,098,429 A | 3/1992 | Sterzer et al. | |
| 5,098,431 A | 3/1992 | Rydell | |
| 5,109,859 A | 5/1992 | Jenkins | |
| 5,125,928 A | 6/1992 | Parins et al. | |
| 5,129,396 A | 7/1992 | Rosen et al. | |
| 5,139,496 A | 8/1992 | Hed | |
| 5,143,836 A | 9/1992 | Hartman et al. | |
| 5,156,610 A | 10/1992 | Reger et al. | |
| 5,158,564 A | 10/1992 | Schnepp-Pesch | |
| 5,170,802 A | 12/1992 | Mehra | |
| 5,178,620 A | 1/1993 | Eggers et al. | |
| 5,178,625 A | 1/1993 | Groshong et al. | |
| 5,190,540 A | 3/1993 | Lee | |
| 5,211,651 A | 5/1993 | Reger et al. | |
| 5,234,407 A | 8/1993 | Teirstein et al. | |
| 5,240,003 A * | 8/1993 | Lancee et al. | 600/467 |
| 5,242,441 A | 9/1993 | Avitall | |
| 5,251,634 A | 10/1993 | Weinberg et al. | |
| 5,255,679 A | 10/1993 | Imran | |
| 5,263,493 A | 11/1993 | Avitall | |
| 5,267,954 A | 12/1993 | Nita et al. | |
| 5,277,201 A | 1/1994 | Stern et al. | |
| 5,282,484 A | 2/1994 | Reger et al. | |
| 5,286,254 A | 2/1994 | Shapland et al. | |
| 5,295,484 A | 3/1994 | Marcus | |
| 5,297,564 A | 3/1994 | Love et al. | |
| 5,300,068 A | 4/1994 | Rosar et al. | |
| 5,301,683 A | 4/1994 | Durkan | |
| 5,304,115 A | 4/1994 | Pflueger et al. | |
| 5,304,121 A | 4/1994 | Sahatjian | |
| 5,304,171 A | 4/1994 | Gregory et al. | |
| 5,304,173 A | 4/1994 | Kittrell et al. | |
| 5,306,250 A | 4/1994 | March et al. | |
| 5,312,328 A | 5/1994 | Nita et al. | |
| 5,314,466 A | 5/1994 | Stern et al. | |
| 5,322,064 A | 6/1994 | Lundquist | |
| 5,324,255 A | 6/1994 | Passafaro et al. | |
| 5,326,341 A | 7/1994 | Lew et al. | |
| 5,326,342 A | 7/1994 | Pflueger et al. | |
| 5,330,518 A | 7/1994 | Neilson et al. | |
| 5,333,614 A | 8/1994 | Feiring | |
| 5,342,292 A | 8/1994 | Nita et al. | |
| 5,344,395 A | 9/1994 | Whalen et al. | |
| 5,364,392 A | 11/1994 | Warner et al. | |
| 5,365,172 A | 11/1994 | Hrovat et al. | |
| 5,368,557 A | 11/1994 | Nita et al. | |
| 5,368,558 A | 11/1994 | Nita et al. | |
| 5,380,274 A | 1/1995 | Nita et al. | |
| 5,380,319 A | 1/1995 | Saito et al. | |
| 5,382,228 A | 1/1995 | Nita et al. | |
| 5,383,874 A | 1/1995 | Jackson et al. | |
| 5,383,917 A | 1/1995 | Desai et al. | |
| 5,397,301 A | 3/1995 | Pflueger et al. | |
| 5,397,339 A | 3/1995 | Desai | |
| 5,401,272 A | 3/1995 | Perkins et al. | |
| 5,403,311 A | 4/1995 | Abele et al. | |
| 5,405,318 A | 4/1995 | Nita et al. | |
| 5,405,346 A | 4/1995 | Grundy et al. | |
| 5,409,000 A | 4/1995 | Imran | |
| 5,417,672 A | 5/1995 | Nita et al. | |
| 5,419,767 A | 5/1995 | Eggers et al. | |
| 5,427,118 A | 6/1995 | Nita et al. | |
| 5,432,876 A | 7/1995 | Appeldorn et al. | |
| 5,441,498 A | 8/1995 | Perkins et al. | |
| 5,447,509 A | 9/1995 | Mills et al. | |
| 5,451,207 A | 9/1995 | Yock et al. | |
| 5,453,091 A | 9/1995 | Taylor et al. | |
| 5,454,788 A | 10/1995 | Walker et al. | |
| 5,454,809 A | 10/1995 | Janssen | |
| 5,455,029 A | 10/1995 | Hartman et al. | |
| 5,456,682 A | 10/1995 | Edwards et al. | |
| 5,457,042 A | 10/1995 | Hartman et al. | |
| 5,471,982 A | 12/1995 | Edwards et al. | |
| 5,474,530 A | 12/1995 | Passafaro et al. | |
| 5,478,351 A | 12/1995 | Meade et al. | |
| 5,496,311 A | 3/1996 | Abele et al. | |
| 5,496,312 A | 3/1996 | Klicek et al. | |
| 5,498,261 A | 3/1996 | Strul | |
| 5,505,201 A | 4/1996 | Grill et al. | |
| 5,505,730 A | 4/1996 | Edwards | |
| 5,507,744 A | 4/1996 | Tay et al. | |
| 5,522,873 A | 6/1996 | Jackman et al. | |
| 5,531,520 A | 7/1996 | Grimson et al. | |
| 5,540,656 A | 7/1996 | Pflueger et al. | |
| 5,540,679 A | 7/1996 | Fram et al. | |
| 5,540,681 A | 7/1996 | Strul et al. | |
| 5,542,917 A | 8/1996 | Nita et al. | |
| 5,545,161 A | 8/1996 | Imran | |
| 5,562,100 A | 10/1996 | Kittrell et al. | |
| 5,571,122 A | 11/1996 | Kelly et al. | |
| 5,571,151 A | 11/1996 | Gregory | |
| 5,573,531 A | 11/1996 | Gregory et al. | |
| 5,573,533 A | 11/1996 | Strul | |
| 5,584,831 A | 12/1996 | McKay | |
| 5,584,872 A | 12/1996 | Lafontaine et al. | |
| 5,588,962 A | 12/1996 | Nicholas et al. | |
| 5,599,346 A | 2/1997 | Edwards et al. | |

(56) References Cited

U.S. PATENT DOCUMENTS

| | | |
|---|---|---|
| 5,601,526 A | 2/1997 | Chapelon et al. |
| 5,609,606 A | 3/1997 | O'Boyle et al. |
| 5,626,576 A | 5/1997 | Janssen |
| 5,630,837 A | 5/1997 | Crowley |
| 5,637,090 A | 6/1997 | McGee et al. |
| 5,643,255 A | 7/1997 | Organ |
| 5,643,297 A | 7/1997 | Nordgren et al. |
| 5,647,847 A | 7/1997 | Lafontaine et al. |
| 5,649,923 A | 7/1997 | Gregory et al. |
| 5,651,780 A | 7/1997 | Jackson et al. |
| 5,653,684 A | 8/1997 | Laptewicz et al. |
| 5,662,671 A | 9/1997 | Barbut et al. |
| 5,665,062 A | 9/1997 | Houser |
| 5,665,098 A | 9/1997 | Kelly et al. |
| 5,666,964 A | 9/1997 | Meilus |
| 5,667,490 A | 9/1997 | Keith et al. |
| 5,672,174 A | 9/1997 | Gough et al. |
| 5,676,693 A | 10/1997 | Lafontaine |
| 5,678,296 A | 10/1997 | Fleischhacker et al. |
| 5,681,282 A | 10/1997 | Eggers et al. |
| RE35,656 E | 11/1997 | Feinberg |
| 5,688,266 A | 11/1997 | Edwards et al. |
| 5,693,015 A | 12/1997 | Walker et al. |
| 5,693,029 A | 12/1997 | Leonhardt et al. |
| 5,693,043 A | 12/1997 | Kittrell et al. |
| 5,693,082 A | 12/1997 | Warner et al. |
| 5,695,504 A | 12/1997 | Gifford et al. |
| 5,697,369 A | 12/1997 | Long, Jr. et al. |
| 5,697,909 A | 12/1997 | Eggers et al. |
| 5,702,386 A | 12/1997 | Stern et al. |
| 5,702,433 A | 12/1997 | Taylor et al. |
| 5,706,809 A | 1/1998 | Littmann et al. |
| 5,713,942 A | 2/1998 | Stern et al. |
| 5,715,819 A | 2/1998 | Svenson et al. |
| 5,735,846 A | 4/1998 | Panescu et al. |
| 5,741,214 A | 4/1998 | Ouchi et al. |
| 5,741,248 A | 4/1998 | Stern et al. |
| 5,741,249 A | 4/1998 | Moss et al. |
| 5,743,903 A | 4/1998 | Stern et al. |
| 5,748,347 A | 5/1998 | Erickson |
| 5,749,914 A | 5/1998 | Janssen |
| 5,755,682 A | 5/1998 | Knudson et al. |
| 5,755,715 A | 5/1998 | Stern et al. |
| 5,755,753 A | 5/1998 | Knowlton et al. |
| 5,769,847 A | 6/1998 | Panescu et al. |
| 5,769,880 A | 6/1998 | Truckai et al. |
| 5,775,338 A | 7/1998 | Hastings |
| 5,776,174 A | 7/1998 | Van Tassel |
| 5,779,698 A | 7/1998 | Clayman et al. |
| 5,782,760 A | 7/1998 | Schaer |
| 5,785,702 A | 7/1998 | Murphy et al. |
| 5,797,849 A | 8/1998 | Vesely et al. |
| 5,797,903 A | 8/1998 | Swanson et al. |
| 5,800,484 A | 9/1998 | Gough et al. |
| 5,800,494 A | 9/1998 | Campbell et al. |
| 5,810,802 A | 9/1998 | Panescu et al. |
| 5,810,803 A | 9/1998 | Moss et al. |
| 5,810,810 A | 9/1998 | Tay et al. |
| 5,817,092 A | 10/1998 | Behl |
| 5,817,113 A | 10/1998 | Gifford et al. |
| 5,817,144 A | 10/1998 | Gregory et al. |
| 5,823,956 A | 10/1998 | Roth et al. |
| 5,827,203 A | 10/1998 | Nita et al. |
| 5,827,268 A | 10/1998 | Laufer |
| 5,829,447 A | 11/1998 | Stevens et al. |
| 5,830,213 A | 11/1998 | Panescu et al. |
| 5,830,222 A | 11/1998 | Makower |
| 5,832,228 A | 11/1998 | Holden et al. |
| 5,833,593 A | 11/1998 | Liprie |
| 5,836,874 A | 11/1998 | Swanson et al. |
| 5,840,076 A | 11/1998 | Swanson et al. |
| 5,843,016 A | 12/1998 | Lugnani et al. |
| 5,846,238 A | 12/1998 | Jackson et al. |
| 5,846,239 A | 12/1998 | Swanson et al. |
| 5,846,245 A | 12/1998 | McCarthy et al. |
| 5,848,969 A | 12/1998 | Panescu et al. |
| 5,853,411 A | 12/1998 | Whayne et al. |
| 5,855,614 A | 1/1999 | Stevens et al. |
| 5,860,974 A | 1/1999 | Abele |
| 5,865,801 A | 2/1999 | Houser |
| 5,868,735 A | 2/1999 | Lafontaine et al. |
| 5,868,736 A | 2/1999 | Swanson et al. |
| 5,871,483 A | 2/1999 | Jackson et al. |
| 5,871,524 A | 2/1999 | Knowlton et al. |
| 4,788,975 B1 | 3/1999 | Shturman et al. |
| 5,875,782 A | 3/1999 | Ferrari et al. |
| 5,876,369 A | 3/1999 | Houser |
| 5,876,374 A | 3/1999 | Alba et al. |
| 5,876,397 A | 3/1999 | Edelman et al. |
| 5,879,348 A | 3/1999 | Owens et al. |
| 5,891,114 A | 4/1999 | Chien et al. |
| 5,891,135 A | 4/1999 | Jackson et al. |
| 5,891,136 A | 4/1999 | McGee et al. |
| 5,891,138 A | 4/1999 | Tu et al. |
| 5,895,378 A | 4/1999 | Nita |
| 5,897,552 A | 4/1999 | Edwards et al. |
| 5,902,328 A | 5/1999 | Lafontaine et al. |
| 5,904,651 A | 5/1999 | Swanson et al. |
| 5,904,667 A | 5/1999 | Falwell et al. |
| 5,904,697 A | 5/1999 | Gifford et al. |
| 5,904,709 A | 5/1999 | Arndt et al. |
| 5,906,614 A | 5/1999 | Stern et al. |
| 5,906,623 A | 5/1999 | Peterson |
| 5,906,636 A | 5/1999 | Casscells et al. |
| 5,916,192 A | 6/1999 | Nita et al. |
| 5,916,227 A | 6/1999 | Keith et al. |
| 5,916,239 A | 6/1999 | Geddes et al. |
| 5,919,219 A | 7/1999 | Knowlton et al. |
| 5,924,424 A | 7/1999 | Stevens et al. |
| 5,925,038 A | 7/1999 | Panescu et al. |
| 5,934,284 A | 8/1999 | Plaia et al. |
| 5,935,063 A | 8/1999 | Nguyen |
| 5,938,670 A | 8/1999 | Keith et al. |
| 5,947,977 A | 9/1999 | Slepian et al. |
| 5,948,011 A | 9/1999 | Knowlton et al. |
| 5,951,494 A | 9/1999 | Wang et al. |
| 5,951,539 A | 9/1999 | Nita et al. |
| 5,954,717 A | 9/1999 | Behl et al. |
| 5,957,882 A | 9/1999 | Nita et al. |
| 5,957,941 A | 9/1999 | Ream et al. |
| 5,957,969 A | 9/1999 | Warner et al. |
| 5,961,513 A | 10/1999 | Swanson et al. |
| 5,964,757 A | 10/1999 | Ponzi et al. |
| 5,967,976 A | 10/1999 | Larsen et al. |
| 5,967,978 A | 10/1999 | Littmann et al. |
| 5,967,984 A | 10/1999 | Chu et al. |
| 5,971,975 A | 10/1999 | Mills et al. |
| 5,972,026 A | 10/1999 | Laufer et al. |
| 5,980,563 A | 11/1999 | Tu et al. |
| 5,989,208 A | 11/1999 | Nita et al. |
| 5,989,284 A | 11/1999 | Laufer |
| 5,993,462 A | 11/1999 | Pomeranz et al. |
| 5,997,497 A | 12/1999 | Nita et al. |
| 5,999,678 A | 12/1999 | Murphy et al. |
| 6,004,269 A | 12/1999 | Crowley et al. |
| 6,004,316 A | 12/1999 | Laufer et al. |
| 6,007,514 A | 12/1999 | Nita |
| 6,010,522 A | 1/2000 | Barbut et al. |
| 6,013,033 A * | 1/2000 | Berger et al. .................. 600/466 |
| 6,014,590 A | 1/2000 | Whayne et al. |
| 6,022,309 A | 2/2000 | Celliers et al. |
| 6,024,740 A | 2/2000 | Lesh |
| 6,030,611 A | 2/2000 | Gorecki et al. |
| 6,032,675 A | 3/2000 | Rubinsky et al. |
| 6,033,397 A | 3/2000 | Laufer et al. |
| 6,033,398 A | 3/2000 | Farley et al. |
| 6,036,687 A | 3/2000 | Laufer et al. |
| 6,036,689 A | 3/2000 | Tu et al. |
| 6,041,260 A | 3/2000 | Stern et al. |
| 6,050,994 A | 4/2000 | Sherman et al. |
| 6,052,610 A * | 4/2000 | Koch ........................... 600/424 |
| 6,056,744 A | 5/2000 | Edwards |
| 6,056,746 A | 5/2000 | Goble et al. |
| 6,063,085 A | 5/2000 | Tay et al. |

(56) References Cited

U.S. PATENT DOCUMENTS

| | | |
|---|---|---|
| 6,066,096 A | 5/2000 | Smith et al. |
| 6,066,139 A | 5/2000 | Ryan et al. |
| 6,068,638 A | 5/2000 | Makower |
| 6,068,653 A | 5/2000 | Lafontaine |
| 6,071,277 A | 6/2000 | Farley et al. |
| 6,071,278 A | 6/2000 | Panescu et al. |
| 6,078,839 A | 6/2000 | Carson |
| 6,079,414 A | 6/2000 | Roth |
| 6,080,171 A | 6/2000 | Keith et al. |
| 6,081,749 A | 6/2000 | Ingle et al. |
| 6,086,581 A | 7/2000 | Reynolds et al. |
| 6,093,166 A | 7/2000 | Knudson et al. |
| 6,096,021 A | 8/2000 | Helm et al. |
| 6,099,526 A | 8/2000 | Whayne et al. |
| 6,102,908 A | 8/2000 | Tu et al. |
| 6,106,477 A | 8/2000 | Miesel et al. |
| 6,110,187 A | 8/2000 | Donlon et al. |
| 6,114,311 A | 9/2000 | Parmacek et al. |
| 6,117,101 A | 9/2000 | Diederich et al. |
| 6,117,128 A | 9/2000 | Gregory |
| 6,120,476 A | 9/2000 | Fung et al. |
| 6,120,516 A | 9/2000 | Selmon et al. |
| 6,121,775 A | 9/2000 | Pearlman |
| 6,123,679 A | 9/2000 | Lafaut et al. |
| 6,123,682 A | 9/2000 | Knudson et al. |
| 6,123,702 A | 9/2000 | Swanson et al. |
| 6,123,703 A | 9/2000 | Tu et al. |
| 6,123,718 A | 9/2000 | Tu et al. |
| 6,129,725 A | 10/2000 | Tu et al. |
| 6,135,997 A | 10/2000 | Laufer et al. |
| 6,142,991 A | 11/2000 | Schatzberger et al. |
| 6,142,993 A | 11/2000 | Whayne et al. |
| 6,149,647 A | 11/2000 | Tu et al. |
| 6,152,899 A | 11/2000 | Farley et al. |
| 6,152,912 A | 11/2000 | Jansen et al. |
| 6,156,046 A | 12/2000 | Passafaro et al. |
| 6,158,250 A | 12/2000 | Tibbals et al. |
| 6,159,187 A | 12/2000 | Park et al. |
| 6,159,225 A | 12/2000 | Makower |
| 6,161,048 A | 12/2000 | Sluijter et al. |
| 6,162,184 A | 12/2000 | Swanson et al. |
| 6,165,163 A | 12/2000 | Chien et al. |
| 6,165,172 A | 12/2000 | Farley et al. |
| 6,165,187 A | 12/2000 | Reger et al. |
| 6,168,594 B1 | 1/2001 | Lafontaine et al. |
| 6,171,321 B1 | 1/2001 | Gifford, III et al. |
| 6,179,832 B1 | 1/2001 | Jones et al. |
| 6,179,835 B1 | 1/2001 | Panescu et al. |
| 6,179,859 B1 | 1/2001 | Bates et al. |
| 6,183,468 B1 | 2/2001 | Swanson et al. |
| 6,183,486 B1 | 2/2001 | Snow et al. |
| 6,190,379 B1 | 2/2001 | Heuser et al. |
| 6,191,862 B1 | 2/2001 | Swanson et al. |
| 6,197,021 B1 | 3/2001 | Panescu et al. |
| 6,200,266 B1 | 3/2001 | Shokrollahi et al. |
| 6,203,537 B1 | 3/2001 | Adrian |
| 6,203,561 B1 | 3/2001 | Ramee et al. |
| 6,210,406 B1 | 4/2001 | Webster |
| 6,211,247 B1 | 4/2001 | Goodman |
| 6,217,576 B1 | 4/2001 | Tu et al. |
| 6,219,577 B1 | 4/2001 | Brown, III et al. |
| 6,228,076 B1 | 5/2001 | Winston et al. |
| 6,228,109 B1 | 5/2001 | Tu et al. |
| 6,231,516 B1 | 5/2001 | Keilman et al. |
| 6,231,587 B1 | 5/2001 | Makower |
| 6,235,044 B1 | 5/2001 | Root et al. |
| 6,236,883 B1 | 5/2001 | Ciaccio et al. |
| 6,237,605 B1 | 5/2001 | Vaska et al. |
| 6,238,389 B1 | 5/2001 | Paddock et al. |
| 6,238,392 B1 | 5/2001 | Long |
| 6,241,666 B1 | 6/2001 | Pomeranz et al. |
| 6,241,753 B1 | 6/2001 | Knowlton |
| 6,245,020 B1 | 6/2001 | Moore et al. |
| 6,245,045 B1 | 6/2001 | Stratienko |
| 6,248,126 B1 | 6/2001 | Lesser et al. |
| 6,251,128 B1 | 6/2001 | Knopp et al. |
| 6,258,087 B1 | 7/2001 | Edwards et al. |
| 6,273,886 B1 | 8/2001 | Edwards et al. |
| 6,280,466 B1 | 8/2001 | Kugler et al. |
| 6,283,935 B1 | 9/2001 | Laufer et al. |
| 6,283,959 B1 | 9/2001 | Lalonde et al. |
| 6,284,743 B1 | 9/2001 | Parmacek et al. |
| 6,287,323 B1 | 9/2001 | Hammerslag |
| 6,290,696 B1 | 9/2001 | Lafontaine |
| 6,292,695 B1 | 9/2001 | Webster, Jr. et al. |
| 6,293,942 B1 | 9/2001 | Goble et al. |
| 6,293,943 B1 | 9/2001 | Panescu et al. |
| 6,296,619 B1 | 10/2001 | Brisken et al. |
| 6,298,256 B1 | 10/2001 | Meyer |
| 6,299,379 B1 | 10/2001 | Lewis |
| 6,299,623 B1 | 10/2001 | Wulfman |
| 6,309,379 B1 | 10/2001 | Willard et al. |
| 6,309,399 B1 | 10/2001 | Barbut et al. |
| 6,311,090 B1 | 10/2001 | Knowlton |
| 6,317,615 B1 | 11/2001 | KenKnight et al. |
| 6,319,242 B1 | 11/2001 | Patterson et al. |
| 6,319,251 B1 | 11/2001 | Tu et al. |
| 6,322,559 B1 | 11/2001 | Daulton et al. |
| 6,325,797 B1 | 12/2001 | Stewart et al. |
| 6,325,799 B1 | 12/2001 | Goble |
| 6,328,699 B1 | 12/2001 | Eigler et al. |
| 6,346,074 B1 | 2/2002 | Roth |
| 6,346,104 B2 | 2/2002 | Daly et al. |
| 6,350,248 B1 | 2/2002 | Knudson et al. |
| 6,350,276 B1 | 2/2002 | Knowlton |
| 6,353,751 B1 | 3/2002 | Swanson et al. |
| 6,355,029 B1 | 3/2002 | Joye et al. |
| 6,357,447 B1 | 3/2002 | Swanson et al. |
| 6,361,519 B1 | 3/2002 | Knudson et al. |
| 6,364,840 B1 | 4/2002 | Crowley |
| 6,371,965 B2 | 4/2002 | Gifford, III et al. |
| 6,375,668 B1 | 4/2002 | Gifford et al. |
| 6,377,854 B1 | 4/2002 | Knowlton |
| 6,377,855 B1 | 4/2002 | Knowlton |
| 6,379,352 B1 | 4/2002 | Reynolds et al. |
| 6,379,373 B1 | 4/2002 | Sawhney et al. |
| 6,381,497 B1 | 4/2002 | Knowlton |
| 6,381,498 B1 | 4/2002 | Knowlton |
| 6,383,151 B1 | 5/2002 | Diederich et al. |
| 6,387,105 B1 | 5/2002 | Gifford, III et al. |
| 6,387,380 B1 | 5/2002 | Knowlton |
| 6,389,311 B1 | 5/2002 | Whayne et al. |
| 6,389,314 B2 | 5/2002 | Feiring |
| 6,391,024 B1 | 5/2002 | Sun et al. |
| 6,394,096 B1 | 5/2002 | Constantz |
| 6,394,956 B1 | 5/2002 | Chandrasekaran et al. |
| 6,398,780 B1 | 6/2002 | Farley et al. |
| 6,398,782 B1 | 6/2002 | Pecor et al. |
| 6,398,792 B1 | 6/2002 | O'Connor |
| 6,401,720 B1 | 6/2002 | Stevens et al. |
| 6,402,719 B1 | 6/2002 | Ponzi et al. |
| 6,405,090 B1 | 6/2002 | Knowlton |
| 6,409,723 B1 | 6/2002 | Edwards |
| 6,413,255 B1 | 7/2002 | Stern |
| 6,421,559 B1 | 7/2002 | Pearlman |
| 6,423,057 B1 | 7/2002 | He et al. |
| 6,425,867 B1 | 7/2002 | Vaezy et al. |
| 6,425,912 B1 | 7/2002 | Knowlton |
| 6,427,118 B1 | 7/2002 | Suzuki |
| 6,428,534 B1 | 8/2002 | Joye et al. |
| 6,428,536 B2 | 8/2002 | Panescu et al. |
| 6,430,446 B1 | 8/2002 | Knowlton |
| 6,432,102 B2 | 8/2002 | Joye et al. |
| 6,436,056 B1 | 8/2002 | Wang et al. |
| 6,438,424 B1 | 8/2002 | Knowlton |
| 6,440,125 B1 | 8/2002 | Rentrop |
| 6,442,413 B1 | 8/2002 | Silver |
| 6,443,965 B1 | 9/2002 | Gifford, III et al. |
| 6,445,939 B1 | 9/2002 | Swanson et al. |
| 6,447,505 B2 | 9/2002 | McGovern et al. |
| 6,447,509 B1 | 9/2002 | Bonnet et al. |
| 6,451,034 B1 | 9/2002 | Gifford, III et al. |
| 6,451,044 B1 | 9/2002 | Naghavi et al. |
| 6,453,202 B1 | 9/2002 | Knowlton |

(56) References Cited

U.S. PATENT DOCUMENTS

| | | |
|---|---|---|
| 6,454,737 B1 | 9/2002 | Nita et al. |
| 6,454,757 B1 | 9/2002 | Nita et al. |
| 6,454,775 B1 | 9/2002 | Demarais et al. |
| 6,458,098 B1 | 10/2002 | Kanesaka |
| 6,461,378 B1 | 10/2002 | Knowlton |
| 6,468,276 B1 | 10/2002 | McKay |
| 6,468,297 B1 | 10/2002 | Williams et al. |
| 6,470,216 B1 | 10/2002 | Knowlton |
| 6,470,219 B1 | 10/2002 | Edwards et al. |
| 6,471,696 B1 | 10/2002 | Berube et al. |
| 6,475,213 B1 | 11/2002 | Whayne et al. |
| 6,475,215 B1 | 11/2002 | Tanrisever |
| 6,475,238 B1 | 11/2002 | Fedida et al. |
| 6,477,426 B1 | 11/2002 | Fenn et al. |
| 6,480,745 B2 | 11/2002 | Nelson et al. |
| 6,481,704 B1 | 11/2002 | Koster et al. |
| 6,482,202 B1 | 11/2002 | Goble et al. |
| 6,484,052 B1 | 11/2002 | Visuri et al. |
| 6,485,489 B2 | 11/2002 | Teirstein et al. |
| 6,488,679 B1 | 12/2002 | Swanson et al. |
| 6,489,307 B1 | 12/2002 | Phillips et al. |
| 6,491,705 B2 | 12/2002 | Gifford, III et al. |
| 6,494,891 B1 | 12/2002 | Cornish et al. |
| 6,497,711 B1 | 12/2002 | Plaia et al. |
| 6,500,172 B1 | 12/2002 | Panescu et al. |
| 6,500,174 B1 | 12/2002 | Maguire et al. |
| 6,508,765 B2 | 1/2003 | Suorsa et al. |
| 6,508,804 B2 | 1/2003 | Sarge et al. |
| 6,508,815 B1 | 1/2003 | Strul et al. |
| 6,511,478 B1 | 1/2003 | Burnside et al. |
| 6,511,496 B1 | 1/2003 | Huter et al. |
| 6,511,500 B1 | 1/2003 | Rahme |
| 6,514,236 B1 | 2/2003 | Stratienko |
| 6,514,245 B1 | 2/2003 | Williams et al. |
| 6,514,248 B1 | 2/2003 | Eggers et al. |
| 6,517,534 B1 | 2/2003 | McGovern et al. |
| 6,517,572 B2 | 2/2003 | Kugler et al. |
| 6,522,913 B2 | 2/2003 | Swanson et al. |
| 6,522,926 B1 | 2/2003 | Kieval et al. |
| 6,524,299 B1 | 2/2003 | Tran et al. |
| 6,527,765 B2 | 3/2003 | Kelman et al. |
| 6,527,769 B2 | 3/2003 | Langberg et al. |
| 6,540,761 B2 | 4/2003 | Houser |
| 6,542,781 B1 | 4/2003 | Koblish et al. |
| 6,544,780 B1 | 4/2003 | Wang |
| 6,546,272 B1 | 4/2003 | MacKinnon et al. |
| 6,547,788 B1 | 4/2003 | Maguire et al. |
| 6,549,800 B1 | 4/2003 | Atalar et al. |
| 6,552,796 B2 | 4/2003 | Magnin et al. |
| 6,554,780 B1 | 4/2003 | Sampson et al. |
| 6,558,381 B2 | 5/2003 | Ingle et al. |
| 6,558,382 B2 | 5/2003 | Jahns et al. |
| 6,564,096 B2 | 5/2003 | Mest |
| 6,565,582 B2 | 5/2003 | Gifford, III et al. |
| 6,569,109 B2 | 5/2003 | Sakurai et al. |
| 6,569,177 B1 | 5/2003 | Dillard et al. |
| 6,570,659 B2 | 5/2003 | Schmitt |
| 6,572,551 B1 | 6/2003 | Smith et al. |
| 6,572,612 B2 | 6/2003 | Stewart et al. |
| 6,577,902 B1 | 6/2003 | Laufer et al. |
| 6,579,308 B1 | 6/2003 | Jansen et al. |
| 6,579,311 B1 | 6/2003 | Makower |
| 6,582,423 B1 | 6/2003 | Thapliyal et al. |
| 6,589,238 B2 | 7/2003 | Edwards et al. |
| 6,592,526 B1 | 7/2003 | Lenker |
| 6,592,567 B1 | 7/2003 | Levin et al. |
| 6,595,959 B1 | 7/2003 | Stratienko |
| 6,600,956 B2 | 7/2003 | Maschino et al. |
| 6,602,242 B1 | 8/2003 | Fung et al. |
| 6,602,246 B1 | 8/2003 | Joye et al. |
| 6,605,084 B2 | 8/2003 | Acker et al. |
| 6,623,452 B2 | 9/2003 | Chien et al. |
| 6,623,453 B1 | 9/2003 | Guibert et al. |
| 6,632,193 B1 | 10/2003 | Davison et al. |
| 6,632,196 B1 | 10/2003 | Houser |
| 6,645,223 B2 | 11/2003 | Boyle et al. |
| 6,648,854 B1 | 11/2003 | Patterson et al. |
| 6,648,878 B2 | 11/2003 | Lafontaine |
| 6,648,879 B2 | 11/2003 | Joye et al. |
| 6,651,672 B2 | 11/2003 | Roth |
| 6,652,513 B2 | 11/2003 | Panescu et al. |
| 6,652,515 B1 | 11/2003 | Maguire et al. |
| 6,656,136 B1 * | 12/2003 | Weng et al. .................. 601/2 |
| 6,658,279 B2 | 12/2003 | Swanson et al. |
| 6,659,981 B2 | 12/2003 | Stewart et al. |
| 6,666,858 B2 | 12/2003 | Lafontaine |
| 6,666,863 B2 | 12/2003 | Wentzel et al. |
| 6,669,655 B1 | 12/2003 | Acker et al. |
| 6,669,692 B1 | 12/2003 | Nelson et al. |
| 6,673,040 B1 | 1/2004 | Samson et al. |
| 6,673,064 B1 | 1/2004 | Rentrop |
| 6,673,066 B2 | 1/2004 | Werneth |
| 6,673,090 B2 | 1/2004 | Root et al. |
| 6,673,101 B1 | 1/2004 | Fitzgerald et al. |
| 6,673,290 B1 | 1/2004 | Whayne et al. |
| 6,676,678 B2 | 1/2004 | Gifford, III et al. |
| 6,679,268 B2 | 1/2004 | Stevens et al. |
| 6,681,773 B2 | 1/2004 | Murphy et al. |
| 6,682,541 B1 | 1/2004 | Gifford, III et al. |
| 6,684,098 B2 | 1/2004 | Oshio et al. |
| 6,685,732 B2 | 2/2004 | Kramer |
| 6,685,733 B1 | 2/2004 | Dae et al. |
| 6,689,086 B1 | 2/2004 | Nita et al. |
| 6,689,148 B2 | 2/2004 | Sawhney et al. |
| 6,690,181 B1 | 2/2004 | Dowdeswell et al. |
| 6,692,490 B1 | 2/2004 | Edwards |
| 6,695,830 B2 | 2/2004 | Vigil et al. |
| 6,695,857 B2 | 2/2004 | Gifford, III et al. |
| 6,699,241 B2 | 3/2004 | Rappaport et al. |
| 6,699,257 B2 | 3/2004 | Gifford, III et al. |
| 6,702,748 B1 | 3/2004 | Nita et al. |
| 6,702,811 B2 | 3/2004 | Stewart et al. |
| 6,706,010 B1 | 3/2004 | Miki et al. |
| 6,706,011 B1 | 3/2004 | Murphy-Chutorian et al. |
| 6,706,037 B2 | 3/2004 | Zvuloni et al. |
| 6,709,431 B2 | 3/2004 | Lafontaine |
| 6,711,429 B1 | 3/2004 | Gilboa et al. |
| 6,712,815 B2 | 3/2004 | Sampson et al. |
| 6,714,822 B2 | 3/2004 | King et al. |
| 6,716,184 B2 | 4/2004 | Vaezy et al. |
| 6,720,350 B2 | 4/2004 | Kunz et al. |
| 6,723,043 B2 | 4/2004 | Kleeman et al. |
| 6,723,064 B2 | 4/2004 | Babaev |
| 6,736,811 B2 | 5/2004 | Panescu et al. |
| 6,743,184 B2 | 6/2004 | Sampson et al. |
| 6,746,401 B2 | 6/2004 | Panescu |
| 6,746,464 B1 | 6/2004 | Makower |
| 6,746,474 B2 | 6/2004 | Saadat |
| 6,748,953 B2 | 6/2004 | Sherry et al. |
| 6,749,607 B2 | 6/2004 | Edwards et al. |
| 6,752,805 B2 | 6/2004 | Maguire et al. |
| 6,760,616 B2 | 7/2004 | Hoey et al. |
| 6,763,261 B2 | 7/2004 | Casscells, III et al. |
| 6,764,501 B2 | 7/2004 | Ganz |
| 6,769,433 B2 | 8/2004 | Zikorus et al. |
| 6,770,070 B1 | 8/2004 | Balbierz |
| 6,771,996 B2 | 8/2004 | Bowe et al. |
| 6,773,433 B2 | 8/2004 | Stewart et al. |
| 6,786,900 B2 | 9/2004 | Joye et al. |
| 6,786,901 B2 | 9/2004 | Joye et al. |
| 6,786,904 B2 | 9/2004 | Döscher et al. |
| 6,788,977 B2 | 9/2004 | Fenn et al. |
| 6,790,206 B2 | 9/2004 | Panescu |
| 6,790,222 B2 | 9/2004 | Kugler et al. |
| 6,796,981 B2 | 9/2004 | Wham et al. |
| 6,797,933 B1 | 9/2004 | Mendis et al. |
| 6,797,960 B2 | 9/2004 | Spartiotis et al. |
| 6,800,075 B2 | 10/2004 | Mische et al. |
| 6,802,857 B1 | 10/2004 | Walsh et al. |
| 6,807,444 B2 | 10/2004 | Tu et al. |
| 6,811,550 B2 | 11/2004 | Holland et al. |
| 6,813,520 B2 | 11/2004 | Truckai et al. |
| 6,814,730 B2 | 11/2004 | Li |
| 6,814,733 B2 | 11/2004 | Schwartz et al. |

(56) References Cited

U.S. PATENT DOCUMENTS

| | | |
|---|---|---|
| 6,823,205 B1 | 11/2004 | Jara |
| 6,824,516 B2 | 11/2004 | Batten et al. |
| 6,827,726 B2 | 12/2004 | Parodi |
| 6,827,926 B2 | 12/2004 | Robinson et al. |
| 6,829,497 B2 | 12/2004 | Mogul |
| 6,830,568 B1 | 12/2004 | Kesten et al. |
| 6,837,886 B2 | 1/2005 | Collins et al. |
| 6,837,888 B2 | 1/2005 | Ciarrocca et al. |
| 6,845,267 B2 | 1/2005 | Harrison |
| 6,847,848 B2 | 1/2005 | Sterzer |
| 6,849,073 B2 | 2/2005 | Hoey et al. |
| 6,849,075 B2 | 2/2005 | Bertolero et al. |
| 6,853,425 B2 | 2/2005 | Kim et al. |
| 6,855,123 B2 | 2/2005 | Nita |
| 6,855,143 B2 | 2/2005 | Davison |
| 6,869,431 B2 | 3/2005 | Maguire et al. |
| 6,872,183 B2 | 3/2005 | Sampson et al. |
| 6,884,260 B2 | 4/2005 | Kugler et al. |
| 6,889,694 B2 | 5/2005 | Hooven |
| 6,893,436 B2 | 5/2005 | Woodard et al. |
| 6,895,077 B2 | 5/2005 | Karellas et al. |
| 6,895,265 B2 | 5/2005 | Silver |
| 6,898,454 B2 | 5/2005 | Atalar et al. |
| 6,899,711 B2 | 5/2005 | Stewart et al. |
| 6,899,718 B2 | 5/2005 | Gifford, III et al. |
| 6,905,494 B2 | 6/2005 | Yon et al. |
| 6,908,462 B2 | 6/2005 | Joye et al. |
| 6,909,009 B2 | 6/2005 | Koridze |
| 6,911,026 B1 | 6/2005 | Hall et al. |
| 6,915,806 B2 | 7/2005 | Pacek et al. |
| 6,923,805 B1 | 8/2005 | LaFontaine et al. |
| 6,926,246 B2 | 8/2005 | Ginggen |
| 6,926,713 B2 | 8/2005 | Rioux et al. |
| 6,926,716 B2 | 8/2005 | Baker et al. |
| 6,929,009 B2 | 8/2005 | Makower et al. |
| 6,929,632 B2 | 8/2005 | Nita et al. |
| 6,929,639 B2 | 8/2005 | Lafontaine |
| 6,932,776 B2 | 8/2005 | Carr |
| 6,936,047 B2 | 8/2005 | Nasab et al. |
| 6,942,620 B2 | 9/2005 | Nita et al. |
| 6,942,657 B2 | 9/2005 | Sinofsky et al. |
| 6,942,677 B2 | 9/2005 | Nita et al. |
| 6,942,692 B2 | 9/2005 | Landau et al. |
| 6,949,097 B2 | 9/2005 | Stewart et al. |
| 6,949,121 B1 | 9/2005 | Laguna |
| 6,952,615 B2 | 10/2005 | Satake |
| 6,953,425 B2 | 10/2005 | Brister |
| 6,955,174 B2 | 10/2005 | Joye et al. |
| 6,955,175 B2 | 10/2005 | Stevens et al. |
| 6,959,711 B2 | 11/2005 | Murphy et al. |
| 6,960,207 B2 | 11/2005 | Vanney et al. |
| 6,962,584 B1 | 11/2005 | Stone et al. |
| 6,964,660 B2 | 11/2005 | Maguire et al. |
| 6,966,908 B2 | 11/2005 | Maguire et al. |
| 6,972,015 B2 | 12/2005 | Joye et al. |
| 6,972,024 B1 | 12/2005 | Kilpatrick et al. |
| 6,974,456 B2 | 12/2005 | Edwards et al. |
| 6,978,174 B2 | 12/2005 | Gelfand et al. |
| 6,979,329 B2 | 12/2005 | Burnside et al. |
| 6,979,420 B2 | 12/2005 | Weber |
| 6,984,238 B2 | 1/2006 | Gifford, III et al. |
| 6,985,774 B2 | 1/2006 | Kieval et al. |
| 6,986,739 B2 | 1/2006 | Warren et al. |
| 6,989,009 B2 | 1/2006 | Lafontaine |
| 6,989,010 B2 | 1/2006 | Francischelli et al. |
| 6,991,617 B2 | 1/2006 | Hektner et al. |
| 7,001,378 B2 | 2/2006 | Yon et al. |
| 7,006,858 B2 | 2/2006 | Silver et al. |
| 7,022,105 B1 | 4/2006 | Edwards |
| 7,022,120 B2 | 4/2006 | Lafontaine |
| 7,025,767 B2 | 4/2006 | Schaefer et al. |
| 7,033,322 B2 | 4/2006 | Silver |
| 7,033,372 B1 | 4/2006 | Cahalan |
| 7,041,098 B2 | 5/2006 | Farley et al. |
| 7,050,848 B2 | 5/2006 | Hoey et al. |
| 7,063,670 B2 | 6/2006 | Sampson et al. |
| 7,063,679 B2 | 6/2006 | Maguire et al. |
| 7,063,719 B2 | 6/2006 | Jansen et al. |
| 7,066,895 B2 | 6/2006 | Podany |
| 7,066,900 B2 | 6/2006 | Botto et al. |
| 7,066,904 B2 | 6/2006 | Rosenthal et al. |
| 7,072,720 B2 | 7/2006 | Puskas |
| 7,074,217 B2 | 7/2006 | Strul et al. |
| 7,081,112 B2 | 7/2006 | Joye et al. |
| 7,081,114 B2 | 7/2006 | Rashidi |
| 7,083,614 B2 | 8/2006 | Fjield et al. |
| 7,084,276 B2 | 8/2006 | Vu et al. |
| 7,087,026 B2 | 8/2006 | Callister et al. |
| 7,087,051 B2 | 8/2006 | Bourne et al. |
| 7,087,052 B2 | 8/2006 | Sampson et al. |
| 7,087,053 B2 | 8/2006 | Vanney |
| 7,089,065 B2 | 8/2006 | Westlund et al. |
| 7,097,641 B1 | 8/2006 | Arless et al. |
| 7,100,614 B2 | 9/2006 | Stevens et al. |
| 7,101,368 B2 | 9/2006 | Lafontaine |
| 7,104,983 B2 | 9/2006 | Grasso, III et al. |
| 7,104,987 B2 | 9/2006 | Biggs et al. |
| 7,108,715 B2 | 9/2006 | Lawrence-Brown et al. |
| 7,112,196 B2 | 9/2006 | Brosch et al. |
| 7,112,198 B2 | 9/2006 | Satake |
| 7,112,211 B2 | 9/2006 | Gifford, III et al. |
| 7,122,019 B1 | 10/2006 | Kesten et al. |
| 7,122,033 B2 | 10/2006 | Wood |
| 7,134,438 B2 | 11/2006 | Makower et al. |
| 7,137,963 B2 | 11/2006 | Nita et al. |
| 7,137,980 B2 | 11/2006 | Buysse et al. |
| 7,153,315 B2 | 12/2006 | Miller |
| 7,155,271 B2 | 12/2006 | Halperin et al. |
| 7,157,491 B2 | 1/2007 | Mewshaw et al. |
| 7,157,492 B2 | 1/2007 | Mewshaw et al. |
| 7,158,832 B2 | 1/2007 | Kieval et al. |
| 7,160,296 B2 | 1/2007 | Pearson et al. |
| 7,162,303 B2 | 1/2007 | Levin et al. |
| 7,165,551 B2 | 1/2007 | Edwards et al. |
| 7,169,144 B2 | 1/2007 | Hoey et al. |
| 7,172,589 B2 | 2/2007 | Lafontaine |
| 7,172,610 B2 | 2/2007 | Heitzmann et al. |
| 7,181,261 B2 | 2/2007 | Silver et al. |
| 7,184,811 B2 | 2/2007 | Phan et al. |
| 7,184,827 B1 | 2/2007 | Edwards |
| 7,189,227 B2 | 3/2007 | Lafontaine |
| 7,192,427 B2 | 3/2007 | Chapelon et al. |
| 7,192,586 B2 | 3/2007 | Bander |
| 7,197,354 B2 | 3/2007 | Sobe |
| 7,198,632 B2 | 4/2007 | Lim et al. |
| 7,200,445 B1 | 4/2007 | Dalbec et al. |
| 7,201,749 B2 | 4/2007 | Govari et al. |
| 7,203,537 B2 | 4/2007 | Mower |
| 7,214,234 B2 | 5/2007 | Rapacki et al. |
| 7,220,233 B2 | 5/2007 | Nita et al. |
| 7,220,239 B2 | 5/2007 | Wilson et al. |
| 7,220,257 B1 | 5/2007 | Lafontaine |
| 7,220,270 B2 | 5/2007 | Sawhney et al. |
| 7,232,458 B2 | 6/2007 | Saadat |
| 7,232,459 B2 | 6/2007 | Greenberg et al. |
| 7,238,184 B2 | 7/2007 | Megerman et al. |
| 7,241,273 B2 | 7/2007 | Maguire et al. |
| 7,241,736 B2 | 7/2007 | Hunter et al. |
| 7,247,141 B2 | 7/2007 | Makin et al. |
| 7,250,041 B2 | 7/2007 | Chiu et al. |
| 7,250,440 B2 | 7/2007 | Mewshaw et al. |
| 7,252,664 B2 | 8/2007 | Nasab et al. |
| 7,252,679 B2 | 8/2007 | Fischell et al. |
| 7,264,619 B2 | 9/2007 | Venturelli |
| 7,279,600 B2 | 10/2007 | Mewshaw et al. |
| 7,280,863 B2 | 10/2007 | Shachar |
| 7,282,213 B2 | 10/2007 | Schroeder et al. |
| 7,285,119 B2 | 10/2007 | Stewart et al. |
| 7,285,120 B2 | 10/2007 | Im et al. |
| 7,288,089 B2 | 10/2007 | Yon et al. |
| 7,288,096 B2 | 10/2007 | Chin |
| 7,291,146 B2 | 11/2007 | Steinke et al. |
| 7,293,562 B2 | 11/2007 | Malecki et al. |
| 7,294,125 B2 | 11/2007 | Phalen et al. |

(56) References Cited

U.S. PATENT DOCUMENTS

| | | |
|---|---|---|
| 7,294,126 B2 | 11/2007 | Sampson et al. |
| 7,294,127 B2 | 11/2007 | Leung et al. |
| 7,297,131 B2 | 11/2007 | Nita |
| 7,297,475 B2 | 11/2007 | Koiwai et al. |
| 7,300,433 B2 | 11/2007 | Lane et al. |
| 7,301,108 B2 | 11/2007 | Egitto et al. |
| 7,310,150 B2 | 12/2007 | Guillermo et al. |
| 7,313,430 B2 | 12/2007 | Urquhart et al. |
| 7,314,483 B2 | 1/2008 | Landau et al. |
| 7,317,077 B2 | 1/2008 | Averback et al. |
| 7,323,006 B2 | 1/2008 | Andreas et al. |
| 7,326,206 B2 | 2/2008 | Paul et al. |
| 7,326,226 B2 | 2/2008 | Root et al. |
| 7,326,235 B2 | 2/2008 | Edwards |
| 7,326,237 B2 | 2/2008 | DePalma et al. |
| 7,329,236 B2 | 2/2008 | Kesten et al. |
| 7,335,180 B2 | 2/2008 | Nita et al. |
| 7,335,192 B2 | 2/2008 | Keren et al. |
| 7,338,467 B2 | 3/2008 | Lutter |
| 7,341,570 B2 | 3/2008 | Keren et al. |
| 7,343,195 B2 | 3/2008 | Strommer et al. |
| 7,347,857 B2 | 3/2008 | Anderson et al. |
| 7,348,003 B2 | 3/2008 | Salcedo et al. |
| 7,352,593 B2 | 4/2008 | Zeng et al. |
| 7,354,927 B2 | 4/2008 | Vu |
| 7,359,732 B2 | 4/2008 | Kim et al. |
| 7,361,341 B2 | 4/2008 | Salcedo et al. |
| 7,364,566 B2 | 4/2008 | Elkins et al. |
| 7,367,970 B2 | 5/2008 | Govari et al. |
| 7,367,975 B2 | 5/2008 | Malecki et al. |
| 7,371,231 B2 | 5/2008 | Rioux et al. |
| 7,387,126 B2 | 6/2008 | Cox et al. |
| 7,393,338 B2 | 7/2008 | Nita |
| 7,396,355 B2 | 7/2008 | Goldman et al. |
| 7,402,151 B2 | 7/2008 | Rosenman et al. |
| 7,402,312 B2 | 7/2008 | Rosen et al. |
| 7,404,824 B1 | 7/2008 | Webler et al. |
| 7,406,970 B2 | 8/2008 | Zikorus et al. |
| 7,407,502 B2 | 8/2008 | Strul et al. |
| 7,407,506 B2 | 8/2008 | Makower |
| 7,407,671 B2 | 8/2008 | McBride et al. |
| 7,408,021 B2 | 8/2008 | Averback et al. |
| 7,410,486 B2 | 8/2008 | Fuimaono et al. |
| 7,413,556 B2 | 8/2008 | Zhang et al. |
| 7,425,212 B1 | 9/2008 | Danek et al. |
| 7,426,409 B2 | 9/2008 | Casscells, III et al. |
| 7,435,248 B2 | 10/2008 | Taimisto et al. |
| 7,447,453 B2 | 11/2008 | Kim et al. |
| 7,449,018 B2 | 11/2008 | Kramer |
| 7,452,538 B2 | 11/2008 | Ni et al. |
| 7,473,890 B2 | 1/2009 | Grier et al. |
| 7,476,384 B2 | 1/2009 | Ni et al. |
| 7,479,157 B2 | 1/2009 | Weber et al. |
| 7,481,803 B2 | 1/2009 | Kesten et al. |
| 7,485,104 B2 | 2/2009 | Kieval |
| 7,486,805 B2 | 2/2009 | Krattiger |
| 7,487,780 B2 | 2/2009 | Hooven |
| 7,493,154 B2 | 2/2009 | Bonner et al. |
| 7,494,485 B2 | 2/2009 | Beck et al. |
| 7,494,486 B2 | 2/2009 | Mische et al. |
| 7,494,488 B2 | 2/2009 | Weber |
| 7,494,661 B2 | 2/2009 | Sanders |
| 7,495,439 B2 | 2/2009 | Wiggins |
| 7,497,858 B2 | 3/2009 | Chapelon et al. |
| 7,499,745 B2 | 3/2009 | Littrup et al. |
| 7,500,985 B2 | 3/2009 | Saadat |
| 7,505,812 B1 | 3/2009 | Eggers et al. |
| 7,505,816 B2 | 3/2009 | Schmeling et al. |
| 7,507,233 B2 | 3/2009 | Littrup et al. |
| 7,507,235 B2 | 3/2009 | Keogh et al. |
| 7,511,494 B2 | 3/2009 | Wedeen |
| 7,512,445 B2 | 3/2009 | Truckai et al. |
| 7,527,643 B2 | 5/2009 | Case et al. |
| 7,529,589 B2 | 5/2009 | Williams et al. |
| 7,540,852 B2 | 6/2009 | Nita et al. |
| 7,540,870 B2 | 6/2009 | Babaev |
| RE40,863 E | 7/2009 | Tay et al. |
| 7,556,624 B2 | 7/2009 | Laufer et al. |
| 7,558,625 B2 | 7/2009 | Levin et al. |
| 7,563,247 B2 | 7/2009 | Maguire et al. |
| 7,566,319 B2 | 7/2009 | McAuley et al. |
| 7,569,052 B2 | 8/2009 | Phan et al. |
| 7,582,111 B2 | 9/2009 | Krolik et al. |
| 7,584,004 B2 | 9/2009 | Caparso et al. |
| 7,585,835 B2 | 9/2009 | Hill et al. |
| 7,591,996 B2 | 9/2009 | Hwang et al. |
| 7,597,704 B2 | 10/2009 | Frazier et al. |
| 7,598,228 B2 | 10/2009 | Hattori et al. |
| 7,599,730 B2 | 10/2009 | Hunter et al. |
| 7,603,166 B2 | 10/2009 | Casscells, III et al. |
| 7,604,608 B2 | 10/2009 | Nita et al. |
| 7,604,633 B2 | 10/2009 | Truckai et al. |
| 7,615,015 B2 | 11/2009 | Coleman |
| 7,615,072 B2 | 11/2009 | Rust et al. |
| 7,617,005 B2 | 11/2009 | Demarais et al. |
| 7,620,451 B2 | 11/2009 | Demarais et al. |
| 7,621,902 B2 | 11/2009 | Nita et al. |
| 7,621,929 B2 | 11/2009 | Nita et al. |
| 7,626,015 B2 | 12/2009 | Feinstein et al. |
| 7,626,235 B2 | 12/2009 | Kinoshita |
| 7,632,268 B2 | 12/2009 | Edwards et al. |
| 7,632,845 B2 | 12/2009 | Vu et al. |
| 7,635,383 B2 | 12/2009 | Gumm |
| 7,640,046 B2 | 12/2009 | Pastore et al. |
| 7,641,633 B2 | 1/2010 | Laufer et al. |
| 7,641,679 B2 | 1/2010 | Joye et al. |
| 7,646,544 B2 | 1/2010 | Batchko et al. |
| 7,647,115 B2 | 1/2010 | Levin et al. |
| 7,653,438 B2 | 1/2010 | Deem et al. |
| 7,655,006 B2 | 2/2010 | Sauvageau et al. |
| 7,662,114 B2 | 2/2010 | Seip et al. |
| 7,664,548 B2 | 2/2010 | Amurthur et al. |
| 7,670,279 B2 | 3/2010 | Gertner |
| 7,670,335 B2 | 3/2010 | Keidar |
| 7,671,084 B2 | 3/2010 | Mewshaw et al. |
| 7,678,104 B2 | 3/2010 | Keidar |
| 7,678,106 B2 | 3/2010 | Lee |
| 7,678,108 B2 | 3/2010 | Chrisitian et al. |
| 7,691,080 B2 | 4/2010 | Seward et al. |
| 7,699,809 B2 | 4/2010 | Urmey |
| 7,706,882 B2 | 4/2010 | Francischelli et al. |
| 7,715,912 B2 | 5/2010 | Rezai et al. |
| 7,717,853 B2 | 5/2010 | Nita |
| 7,717,909 B2 | 5/2010 | Strul et al. |
| 7,717,948 B2 | 5/2010 | Demarais et al. |
| 7,722,539 B2 | 5/2010 | Carter et al. |
| 7,725,157 B2 | 5/2010 | Dumoulin et al. |
| 7,727,178 B2 | 6/2010 | Wilson et al. |
| 7,736,317 B2 | 6/2010 | Stephens et al. |
| 7,736,360 B2 | 6/2010 | Mody et al. |
| 7,736,362 B2 | 6/2010 | Eberl et al. |
| 7,738,952 B2 | 6/2010 | Yun et al. |
| 7,740,629 B2 | 6/2010 | Anderson et al. |
| 7,741,299 B2 | 6/2010 | Feinstein et al. |
| 7,742,795 B2 | 6/2010 | Stone et al. |
| 7,744,594 B2 | 6/2010 | Yamazaki et al. |
| 7,753,907 B2 | 7/2010 | DiMatteo et al. |
| 7,756,583 B2 | 7/2010 | Demarais et al. |
| 7,758,510 B2 | 7/2010 | Nita et al. |
| 7,758,520 B2 | 7/2010 | Griffin et al. |
| 7,759,315 B2 | 7/2010 | Cuzzocrea et al. |
| 7,766,833 B2 | 8/2010 | Lee et al. |
| 7,766,878 B2 | 8/2010 | Tremaglio, Jr. et al. |
| 7,766,892 B2 | 8/2010 | Keren et al. |
| 7,767,844 B2 | 8/2010 | Lee et al. |
| 7,769,427 B2 | 8/2010 | Shachar |
| 7,771,372 B2 | 8/2010 | Wilson |
| 7,771,421 B2 | 8/2010 | Stewart et al. |
| 7,776,967 B2 | 8/2010 | Perry et al. |
| 7,777,486 B2 | 8/2010 | Hargreaves et al. |
| 7,780,660 B2 | 8/2010 | Bourne et al. |
| 7,789,876 B2 | 9/2010 | Zikorus et al. |
| 7,792,568 B2 | 9/2010 | Zhong et al. |
| 7,799,021 B2 | 9/2010 | Leung et al. |

(56) References Cited

U.S. PATENT DOCUMENTS

| | | | |
|---|---|---|---|
| 7,803,168 | B2 | 9/2010 | Gifford et al. |
| 7,806,871 | B2 | 10/2010 | Li et al. |
| 7,811,265 | B2 | 10/2010 | Hering et al. |
| 7,811,281 | B1 | 10/2010 | Rentrop |
| 7,811,313 | B2 | 10/2010 | Mon et al. |
| 7,816,511 | B2 | 10/2010 | Kawashima et al. |
| 7,818,053 | B2 | 10/2010 | Kassab |
| 7,819,866 | B2 | 10/2010 | Bednarek |
| 7,822,460 | B2 | 10/2010 | Halperin et al. |
| 7,828,837 | B2 | 11/2010 | Khoury |
| 7,832,407 | B2 | 11/2010 | Gertner |
| 7,833,220 | B2 | 11/2010 | Mon et al. |
| 7,837,676 | B2 | 11/2010 | Sinelnikov et al. |
| 7,837,720 | B2 | 11/2010 | Mon |
| 7,841,978 | B2 | 11/2010 | Gertner |
| 7,846,157 | B2 | 12/2010 | Kozel |
| 7,846,160 | B2 | 12/2010 | Payne et al. |
| 7,846,172 | B2 | 12/2010 | Makower |
| 7,849,860 | B2 | 12/2010 | Makower et al. |
| 7,850,685 | B2 | 12/2010 | Kunis et al. |
| 7,853,333 | B2 | 12/2010 | Demarais |
| 7,854,734 | B2 | 12/2010 | Biggs et al. |
| 7,857,756 | B2 | 12/2010 | Warren et al. |
| 7,862,565 | B2 | 1/2011 | Eder et al. |
| 7,863,897 | B2 | 1/2011 | Slocum, Jr. et al. |
| 7,869,854 | B2 | 1/2011 | Shachar et al. |
| 7,873,417 | B2 | 1/2011 | Demarais et al. |
| 7,887,538 | B2 | 2/2011 | Bleich et al. |
| 7,894,905 | B2 | 2/2011 | Pless et al. |
| 7,896,873 | B2 | 3/2011 | Hiller et al. |
| 7,901,400 | B2 | 3/2011 | Wham et al. |
| 7,901,402 | B2 | 3/2011 | Jones et al. |
| 7,901,420 | B2 | 3/2011 | Dunn |
| 7,905,862 | B2 | 3/2011 | Sampson |
| 7,918,850 | B2 | 4/2011 | Govari et al. |
| 7,927,370 | B2 | 4/2011 | Webler et al. |
| 7,937,143 | B2 | 5/2011 | Demarais et al. |
| 7,938,830 | B2 | 5/2011 | Saadat et al. |
| 7,942,874 | B2 | 5/2011 | Eder et al. |
| 7,942,928 | B2 | 5/2011 | Webler et al. |
| 7,946,976 | B2 | 5/2011 | Gertner |
| 7,950,397 | B2 | 5/2011 | Thapliyal et al. |
| 7,955,293 | B2 | 6/2011 | Nita et al. |
| 7,956,613 | B2 | 6/2011 | Wald |
| 7,959,627 | B2 | 6/2011 | Utley et al. |
| 7,962,854 | B2 | 6/2011 | Vance et al. |
| 7,967,782 | B2 | 6/2011 | Laufer et al. |
| 7,967,808 | B2 | 6/2011 | Fitzgerald et al. |
| 7,972,327 | B2 | 7/2011 | Eberl et al. |
| 7,972,330 | B2 | 7/2011 | Alejandro et al. |
| 7,983,751 | B2 | 7/2011 | Zdeblick et al. |
| 8,001,976 | B2 | 8/2011 | Gertner |
| 8,007,440 | B2 | 8/2011 | Magnin et al. |
| 8,012,147 | B2 | 9/2011 | Lafontaine |
| 8,019,435 | B2 | 9/2011 | Hastings et al. |
| 8,021,362 | B2 | 9/2011 | Deem et al. |
| 8,021,413 | B2 | 9/2011 | Dierking et al. |
| 8,025,661 | B2 | 9/2011 | Arnold et al. |
| 8,027,718 | B2 | 9/2011 | Spinner et al. |
| 8,031,927 | B2 | 10/2011 | Karl et al. |
| 8,033,284 | B2 | 10/2011 | Porter et al. |
| 8,048,144 | B2 | 11/2011 | Thistle et al. |
| 8,052,636 | B2 | 11/2011 | Moll et al. |
| 8,052,700 | B2 | 11/2011 | Dunn |
| 8,062,289 | B2 | 11/2011 | Babaev |
| 8,075,580 | B2 | 12/2011 | Makower |
| 8,080,006 | B2 | 12/2011 | Lafontaine et al. |
| 8,088,127 | B2 | 1/2012 | Mayse et al. |
| 8,116,883 | B2 | 2/2012 | Williams et al. |
| 8,119,183 | B2 | 2/2012 | O'Donoghue et al. |
| 8,120,518 | B2 | 2/2012 | Jang et al. |
| 8,123,741 | B2 | 2/2012 | Marrouche et al. |
| 8,128,617 | B2 | 3/2012 | Bencini et al. |
| 8,131,371 | B2 | 3/2012 | Demarais et al. |
| 8,131,372 | B2 | 3/2012 | Levin et al. |
| 8,131,382 | B2 | 3/2012 | Asada |
| 8,137,274 | B2 | 3/2012 | Weng et al. |
| 8,140,170 | B2 | 3/2012 | Rezai et al. |
| 8,143,316 | B2 | 3/2012 | Ueno |
| 8,145,316 | B2 | 3/2012 | Deem et al. |
| 8,145,317 | B2 | 3/2012 | Demarais et al. |
| 8,150,518 | B2 | 4/2012 | Levin et al. |
| 8,150,519 | B2 | 4/2012 | Demarais et al. |
| 8,150,520 | B2 | 4/2012 | Demarais et al. |
| 8,152,830 | B2 | 4/2012 | Gumm |
| 8,162,933 | B2 | 4/2012 | Francischelli et al. |
| 8,167,805 | B2 * | 5/2012 | Emery et al. ................ 600/439 |
| 8,175,711 | B2 | 5/2012 | Demarais et al. |
| 8,187,261 | B2 | 5/2012 | Watson |
| 8,190,238 | B2 | 5/2012 | Moll et al. |
| 8,192,053 | B2 | 6/2012 | Owen et al. |
| 8,198,611 | B2 | 6/2012 | LaFontaine et al. |
| 8,214,056 | B2 | 7/2012 | Hoffer et al. |
| 8,221,407 | B2 | 7/2012 | Phan et al. |
| 8,226,637 | B2 | 7/2012 | Satake |
| 8,231,617 | B2 | 7/2012 | Satake |
| 8,241,217 | B2 | 8/2012 | Chiang et al. |
| 8,257,724 | B2 | 9/2012 | Cromack et al. |
| 8,257,725 | B2 | 9/2012 | Cromack et al. |
| 8,260,397 | B2 | 9/2012 | Ruff et al. |
| 8,263,104 | B2 | 9/2012 | Ho et al. |
| 8,273,023 | B2 | 9/2012 | Razavi |
| 8,277,379 | B2 | 10/2012 | Lau et al. |
| 8,287,524 | B2 | 10/2012 | Siegel |
| 8,287,532 | B2 | 10/2012 | Carroll et al. |
| 8,292,881 | B2 | 10/2012 | Brannan et al. |
| 8,293,703 | B2 | 10/2012 | Averback et al. |
| 8,295,902 | B2 | 10/2012 | Salahieh et al. |
| 8,295,912 | B2 | 10/2012 | Gertner |
| 8,308,722 | B2 | 11/2012 | Ormsby et al. |
| 8,317,776 | B2 | 11/2012 | Ferren et al. |
| 8,317,810 | B2 | 11/2012 | Stangenes et al. |
| 8,329,179 | B2 | 12/2012 | Ni et al. |
| 8,336,705 | B2 | 12/2012 | Okahisa |
| 8,343,031 | B2 | 1/2013 | Gertner |
| 8,343,145 | B2 | 1/2013 | Brannan |
| 8,347,891 | B2 | 1/2013 | Demarais et al. |
| 8,353,945 | B2 | 1/2013 | Andreas et al. |
| 8,364,237 | B2 | 1/2013 | Stone et al. |
| 8,366,615 | B2 | 2/2013 | Razavi |
| 8,382,697 | B2 | 2/2013 | Brenneman et al. |
| 8,388,680 | B2 | 3/2013 | Starksen et al. |
| 8,396,548 | B2 | 3/2013 | Perry et al. |
| 8,398,629 | B2 | 3/2013 | Thistle |
| 8,401,667 | B2 | 3/2013 | Gustus et al. |
| 8,403,881 | B2 | 3/2013 | Ferren et al. |
| 8,406,877 | B2 | 3/2013 | Smith et al. |
| 8,409,172 | B2 | 4/2013 | Moll et al. |
| 8,409,193 | B2 | 4/2013 | Young et al. |
| 8,409,195 | B2 | 4/2013 | Young |
| 8,418,362 | B2 | 4/2013 | Zerfas et al. |
| 8,452,988 | B2 | 5/2013 | Wang |
| 8,454,594 | B2 | 6/2013 | Demarais et al. |
| 8,460,358 | B2 | 6/2013 | Andreas et al. |
| 8,465,452 | B2 | 6/2013 | Kassab |
| 8,469,919 | B2 | 6/2013 | Ingle et al. |
| 8,473,067 | B2 | 6/2013 | Hastings et al. |
| 8,480,663 | B2 | 7/2013 | Ingle et al. |
| 8,485,992 | B2 | 7/2013 | Griffin et al. |
| 8,486,060 | B2 | 7/2013 | Kotmel et al. |
| 8,486,063 | B2 | 7/2013 | Werneth et al. |
| 8,488,591 | B2 | 7/2013 | Miali et al. |
| 2001/0007070 | A1 | 7/2001 | Stewart et al. |
| 2001/0020126 | A1 | 9/2001 | Swanson et al. |
| 2001/0039419 | A1 | 11/2001 | Francischelli et al. |
| 2002/0022864 | A1 | 2/2002 | Mahvi et al. |
| 2002/0042639 | A1 | 4/2002 | Murphy-Chutorian et al. |
| 2002/0045811 | A1 | 4/2002 | Kittrell et al. |
| 2002/0045890 | A1 | 4/2002 | Celliers et al. |
| 2002/0049375 | A1 | 4/2002 | Strommer et al. |
| 2002/0062146 | A1 | 5/2002 | Makower et al. |
| 2002/0065542 | A1 | 5/2002 | Lax et al. |
| 2002/0072710 | A1 | 6/2002 | Stewart et al. |
| 2002/0087151 | A1 | 7/2002 | Mody et al. |

(56) References Cited

U.S. PATENT DOCUMENTS

| | | |
|---|---|---|
| 2002/0095197 A1 | 7/2002 | Lardo et al. |
| 2002/0107536 A1 | 8/2002 | Hussein |
| 2002/0147480 A1 | 10/2002 | Mamayek |
| 2002/0169444 A1 | 11/2002 | Mest et al. |
| 2002/0198520 A1 | 12/2002 | Coen et al. |
| 2003/0028111 A1 | 2/2003 | Vaezy et al. |
| 2003/0065317 A1 | 4/2003 | Rudie et al. |
| 2003/0092995 A1 | 5/2003 | Thompson |
| 2003/0139689 A1 | 7/2003 | Shturman et al. |
| 2003/0195501 A1 | 10/2003 | Sherman et al. |
| 2003/0199747 A1 | 10/2003 | Michlitsch et al. |
| 2003/0225336 A1 | 12/2003 | Callister et al. |
| 2004/0010118 A1 | 1/2004 | Zerhusen et al. |
| 2004/0019348 A1 | 1/2004 | Stevens et al. |
| 2004/0024371 A1 | 2/2004 | Plicchi et al. |
| 2004/0043030 A1 | 3/2004 | Griffiths et al. |
| 2004/0064090 A1 | 4/2004 | Keren et al. |
| 2004/0073206 A1 | 4/2004 | Foley et al. |
| 2004/0088002 A1 | 5/2004 | Boyle et al. |
| 2004/0093055 A1 | 5/2004 | Bartorelli et al. |
| 2004/0106871 A1 | 6/2004 | Hunyor et al. |
| 2004/0117032 A1 | 6/2004 | Roth |
| 2004/0147915 A1 | 7/2004 | Hasebe |
| 2004/0162550 A1 | 8/2004 | Govari et al. |
| 2004/0162555 A1 | 8/2004 | Farley et al. |
| 2004/0167506 A1 | 8/2004 | Chen |
| 2004/0176757 A1 | 9/2004 | Siheinikov et al. |
| 2004/0186356 A1 | 9/2004 | O'Malley et al. |
| 2004/0187875 A1 | 9/2004 | He et al. |
| 2004/0193211 A1 | 9/2004 | Voegele et al. |
| 2004/0220556 A1 | 11/2004 | Cooper et al. |
| 2004/0243022 A1 | 12/2004 | Carney et al. |
| 2004/0243124 A1 | 12/2004 | Im et al. |
| 2004/0253304 A1 | 12/2004 | Gross et al. |
| 2004/0267250 A1 | 12/2004 | Yon et al. |
| 2005/0010095 A1 | 1/2005 | Stewart et al. |
| 2005/0015125 A1 | 1/2005 | Mioduski et al. |
| 2005/0080374 A1 | 4/2005 | Esch et al. |
| 2005/0129616 A1 | 6/2005 | Salcedo et al. |
| 2005/0137180 A1 | 6/2005 | Robinson et al. |
| 2005/0143817 A1 | 6/2005 | Hunter et al. |
| 2005/0148842 A1 | 7/2005 | Wang et al. |
| 2005/0149069 A1 | 7/2005 | Bertolero et al. |
| 2005/0149080 A1 | 7/2005 | Hunter et al. |
| 2005/0149158 A1 | 7/2005 | Hunter et al. |
| 2005/0149173 A1 | 7/2005 | Hunter et al. |
| 2005/0149175 A1 | 7/2005 | Hunter et al. |
| 2005/0154277 A1 | 7/2005 | Tang et al. |
| 2005/0154445 A1 | 7/2005 | Hunter et al. |
| 2005/0154453 A1 | 7/2005 | Hunter et al. |
| 2005/0154454 A1 | 7/2005 | Hunter et al. |
| 2005/0165389 A1 | 7/2005 | Swain et al. |
| 2005/0165391 A1 | 7/2005 | Maguire et al. |
| 2005/0165467 A1 | 7/2005 | Hunter et al. |
| 2005/0165488 A1 | 7/2005 | Hunter et al. |
| 2005/0175661 A1 | 8/2005 | Hunter et al. |
| 2005/0175662 A1 | 8/2005 | Hunter et al. |
| 2005/0175663 A1 | 8/2005 | Hunter et al. |
| 2005/0177103 A1 | 8/2005 | Hunter et al. |
| 2005/0177225 A1 | 8/2005 | Hunter et al. |
| 2005/0181004 A1 | 8/2005 | Hunter et al. |
| 2005/0181008 A1 | 8/2005 | Hunter et al. |
| 2005/0181011 A1 | 8/2005 | Hunter et al. |
| 2005/0181977 A1 | 8/2005 | Hunter et al. |
| 2005/0182479 A1 | 8/2005 | Bonsignore et al. |
| 2005/0183728 A1 | 8/2005 | Hunter et al. |
| 2005/0186242 A1 | 8/2005 | Hunter et al. |
| 2005/0186243 A1 | 8/2005 | Hunter et al. |
| 2005/0191331 A1 | 9/2005 | Hunter et al. |
| 2005/0203410 A1 | 9/2005 | Jenkins |
| 2005/0209587 A1 | 9/2005 | Joye et al. |
| 2005/0214205 A1 | 9/2005 | Salcedo et al. |
| 2005/0214207 A1 | 9/2005 | Salcedo et al. |
| 2005/0214208 A1 | 9/2005 | Salcedo et al. |
| 2005/0214209 A1 | 9/2005 | Salcedo et al. |
| 2005/0214210 A1 | 9/2005 | Salcedo et al. |
| 2005/0214268 A1 | 9/2005 | Cavanagh et al. |
| 2005/0228286 A1 | 10/2005 | Messerly et al. |
| 2005/0228415 A1 | 10/2005 | Gertner |
| 2005/0228460 A1 | 10/2005 | Levin et al. |
| 2005/0232921 A1 | 10/2005 | Rosen et al. |
| 2005/0234312 A1 | 10/2005 | Suzuki et al. |
| 2005/0245862 A1 | 11/2005 | Seward |
| 2005/0251116 A1 | 11/2005 | Steinke et al. |
| 2005/0252553 A1 | 11/2005 | Ginggen |
| 2005/0256398 A1 | 11/2005 | Hastings et al. |
| 2005/0267556 A1 | 12/2005 | Shuros et al. |
| 2006/0004323 A1 | 1/2006 | Chang et al. |
| 2006/0018949 A1 | 1/2006 | Ammon et al. |
| 2006/0024564 A1 | 2/2006 | Manclaw |
| 2006/0025765 A1 | 2/2006 | Landman et al. |
| 2006/0062786 A1 | 3/2006 | Salcedo et al. |
| 2006/0083194 A1 | 4/2006 | Dhrimaj et al. |
| 2006/0089637 A1 | 4/2006 | Werneth et al. |
| 2006/0089638 A1 | 4/2006 | Carmel et al. |
| 2006/0095096 A1 | 5/2006 | DeBenedictis et al. |
| 2006/0106375 A1 | 5/2006 | Werneth et al. |
| 2006/0142790 A1 | 6/2006 | Gertner |
| 2006/0142801 A1 | 6/2006 | Demarais et al. |
| 2006/0147492 A1 | 7/2006 | Hunter et al. |
| 2006/0167106 A1 | 7/2006 | Zhang et al. |
| 2006/0167498 A1 | 7/2006 | DiLorenzo |
| 2006/0171895 A1 | 8/2006 | Bucay-Couto |
| 2006/0184221 A1 | 8/2006 | Stewart et al. |
| 2006/0195139 A1 | 8/2006 | Gertner |
| 2006/0206150 A1 | 9/2006 | Demarais et al. |
| 2006/0212076 A1 | 9/2006 | Demarais et al. |
| 2006/0212078 A1 | 9/2006 | Demarais et al. |
| 2006/0224153 A1 | 10/2006 | Fischell et al. |
| 2006/0229659 A1 | 10/2006 | Gifford et al. |
| 2006/0235474 A1 | 10/2006 | Demarais et al. |
| 2006/0239921 A1 | 10/2006 | Mangat et al. |
| 2006/0240070 A1 | 10/2006 | Cromack et al. |
| 2006/0241648 A1 | 10/2006 | Bleich et al. |
| 2006/0247266 A1 | 11/2006 | Yamada et al. |
| 2006/0247760 A1 | 11/2006 | Ganesan et al. |
| 2006/0263393 A1 | 11/2006 | Demopulos et al. |
| 2006/0265014 A1 | 11/2006 | Demarais et al. |
| 2006/0265015 A1 | 11/2006 | Demarais et al. |
| 2006/0269555 A1 | 11/2006 | Salcedo et al. |
| 2006/0271111 A1 | 11/2006 | Demarais et al. |
| 2006/0276852 A1 | 12/2006 | Demarais et al. |
| 2006/0287644 A1 | 12/2006 | Inganas et al. |
| 2007/0016184 A1 | 1/2007 | Cropper et al. |
| 2007/0016274 A1 | 1/2007 | Boveja et al. |
| 2007/0027390 A1 | 2/2007 | Maschke et al. |
| 2007/0043077 A1 | 2/2007 | Mewshaw et al. |
| 2007/0043409 A1 | 2/2007 | Brian et al. |
| 2007/0049924 A1 | 3/2007 | Rahn |
| 2007/0066957 A1 | 3/2007 | Demarais et al. |
| 2007/0066972 A1 | 3/2007 | Ormsby et al. |
| 2007/0073151 A1 | 3/2007 | Lee |
| 2007/0093710 A1 | 4/2007 | Maschke |
| 2007/0100405 A1 | 5/2007 | Thompson et al. |
| 2007/0106247 A1 | 5/2007 | Burnett et al. |
| 2007/0112327 A1 | 5/2007 | Yun et al. |
| 2007/0118107 A1 | 5/2007 | Francischelli et al. |
| 2007/0123851 A1 | 5/2007 | Alejandro et al. |
| 2007/0129633 A1 | 6/2007 | Lee et al. |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0149963 A1 | 6/2007 | Matsukuma et al. |
| 2007/0162109 A1 | 7/2007 | Davila et al. |
| 2007/0173805 A1 | 7/2007 | Weinberg et al. |
| 2007/0173899 A1 | 7/2007 | Levin et al. |
| 2007/0179496 A1 | 8/2007 | Swoyer et al. |
| 2007/0198007 A1 | 8/2007 | Govari et al. |
| 2007/0203480 A1 | 8/2007 | Mody et al. |
| 2007/0203549 A1 | 8/2007 | Demarais et al. |
| 2007/0207186 A1 | 9/2007 | Scanlon et al. |
| 2007/0208134 A1 | 9/2007 | Hunter et al. |
| 2007/0208210 A1 | 9/2007 | Gelfand et al. |

(56) References Cited

U.S. PATENT DOCUMENTS

| | | |
|---|---|---|
| 2007/0208256 A1 | 9/2007 | Marilla |
| 2007/0208301 A1 | 9/2007 | Evard et al. |
| 2007/0213735 A1 | 9/2007 | Saadat et al. |
| 2007/0219576 A1 | 9/2007 | Cangialosi |
| 2007/0225781 A1 | 9/2007 | Saadat et al. |
| 2007/0232913 A1 | 10/2007 | Lau et al. |
| 2007/0233170 A1 | 10/2007 | Gertner |
| 2007/0239062 A1 | 10/2007 | Chopra et al. |
| 2007/0248639 A1 | 10/2007 | Demopulos et al. |
| 2007/0249703 A1 | 10/2007 | Mewshaw et al. |
| 2007/0254833 A1 | 11/2007 | Hunter et al. |
| 2007/0265687 A1 | 11/2007 | Deem et al. |
| 2007/0278103 A1 | 12/2007 | Hoerr et al. |
| 2007/0282302 A1 | 12/2007 | Wachsman et al. |
| 2007/0292411 A1 | 12/2007 | Salcedo et al. |
| 2007/0293782 A1 | 12/2007 | Marino |
| 2007/0299043 A1 | 12/2007 | Hunter et al. |
| 2008/0004673 A1 | 1/2008 | Rossing et al. |
| 2008/0009927 A1 | 1/2008 | Vilims |
| 2008/0015501 A1 | 1/2008 | Gertner |
| 2008/0021408 A1 | 1/2008 | Jacobsen et al. |
| 2008/0033049 A1 | 2/2008 | Mewshaw |
| 2008/0039746 A1 | 2/2008 | Hissong et al. |
| 2008/0039830 A1 | 2/2008 | Munger et al. |
| 2008/0051454 A1 | 2/2008 | Wang |
| 2008/0058791 A1 | 3/2008 | Eberl |
| 2008/0064957 A1 | 3/2008 | Spence |
| 2008/0071269 A1 | 3/2008 | Hilario et al. |
| 2008/0071306 A1 | 3/2008 | Gertner |
| 2008/0082109 A1 | 4/2008 | Moll et al. |
| 2008/0086072 A1 | 4/2008 | Bonutti et al. |
| 2008/0086185 A1 | 4/2008 | Amurthur et al. |
| 2008/0091193 A1 | 4/2008 | Kauphusman et al. |
| 2008/0097251 A1 | 4/2008 | Babaev |
| 2008/0097426 A1 | 4/2008 | Root et al. |
| 2008/0108867 A1 | 5/2008 | Zhou |
| 2008/0119879 A1 | 5/2008 | Brenneman et al. |
| 2008/0125772 A1 | 5/2008 | Stone et al. |
| 2008/0132450 A1 | 6/2008 | Lee et al. |
| 2008/0140002 A1 | 6/2008 | Ramzipoor et al. |
| 2008/0146918 A1 | 6/2008 | Magnin et al. |
| 2008/0147002 A1 | 6/2008 | Gertner |
| 2008/0161662 A1 | 7/2008 | Golijanin et al. |
| 2008/0161717 A1 | 7/2008 | Gertner |
| 2008/0161801 A1 | 7/2008 | Steinke et al. |
| 2008/0171944 A1 | 7/2008 | Brenneman et al. |
| 2008/0171974 A1 | 7/2008 | Lafontaine et al. |
| 2008/0172035 A1 | 7/2008 | Starksen et al. |
| 2008/0172104 A1 | 7/2008 | Kieval et al. |
| 2008/0188912 A1 | 8/2008 | Stone et al. |
| 2008/0188913 A1 | 8/2008 | Stone et al. |
| 2008/0208162 A1 | 8/2008 | Joshi |
| 2008/0208169 A1 | 8/2008 | Boyle et al. |
| 2008/0208182 A1 | 8/2008 | Lafontaine |
| 2008/0213331 A1 | 9/2008 | Gelfand et al. |
| 2008/0215117 A1 | 9/2008 | Gross |
| 2008/0221448 A1 | 9/2008 | Khuri-Yakub et al. |
| 2008/0234780 A1 | 9/2008 | Smith |
| 2008/0234790 A1 | 9/2008 | Bayer et al. |
| 2008/0243091 A1 | 10/2008 | Humphreys et al. |
| 2008/0245371 A1 | 10/2008 | Gruber |
| 2008/0249525 A1 | 10/2008 | Lee et al. |
| 2008/0249547 A1 | 10/2008 | Dunn |
| 2008/0255550 A1 | 10/2008 | Bell |
| 2008/0255642 A1 | 10/2008 | Zarins et al. |
| 2008/0262489 A1 | 10/2008 | Steinke |
| 2008/0275484 A1 | 11/2008 | Gertner |
| 2008/0281312 A1 | 11/2008 | Werneth et al. |
| 2008/0281347 A1 | 11/2008 | Gertner |
| 2008/0287783 A1* | 11/2008 | Anderson .................. 600/429 |
| 2008/0287918 A1 | 11/2008 | Rosenman et al. |
| 2008/0294037 A1 | 11/2008 | Richter |
| 2008/0300618 A1 | 12/2008 | Gertner |
| 2008/0312644 A1 | 12/2008 | Fourkas et al. |
| 2008/0312673 A1 | 12/2008 | Viswanathan et al. |
| 2008/0317818 A1 | 12/2008 | Griffith et al. |
| 2009/0018486 A1 | 1/2009 | Goren et al. |
| 2009/0018609 A1 | 1/2009 | DiLorenzo |
| 2009/0024194 A1 | 1/2009 | Arcot-Krishnamurthy et al. |
| 2009/0024195 A1 | 1/2009 | Rezai |
| 2009/0030312 A1 | 1/2009 | Hadjicostis |
| 2009/0030411 A1 | 1/2009 | Werneth et al. |
| 2009/0036948 A1 | 2/2009 | Levin et al. |
| 2009/0043372 A1 | 2/2009 | Northrop et al. |
| 2009/0054082 A1 | 2/2009 | Kim et al. |
| 2009/0062873 A1 | 3/2009 | Wu et al. |
| 2009/0069671 A1* | 3/2009 | Anderson .................. 600/424 |
| 2009/0076409 A1 | 3/2009 | Wu et al. |
| 2009/0088735 A1 | 4/2009 | Abboud et al. |
| 2009/0105631 A1 | 4/2009 | Kieval |
| 2009/0112091 A1 | 4/2009 | Chiang |
| 2009/0112202 A1 | 4/2009 | Young |
| 2009/0118620 A1 | 5/2009 | Tgavalekos et al. |
| 2009/0118726 A1 | 5/2009 | Auth et al. |
| 2009/0125099 A1 | 5/2009 | Weber et al. |
| 2009/0131798 A1 | 5/2009 | Minar et al. |
| 2009/0143640 A1 | 6/2009 | Saadat et al. |
| 2009/0156988 A1 | 6/2009 | Ferren et al. |
| 2009/0157057 A1 | 6/2009 | Ferren et al. |
| 2009/0157161 A1 | 6/2009 | Desai et al. |
| 2009/0171333 A1 | 7/2009 | Hon |
| 2009/0192558 A1 | 7/2009 | Whitehurst et al. |
| 2009/0198223 A1 | 8/2009 | Thilwind et al. |
| 2009/0203962 A1 | 8/2009 | Miller et al. |
| 2009/0203993 A1 | 8/2009 | Mangat et al. |
| 2009/0204134 A1 | 8/2009 | Kassab |
| 2009/0204170 A1 | 8/2009 | Hastings et al. |
| 2009/0209885 A1 | 8/2009 | Babaev |
| 2009/0209949 A1 | 8/2009 | Ingle |
| 2009/0209951 A1 | 8/2009 | Marrouche |
| 2009/0210953 A1 | 8/2009 | Moyer et al. |
| 2009/0216317 A1 | 8/2009 | Cromack et al. |
| 2009/0221939 A1 | 9/2009 | Demarais et al. |
| 2009/0221955 A1 | 9/2009 | Babaev |
| 2009/0226429 A1 | 9/2009 | Salcedo et al. |
| 2009/0240249 A1 | 9/2009 | Chan et al. |
| 2009/0247933 A1 | 10/2009 | Maor et al. |
| 2009/0247966 A1 | 10/2009 | Gunn et al. |
| 2009/0248012 A1 | 10/2009 | Maor et al. |
| 2009/0253974 A1 | 10/2009 | Rahme |
| 2009/0264755 A1 | 10/2009 | Chen et al. |
| 2009/0270850 A1 | 10/2009 | Zhou et al. |
| 2009/0281533 A1 | 11/2009 | Ingle et al. |
| 2009/0287137 A1 | 11/2009 | Crowley |
| 2009/0287202 A1 | 11/2009 | Ingle |
| 2009/0299355 A1 | 12/2009 | Bencini |
| 2009/0299356 A1 | 12/2009 | Watson |
| 2009/0306644 A1 | 12/2009 | Mayse et al. |
| 2009/0318749 A1 | 12/2009 | Stolen et al. |
| 2010/0009267 A1 | 1/2010 | Chase et al. |
| 2010/0030061 A1 | 2/2010 | Canfield et al. |
| 2010/0048983 A1 | 2/2010 | Ball et al. |
| 2010/0049099 A1 | 2/2010 | Thapliyal et al. |
| 2010/0049186 A1 | 2/2010 | Ingle et al. |
| 2010/0049188 A1 | 2/2010 | Nelson et al. |
| 2010/0049191 A1 | 2/2010 | Habib et al. |
| 2010/0049283 A1 | 2/2010 | Johnson |
| 2010/0057150 A1 | 3/2010 | Demarais et al. |
| 2010/0069837 A1 | 3/2010 | Rassat et al. |
| 2010/0076299 A1 | 3/2010 | Gustus et al. |
| 2010/0076425 A1 | 3/2010 | Carroux |
| 2010/0087782 A1 | 4/2010 | Ghaffari et al. |
| 2010/0106005 A1 | 4/2010 | Karczmar et al. |
| 2010/0114244 A1 | 5/2010 | Manda et al. |
| 2010/0130836 A1 | 5/2010 | Malchano et al. |
| 2010/0137860 A1 | 6/2010 | Demarais et al. |
| 2010/0137952 A1 | 6/2010 | Demarais et al. |
| 2010/0160903 A1 | 6/2010 | Krespi |
| 2010/0160906 A1 | 6/2010 | Jarrard |
| 2010/0168624 A1 | 7/2010 | Sliwa |
| 2010/0168731 A1 | 7/2010 | Wu et al. |
| 2010/0168739 A1 | 7/2010 | Wu et al. |
| 2010/0168777 A1 | 7/2010 | Demarais et al. |
| 2010/0174282 A1 | 7/2010 | Demarais et al. |

(56) References Cited

U.S. PATENT DOCUMENTS

| | | | |
|---|---|---|---|
| 2010/0191112 | A1 | 7/2010 | Demarais et al. |
| 2010/0191232 | A1 | 7/2010 | Boveda |
| 2010/0217162 | A1 | 8/2010 | Hissong et al. |
| 2010/0222786 | A1 | 9/2010 | Kassab |
| 2010/0222851 | A1 | 9/2010 | Deem et al. |
| 2010/0222854 | A1 | 9/2010 | Demarais et al. |
| 2010/0228122 | A1 | 9/2010 | Keenan et al. |
| 2010/0249604 | A1 | 9/2010 | Hastings et al. |
| 2010/0249773 | A1 | 9/2010 | Clark et al. |
| 2010/0256616 | A1 | 10/2010 | Katoh et al. |
| 2010/0268217 | A1 | 10/2010 | Habib |
| 2010/0268307 | A1 | 10/2010 | Demarais et al. |
| 2010/0284927 | A1 | 11/2010 | Lu et al. |
| 2010/0286684 | A1 | 11/2010 | Hata et al. |
| 2010/0298821 | A1 | 11/2010 | Garbagnati |
| 2010/0305036 | A1 | 12/2010 | Barnes et al. |
| 2010/0312141 | A1 | 12/2010 | Keast et al. |
| 2010/0324472 | A1 | 12/2010 | Wulfman |
| 2011/0009750 | A1 | 1/2011 | Taylor et al. |
| 2011/0021976 | A1 | 1/2011 | Li et al. |
| 2011/0034832 | A1 | 2/2011 | Cioanta et al. |
| 2011/0040324 | A1 | 2/2011 | McCarthy et al. |
| 2011/0044942 | A1 | 2/2011 | Puri et al. |
| 2011/0060324 | A1 | 3/2011 | Wu et al. |
| 2011/0071400 | A1 | 3/2011 | Hastings et al. |
| 2011/0071401 | A1 | 3/2011 | Hastings et al. |
| 2011/0077498 | A1 | 3/2011 | McDaniel |
| 2011/0092781 | A1* | 4/2011 | Gertner ............... 600/301 |
| 2011/0092880 | A1 | 4/2011 | Gertner |
| 2011/0104061 | A1 | 5/2011 | Seward |
| 2011/0112400 | A1 | 5/2011 | Emery et al. |
| 2011/0118600 | A1 | 5/2011 | Gertner |
| 2011/0118726 | A1 | 5/2011 | De La Rama et al. |
| 2011/0130708 | A1 | 6/2011 | Perry et al. |
| 2011/0137155 | A1 | 6/2011 | Weber et al. |
| 2011/0144479 | A1 | 6/2011 | Hastings et al. |
| 2011/0146673 | A1 | 6/2011 | Keast et al. |
| 2011/0166499 | A1 | 7/2011 | Demarais et al. |
| 2011/0178570 | A1 | 7/2011 | Demarais |
| 2011/0200171 | A1 | 8/2011 | Beetel et al. |
| 2011/0202098 | A1 | 8/2011 | Demarais et al. |
| 2011/0207758 | A1 | 8/2011 | Sobotka et al. |
| 2011/0208096 | A1 | 8/2011 | Demarais et al. |
| 2011/0257523 | A1 | 10/2011 | Hastings et al. |
| 2011/0257564 | A1 | 10/2011 | Demarais et al. |
| 2011/0257622 | A1 | 10/2011 | Salahieh et al. |
| 2011/0257641 | A1 | 10/2011 | Hastings et al. |
| 2011/0257642 | A1 | 10/2011 | Griggs, III |
| 2011/0263921 | A1 | 10/2011 | Vrba et al. |
| 2011/0264011 | A1 | 10/2011 | Wu et al. |
| 2011/0264075 | A1 | 10/2011 | Leung et al. |
| 2011/0264086 | A1 | 10/2011 | Ingle |
| 2011/0264116 | A1 | 10/2011 | Kocur et al. |
| 2011/0270238 | A1 | 11/2011 | Rizq et al. |
| 2011/0306851 | A1 | 12/2011 | Wang |
| 2011/0307034 | A1 | 12/2011 | Hastings |
| 2011/0319809 | A1 | 12/2011 | Smith |
| 2012/0029496 | A1 | 2/2012 | Smith |
| 2012/0029500 | A1 | 2/2012 | Jenson |
| 2012/0029505 | A1 | 2/2012 | Jenson |
| 2012/0029509 | A1 | 2/2012 | Smith |
| 2012/0029510 | A1 | 2/2012 | Haverkost |
| 2012/0029511 | A1 | 2/2012 | Smith et al. |
| 2012/0029512 | A1 | 2/2012 | Willard et al. |
| 2012/0029513 | A1 | 2/2012 | Smith et al. |
| 2012/0059241 | A1 | 3/2012 | Hastings et al. |
| 2012/0059286 | A1 | 3/2012 | Hastings et al. |
| 2012/0065506 | A1 | 3/2012 | Smith |
| 2012/0065554 | A1 | 3/2012 | Pikus |
| 2012/0095461 | A1 | 4/2012 | Herscher et al. |
| 2012/0101413 | A1 | 4/2012 | Beetel et al. |
| 2012/0101490 | A1 | 4/2012 | Smith |
| 2012/0101538 | A1 | 4/2012 | Ballakur et al. |
| 2012/0109021 | A1 | 5/2012 | Hastings et al. |
| 2012/0116382 | A1 | 5/2012 | Ku et al. |
| 2012/0116383 | A1 | 5/2012 | Mauch et al. |
| 2012/0116392 | A1 | 5/2012 | Willard |
| 2012/0116438 | A1 | 5/2012 | Salahieh et al. |
| 2012/0116486 | A1 | 5/2012 | Naga et al. |
| 2012/0123243 | A1 | 5/2012 | Hastings |
| 2012/0123258 | A1 | 5/2012 | Willard |
| 2012/0123261 | A1 | 5/2012 | Jenson et al. |
| 2012/0123303 | A1 | 5/2012 | Sogard et al. |
| 2012/0123406 | A1 | 5/2012 | Edmunds et al. |
| 2012/0130289 | A1 | 5/2012 | Demarais et al. |
| 2012/0130345 | A1 | 5/2012 | Levin et al. |
| 2012/0130359 | A1 | 5/2012 | Turovskiy |
| 2012/0130360 | A1 | 5/2012 | Buckley et al. |
| 2012/0130362 | A1 | 5/2012 | Hastings et al. |
| 2012/0130368 | A1 | 5/2012 | Jenson |
| 2012/0130458 | A1 | 5/2012 | Ryba et al. |
| 2012/0136344 | A1 | 5/2012 | Buckley et al. |
| 2012/0136349 | A1 | 5/2012 | Hastings |
| 2012/0136350 | A1 | 5/2012 | Goshgarian et al. |
| 2012/0136417 | A1 | 5/2012 | Buckley et al. |
| 2012/0136418 | A1 | 5/2012 | Buckley et al. |
| 2012/0143181 | A1 | 6/2012 | Demarais et al. |
| 2012/0143293 | A1 | 6/2012 | Mauch et al. |
| 2012/0143294 | A1 | 6/2012 | Clark et al. |
| 2012/0150267 | A1 | 6/2012 | Buckley et al. |
| 2012/0157986 | A1 | 6/2012 | Stone et al. |
| 2012/0157987 | A1 | 6/2012 | Steinke et al. |
| 2012/0157988 | A1 | 6/2012 | Stone et al. |
| 2012/0157989 | A1 | 6/2012 | Stone et al. |
| 2012/0157992 | A1 | 6/2012 | Smith et al. |
| 2012/0157993 | A1 | 6/2012 | Jenson et al. |
| 2012/0158101 | A1 | 6/2012 | Stone et al. |
| 2012/0158104 | A1 | 6/2012 | Huynh et al. |
| 2012/0172837 | A1 | 7/2012 | Demarais et al. |
| 2012/0172870 | A1 | 7/2012 | Jenson et al. |
| 2012/0184952 | A1 | 7/2012 | Jenson et al. |
| 2012/0197198 | A1 | 8/2012 | Demarais et al. |
| 2012/0197252 | A1 | 8/2012 | Deem et al. |
| 2012/0232409 | A1 | 9/2012 | Stahmann et al. |
| 2012/0265066 | A1 | 10/2012 | Crow et al. |
| 2012/0265198 | A1 | 10/2012 | Crow et al. |
| 2013/0012844 | A1 | 1/2013 | Demarais et al. |
| 2013/0012866 | A1 | 1/2013 | Deem et al. |
| 2013/0012867 | A1 | 1/2013 | Demarais et al. |
| 2013/0013024 | A1 | 1/2013 | Levin et al. |
| 2013/0023865 | A1 | 1/2013 | Steinke et al. |
| 2013/0035681 | A1 | 2/2013 | Subramanaim et al. |
| 2013/0066316 | A1 | 3/2013 | Steinke et al. |
| 2013/0085489 | A1 | 4/2013 | Fain et al. |
| 2013/0090563 | A1 | 4/2013 | Weber |
| 2013/0090578 | A1 | 4/2013 | Smith et al. |
| 2013/0090647 | A1 | 4/2013 | Smith |
| 2013/0090649 | A1 | 4/2013 | Smith et al. |
| 2013/0090650 | A1 | 4/2013 | Jenson et al. |
| 2013/0090651 | A1 | 4/2013 | Smith |
| 2013/0090652 | A1 | 4/2013 | Jenson |
| 2013/0096550 | A1 | 4/2013 | Hill |
| 2013/0096553 | A1 | 4/2013 | Hill et al. |
| 2013/0096554 | A1 | 4/2013 | Groff et al. |
| 2013/0096604 | A1 | 4/2013 | Hanson et al. |
| 2013/0110106 | A1 | 5/2013 | Richardson |
| 2013/0116687 | A1 | 5/2013 | Willard |
| 2013/0165764 | A1 | 6/2013 | Scheuermann et al. |
| 2013/0165844 | A1 | 6/2013 | Shuros et al. |
| 2013/0165916 | A1 | 6/2013 | Mathur et al. |
| 2013/0165917 | A1 | 6/2013 | Mathur et al. |
| 2013/0165920 | A1 | 6/2013 | Weber et al. |
| 2013/0165923 | A1 | 6/2013 | Mathur et al. |
| 2013/0165924 | A1 | 6/2013 | Mathur et al. |
| 2013/0165925 | A1 | 6/2013 | Mathur et al. |
| 2013/0165926 | A1 | 6/2013 | Mathur et al. |
| 2013/0165990 | A1 | 6/2013 | Mathur et al. |
| 2013/0172815 | A1 | 7/2013 | Perry et al. |
| 2013/0172872 | A1 | 7/2013 | Subramaniam et al. |
| 2013/0172877 | A1 | 7/2013 | Subramaniam et al. |
| 2013/0172878 | A1 | 7/2013 | Smith |
| 2013/0172879 | A1 | 7/2013 | Sutermeister |

(56) References Cited

U.S. PATENT DOCUMENTS

| | | | |
|---|---|---|---|
| 2013/0172880 A1 | 7/2013 | Willard | |
| 2013/0172881 A1 | 7/2013 | Hill et al. | |

FOREIGN PATENT DOCUMENTS

| | | |
|---|---|---|
| EP | 1180004 A1 | 2/2002 |
| EP | 1335677 B1 | 8/2003 |
| EP | 1579889 | 9/2005 |
| EP | 1874211 A2 | 1/2008 |
| EP | 1906853 A2 | 4/2008 |
| EP | 1961394 A2 | 8/2008 |
| EP | 1620156 B1 | 7/2009 |
| EP | 2076193 A2 | 7/2009 |
| EP | 2091455 A2 | 8/2009 |
| EP | 2197533 A1 | 6/2010 |
| EP | 2204134 | 7/2010 |
| EP | 2208506 A1 | 7/2010 |
| EP | 1579889 B1 | 8/2010 |
| EP | 2092957 B1 | 1/2011 |
| EP | 2349044 A1 | 8/2011 |
| EP | 2027882 B1 | 10/2011 |
| EP | 2378956 A2 | 10/2011 |
| EP | 2037840 B1 | 12/2011 |
| EP | 2204134 B1 | 4/2012 |
| EP | 2320821 B1 | 10/2012 |
| GB | 2456301 A | 7/2009 |
| WO | 9858588 A1 | 12/1998 |
| WO | 9900060 A1 | 1/1999 |
| WO | 0047118 A1 | 8/2000 |
| WO | WO0047118 | 8/2000 |
| WO | 03026525 A1 | 4/2003 |
| WO | 2004100813 A2 | 11/2004 |
| WO | 2004110258 A2 | 12/2004 |
| WO | WO2004110258 | 12/2004 |
| WO | WO2006022790 | 3/2006 |
| WO | WO2006041847 | 4/2006 |
| WO | WO2006041881 | 4/2006 |
| WO | 2006105121 A2 | 10/2006 |
| WO | WO2007035537 | 3/2007 |
| WO | WO2007078997 | 7/2007 |
| WO | WO2007086965 | 8/2007 |
| WO | WO2007103879 | 9/2007 |
| WO | WO2007103881 | 9/2007 |
| WO | WO2007121309 | 10/2007 |
| WO | WO2007146834 | 12/2007 |
| WO | 2008014465 A2 | 1/2008 |
| WO | WO2008003058 | 1/2008 |
| WO | WO2008061150 | 5/2008 |
| WO | WO2008061152 | 5/2008 |
| WO | WO2008070413 | 6/2008 |
| WO | 2009121017 A1 | 10/2009 |
| WO | 2010067360 A2 | 6/2010 |
| WO | WO2010067360 | 6/2010 |
| WO | WO2010078175 | 7/2010 |
| WO | 2010102310 A2 | 9/2010 |
| WO | WO2010129661 | 11/2010 |
| WO | 2011005901 A2 | 1/2011 |
| WO | 2011053757 A1 | 5/2011 |
| WO | 2011053772 A1 | 5/2011 |
| WO | WO2011053757 | 5/2011 |
| WO | WO2011053772 | 5/2011 |
| WO | 2011091069 A1 | 7/2011 |
| WO | WO2011091069 | 7/2011 |
| WO | 2011130534 A2 | 10/2011 |
| WO | WO2011130005 | 10/2011 |
| WO | WO2011139589 | 11/2011 |
| WO | 2012019156 A1 | 2/2012 |
| WO | WO2012019156 | 2/2012 |
| WO | 2013049601 A2 | 4/2013 |

OTHER PUBLICATIONS

Lafon et al., "Optimizing the Shape of Ultrasound Transducers for Interstitial Thermal Ablation", Med Phys. Mar. 2002; 29(3): 290-7 (abstract only).
G. Ter Haar, "Ultrasound Focal Beam Surgery", Ultrasound in Med. & Biol., 1995, vol. 21, No. 9, pp. 1089-1100.
U.S. Appl. No. 13/225,962, filed Sep. 6, 2011, Hastings.
U.S. Appl. No. 13/243,134, filed Sep. 23, 2011, Sogard et al.
U.S. Appl. No. 13/227,446, filed Sep. 7, 2011, Hastings et al.
U.S. Appl. No. 13/243,114, filed Sep. 23, 2011, Jenson et al.
U.S. Appl. No. 13/283,203, filed Oct. 27, 2011, Hastings.
Blue Cross Blue Shield Medical Policy, "Surgery Section—MRI-Guided Focused Ultrasound (MRgFUS) for the Treatment of Uterine Fibroids and Other Tumors", 2004, 5 pages.
Gentry et al., "Combined 3D Intracardiac Echo and Ultrasound Ablation", Medical Imaging 2003: Ultrasonic and Signal Processing, vol. 5035, 2003, pp. 166-173.
Seip et al., "Transurethral High Intensity Focused Ultrasound: Catheter Based Prototypes and Experimental Results", IEEE Ultrasonics Symposium Proceedings, 2000, 4 pages.
Toytman et al., "Tissue Dissection with Ultrafast Laser Using Extended and Multiple Foci", SPIE Proceedings, Optical Interactions with Tissues and Cells XXI, vol. 7562, 2010, 10 pages.
Zhou et al., "Non-Thermal Ablation of Rabbit Liver VX2 Tumor by Pulsed High Intensity Focused Ultrasound Contrast Agent: Pathological Characteristics", World Journal of Gastroenterology, vol. 14(43), Nov. 21, 2008, pp. 6743-6747.
Invitation to Pay Additional Fees dated Aug. 4, 2011 for PCT Application No. PCT/US2011/032524, 6 pages.
International Search Report and Written Opinion dated Oct. 26, 2011 for PCT Application No. PCT/US2011/032524, 16 pages.
Invitation to Pay Additional Fees dated Jan. 30, 2012 for PCT Application No. PCT/US2011/061157, 7 pages.
International Search Report and Written Opinion dated Dec. 23, 2011 for PCT Application No. PCT/US2011/050731, 14 pages.
Van Den Berg, "Light echoes image the human body," OLE, Oct. 2001, p. 35-37.
"IntraLuminal: Products," IntraLuminal Therapeutics, Inc., 2003, p. 1-9.
"Laser Catheter to Aid Coronary Surgery," TechTalk: MIT, Jan. 9, 1991, p. 1-4.
"Optical Coherence Tomography: LightLab Imaging Starts US Cardiology Clinical Investigations," LightLab Imaging Technology, 2002.
"Optical Coherence Tomography: LightLab Sees Bright Prospects for Cardiac Application of OCT Technology," LightLab Imaging Technology, 2001, vol. 27, No. 35.
"Products—Functional Measurement," VOLCANO Functional Measurement Products US, Mar. 24, 2003, p. 1-2.
Brown et al., "Radiofrequency capacitive heaters: the effect of coupling medium resistivity on power absorption along a mouse leg," Physics in Medicine and Biology, 1993, p. 1-12, vol. 38.
Carrington, "Future of CVI: It's all about plaque: Identification of vulnerable lesions, not 'rusty pipes,' could become cornerstone of preventive cardiology," Diagnostic Imaging, 2001, p. 1-8.
Chen et al., "Percutaneous pulmonary artery denervation completely abolishes experimental pulmonary arterial hypertension in vivo," EuroIntervention, 2013, p. 1-8.
Cimino, "Preventing plaque attack," Mass High Tech, 2001, p. 1-2.
Dahm et al., "Relation of Degree of Laser Debulking of In-Stent Restenosis as a Predictor of Restenosis Rate," The American Journal of Cardiology, 2002, p. 68-70, vol. 90.
De Korte et al., "Characterization of Plaque Components With Intravascular Ultrasound Elastography in Human Femoral and Coronary Arteries In Vitro," Circulation, Aug. 8, 2000, p. 617-623.
Durney et al., "Radiofrequency Radiation Dosimetry Handbook," Oct. 1986, p. 1-2, Fourth Edition.
Durney et al., "Radiofrequency Radiation Dosimetry Handbook: Contents," Oct. 1986, p. 1-5, Fourth Edition.
Fournier-Desseux et al., "Assessment of 1-lead and 2-lead electrode patterns in electrical impedance endotomography," Physiological Measurement, 2005, p. 337-349. Vo. 26, Institute of Physics Publishing.
Fram et al., "Feasibility of Radiofrequency Powered, Thermal Balloon Ablation of Atrioventricular Bypass Tracts Via the Coronary Sinus: In Vivo Canine Studies," PACE, Aug. 1995, p. 1518-1530, vol. 18.

(56) References Cited

OTHER PUBLICATIONS

Fram et al., "Low Pressure Radiofrequency Balloon Angioplasty: Evaluation in Porcine Peripheral Arteries," JACC, 1993, p. 1512-1521, vol. 21, No. 6, American College of Cardiology.
Fujimori et al., "Significant Prevention of In-Stent Restenosis by Evans Blue in Patients with Acute Myocardial Infarction," American Heart Association, 2002.
Fujita et al., "Sarpogrelate, an Antagonist of 5-HT(2A) Receptor, Treatment Reduces Restenosis After Coronary Stenting," American Heart Association, 2002.
Gabriel, "Appendix A: Experimental Data," 1999, p. 1-21.
Gregory et al., "Liquid Core Light Guide for Laser Angioplasty," The Journal of Quantum Electronics, Dec. 1990, p. 2289-2296, vol. 26, No. 12.
Kaplan et al., "Healing after Arterial Dilatation with Radiofrequency Thermal and Nonthermal Balloon Angioplasty Sytems," Journal of Investigative Surgery, 1993, p. 33-52, vol. 6.
Kolata, "New Studies Question Value of Opening Arteries," The New York Times, Mar. 21, 2004, p. 1-5.
Konings et al., "Development of an Intravascular Impedance Catheter for Detection of Fatty Lesions in Arteries," IEEE Transactions on Medical Imaging, Aug. 1997, p. 439-446, vol. 16, No. 4.
Kurtz et al., "Lamellar Refractive Surgery with Scanned Intrastromal Picosecond and Femtosecond Laser Pulses in Animal Eyes," Journal of Refractive Surgery, Sep./Oct. 1998, p. 541-548.
Lee et al., "Thermal Compression and Molding of Atherosclerotic Vascular Tissue With Use of Radiofrequency Energy: Implications for Radiofrequency Balloon Angioplasty," JACC, 1989, p. 1167-1175, vol. 13, No. 5, American College of Cardiology.
Lima et al., "Efficacy and Safety of Oral Sirolimus to Treat and Prevent In-Stent Restenosis: A Pilot Study Results," American Heart Association, 2002, p. 2929.
Lima et al., "Systemic Immunosuppression Inhibits In-Stent Coronary Intimal Proliferation in Renal Transplant Patients," American Heart Association, 2002, p. 2928.
Morice et al., "A Randomized Comparison of a Sirolimus-Eluting Stent With a Standard Stent for Coronary Revascularization," The New England Journal of Medicine, Jun. 6, 2012, p. 1773-1780, vol. 346, No. 23.
Muller-Leisse et al., "Effectiveness and Safety of Ultrasonic Atherosclerotic Plaque Ablation: In Vitro Investigation," CardioVascular and Interventional Radiology, 1993, p. 303-307, vol. 16.
Nair et al., "Regularized Autoregressive Analysis of Intravascular Ultrasound Backscatter: Improvement in Spatial Accuracy of Tissue Maps," IEEE Transactions on Ultrasonics, Apr. 2004, p. 420-431, vol. 51, No. 4.
Resar et al., "Endoluminal Sealing of Vascular Wall Disruptions With Radiofrequency-Heated Balloon Angioplasty," Catheterization and Cardiovascular Diagnosis, 1993, p. 161-167, vol. 29.
Romer et al., "Histopathology of Human Coronary Atherosclerosis by Quantifying Its Chemical Composition With Raman Spectroscopy," Circulation, 1998, p. 878-885, vol. 97.
Schauerte et al., "Catheter Ablation of Cardiac Autonomic Nerves for Prevention of Vagal Atrial Fibrillation," Circulation, 2000, p. 2774-2780, vol. 102.
Scheller et al., "Intracoronary Paclitaxel Added to Contrast Media Inhibits In-Stent Restenosis of Porcine Coronary Arteries," American Heart Association, 2002, p. 2227.
Scheller et al., "Potential solutions to the current problem: coated balloon," EuroIntervention, 2008, p. C63-C66, vol. 4 (Supplement C).
Shaffer, "Scientific basis of laser energy," Clinics in Sports Medicine, 2002, p. 585-598, vol. 21.

Shmatukha et al., "MRI temperature mapping during thermal balloon angioplasty," Physics in Medicine and Biology, 2006, p. N163-N171, vol. 51.
Slager et al., "Vaporization of Atherosclerotic Plaques by Spark Erosion," J Am Coll Cardiol, 1985, p. 21-25.
Stiles et al., "Simulated Characterization of Atherosclerotic Lesions in the Coronary Arteries by Measurement of Bioimpedance," IEEE Transactions on Biomedical Engineering, Jul. 2003, p. 916-921, vol. 50, No. 7.
Suselbeck et al., "In vivo intravascular electric impedance spectroscopy using a new catheter with integrated microelectrodes," Basic Res Cardiol, 2005, p. 28-34, vol. 100.
Suselbeck et al., "Intravascular electric impedance spectroscopy of atherosclerotic lesions using a new impedance catheter system," Basic Res Cardiol, 2005, p. 446-452, vol. 100.
Tepe et al., "Local Delivery of Paclitaxel to Inhibit Restenosis during Angioplasty of the Leg," The New England Journal of Medicine, 2008, p. 689-699, vol. 358.
CardioVascular Technologies Inc., "Heated Balloon Device Technology," 11 pages, 2008.
Strategic Business Development, Inc., "Thermal and Disruptive Angioplasty: A Physician's Guide," 8 pages, 1990.
Zhang et al., "Non-contact Radio-Frequency Ablation for Obtaining Deeper Lesions," IEEE Transaction on Biomedical Engineering, vol. 50, No. 2, 6 pages, Feb. 2003.
Lazebnik et al., "Tissue Strain Analytics Virtual Touch Tissue Imaging and Qualification," Siemens Whitepaper, Oct. 2008, 7 pages.
Han et al., "Third-Generation Cryosurgery for Primary and Recurrent Prostate Caner," BJU International, vol. 93, pp. 14-18.
Zhou et al., "Mechanism Research of Ciyoanalgesia," Forefront Publishing Group, 1995.
Florete, "Cryoblative Procedure for Back Pain," Jacksonville Medicine, Oct. 1998, 10 pages.
Stevenson, "Irrigated RF Ablation: Power Titration and Fluid Management for Optimal Safety Efficacy," 2005, 4 pages.
Giliatt et al., "The Cause of Nerve Damage in Acute Compression," Trans Am Neurol Assoc, 1974: 99; 71-4.
Omura et al., "A Mild Acute Compression Induces Neurapraxia in Rat Sciatic Nerve," The International Journal of Neuroscience, vol. 114 (12), pp. 1561-1572.
Baun, "Interaction with Soft Tissue," Principles of General & Vascular Sonography, Chapter 2, pp. 23-24, Before Mar. 2012.
Blue Cross Blue Shield Medicaly Policy, "Surgery Section—MRI-Guided Focused Ultrasound (MRgFUS) for the Treatment of Uterine Fibroids and Other Tumors," 2005, 5 pages.
Gentry et al., "Combines 3D Intracardiac Echo and Ultrasound Ablation," Medical Imaging 2003: Ultrasonic and Signal Processing, vol. 5035, 2003, pp. 166-173.
Lafon et al., "Optmizing the Shape of Ultrasound Transducers for Interstitial Thermal Ablations," MEd Phys. Mar. 2002; 29(3): 290-7 (abstract only).
G. Ter Haar, "Ultrasound Focal Beam Surgery," Ultrasound in Med. & Biol., 1995, vol. 21, No. 9, pp. 1089-1100.
Seip et al., "Transurethral High Intensity Focused Ultrasound: Catheter Based Prototypes and Experimental Results," IEEE Ultrasonics Symposium Proceeding, 2000, 4 pages.
Toytman et al., "Tissue Dissection with Ultrafast Laser Using Extended and Multiple Foci," SPIE Proceeding, Optical Interactions with Tissues and Cells XXI, vol. 7562, 2010, 10 pages.
Zhoue et al., "Non-Thermal Ablation of Rabbit Liver VX2 Tumore by Pulsed High Intensity Focused Ultrasound Contrast Agent: Pathological Characteristics," World Journal of Gastroenterology, vol. 14(43), Nov. 21, 2008, pp. 6743-6747.
US 8,398,630, 3/2013, Demarais et al. (withdrawn).

* cited by examiner

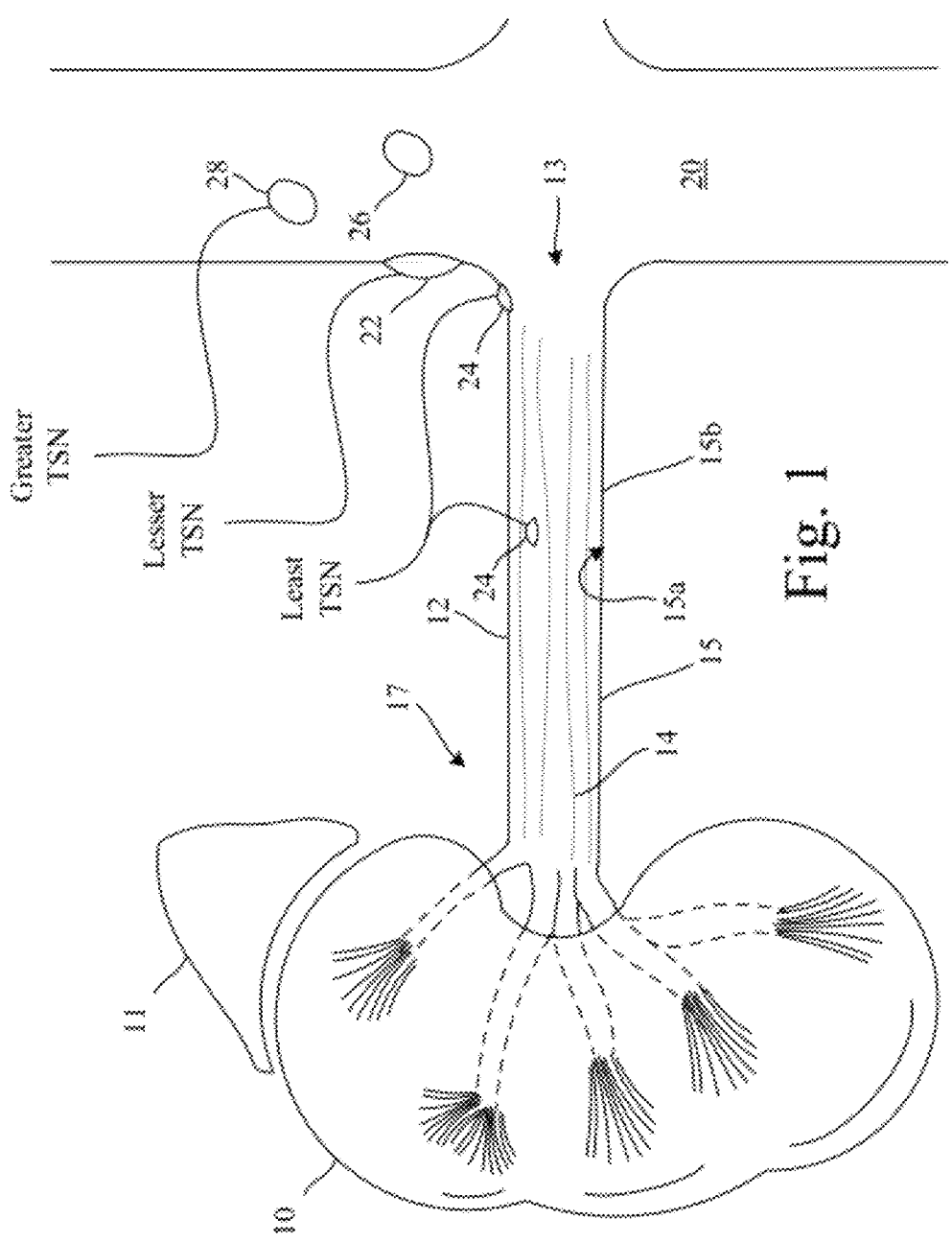

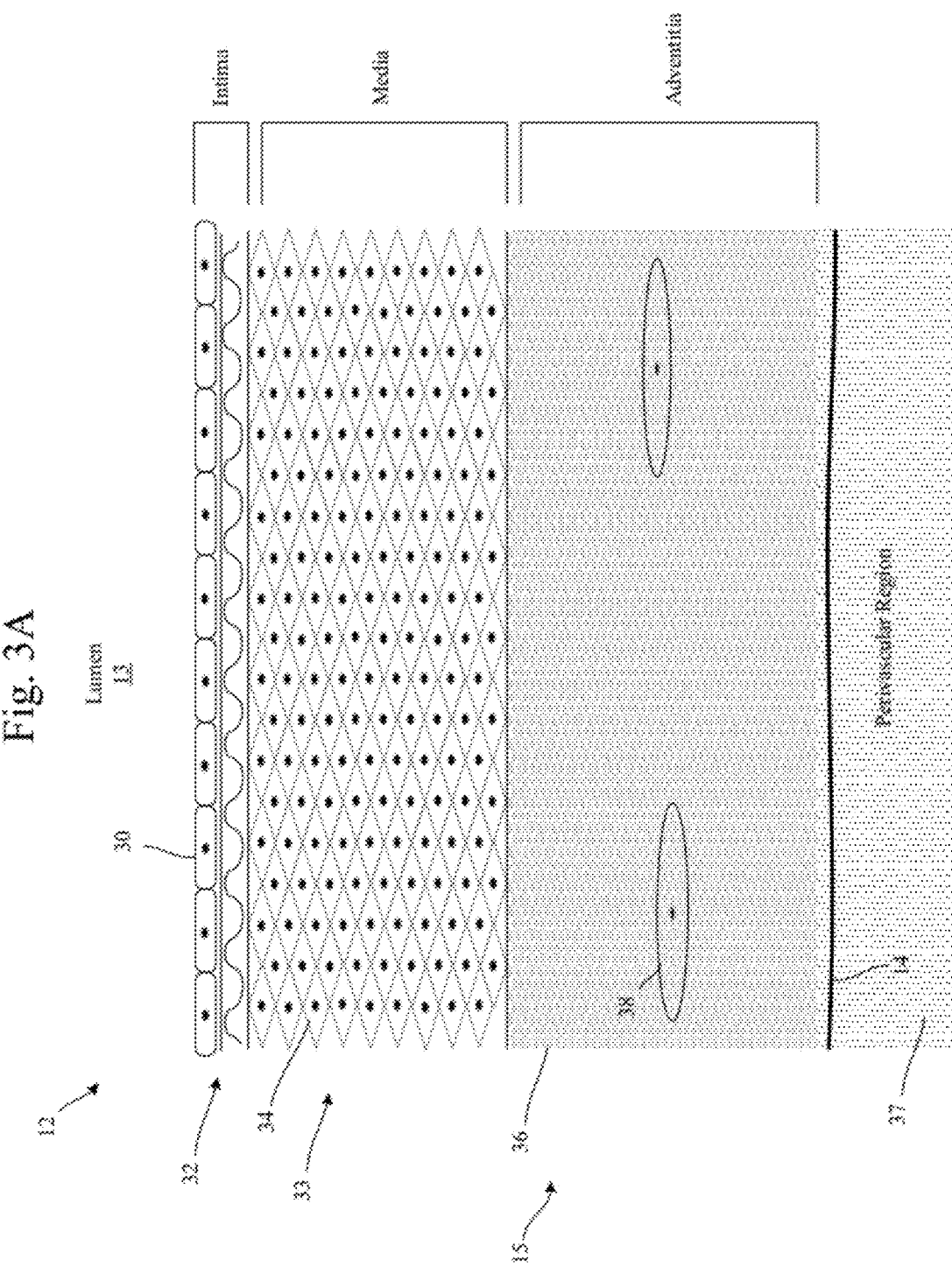

CATHETER GUIDANCE OF EXTERNAL ENERGY FOR RENAL DENERVATION

RELATED PATENT DOCUMENTS

This application claims the benefit of Provisional Patent Application Ser. No. 61/414,735 filed Nov. 17, 2010, to which priority is claimed pursuant to 35 U.S.C. §119(e) and which are hereby incorporated herein by reference.

SUMMARY

Embodiments of the disclosure are directed to apparatuses and methods for guiding externally generated ablative energy to target tissues within the body. Embodiments of the disclosure are directed to apparatuses and methods for guiding externally generated ablative energy to target tissues within the body using an in vivo energy guide apparatus. Various embodiments are directed to apparatuses and methods involving localizing an energy guide apparatus positioned within a target vessel, such as a renal artery, and directing externally generated ablative energy to target tissue of the body, such as perivascular renal nerve tissue.

In accordance with various embodiments, an in vivo apparatus includes a flexible shaft having a proximal end, a distal end, and a length sufficient to access a patient's renal artery relative to a percutaneous access location. An energy guide apparatus is provided at the distal end of the shaft and dimensioned for deployment within the renal artery. An ex vivo apparatus includes an arrangement configured to localize the energy guide apparatus within the renal artery, and an energy source configured to direct ablative energy to target tissue located a predetermined distance from the localized energy guide apparatus. The target tissue includes perivascular renal nerve tissue adjacent the renal artery.

According to some embodiments, an apparatus includes a flexible shaft having a proximal end, a distal end, and a length sufficient to access a patient's renal artery relative to a percutaneous access location. An energy guide apparatus is provided at the distal end of the shaft and dimensioned for deployment within the renal artery. The energy guide apparatus is configured to generate an energy beacon that facilitates locating of the energy guide apparatus within the renal artery. An external system includes a receiver configured to receive the energy beacon, a processor configured to localize the energy guide apparatus based at least in part on the received energy beacon, and an energy source configured to direct ablative energy to target tissue located a predetermined distance from the localized energy guide apparatus. The target tissue includes perivascular renal nerve tissue.

According to other embodiments, an in vivo apparatus includes a flexible shaft having a proximal end, a distal end, and a length sufficient to access a patient's renal artery relative to a percutaneous access location. An energy guide apparatus is provided at the distal end of the shaft and dimensioned for deployment within the renal artery. The energy guide apparatus includes a magnetic field generator configured to generate a rotating magnetic field, and an ultrasound generator configured to generate a rotating beam of acoustic energy. A support structure is provided at the distal end of the shaft and transformable between a low-profile introduction configuration and a deployed configuration. The support structure serves to center the energy guide apparatus within the renal artery when in the deployed configuration. An ex vivo apparatus includes an array of magnetic field sensors configured to sense the rotating magnetic field, and an ultrasound transducer array configured to detect the rotating beam of acoustic energy. A processor is configured to localize the energy guide apparatus based at least in part on the sensed rotating magnetic field and the detected rotating beam of acoustic energy. An energy source is configured to direct ablative energy to target tissue located a predetermined distance from the localized energy guide apparatus. The target tissue includes perivascular renal nerve tissue.

In accordance with various embodiments, a method involves localizing an energy guide apparatus positioned within a renal artery of a patient, and directing ablative energy to target tissue located a predetermined distance from the localized energy guide apparatus. The target tissue includes perivascular renal nerve tissue.

According to some embodiments, a method involves generating, at an energy guide apparatus positioned within a patient's renal artery, a rotating magnetic field. The method also involves generating, at the energy guide apparatus, a rotating beam of acoustic energy. The method further involves sensing, externally of the patient, the rotating magnetic field, detecting, externally of the patient, the rotating acoustic energy beam, and localizing the energy guide apparatus based at least in part on the sensed rotating magnetic field and the detected rotating acoustic energy beam.

These and other features can be understood in view of the following detailed discussion and the accompanying drawings.

BRIEF DESCRIPTION OF THE DRAWINGS

FIG. 1 is an illustration of a right kidney and renal vasculature including a renal artery branching laterally from the abdominal aorta;

FIG. 3A illustrates various tissue layers of the wall of the renal artery;

DETAILED DESCRIPTION

Figure 2A:
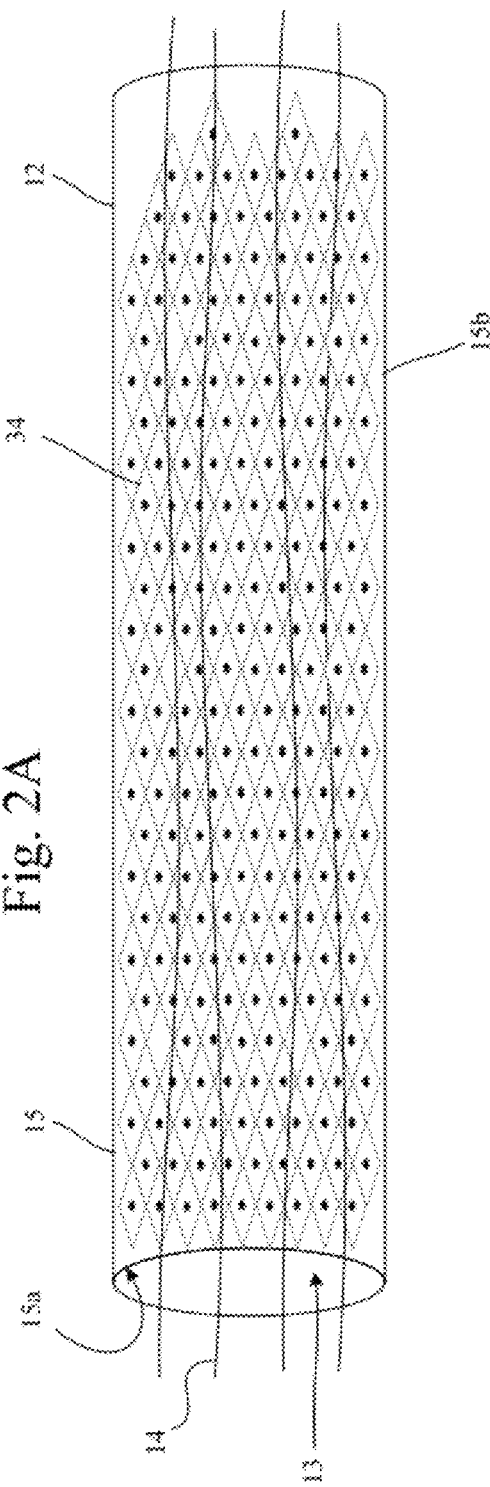
FIGS. 2A and 2B illustrate sympathetic innervation of the renal artery.

Renal denervation has been performed as a therapy for refractory hypertension using surgical and radiofrequency (RF) ablation interventions. Surgical denervation is considered too invasive and too morbid in the modern era of drug therapy. RF ablation of the renal nerves using an RF tip catheter placed against the wall of the renal artery is a promising new technology. However, it unavoidably does some damage to the wall of the renal artery, with side effects that may not be fully known until the procedure becomes widely performed.

External beam ablation of the renal nerves has the potential to avoid damage to the adjacent artery wall, providing that the beam can be targeted precisely. Since the intima and media of the artery wall may be within a few millimeters of the renal nerves, targeting of an external beam must be very precise to avoid damage. According to various embodiments, a position and orientation system of the disclosure is capable of sensing the position of a target within the body to within one mm center-to-center of the actual position of the target. While renal blood flow does cool the artery wall, the external beam generates heat on the outside surface of the artery at the location of the renal nerves, with no heat deposited directly on the inside artery wall surface.

Embodiments of the disclosures are directed to a catheter apparatus configured to precisely locate the renal nerves and guide the external beam ablation. According to various embodiments, a micro-motor driven intravascular ultrasound (IVUS) catheter is placed into the renal artery proximate a site chosen for ablation of adjacent renal nerves. An array of acoustic transducers is placed against the patient's skin adjacent the region of the renal artery. The IVUS catheter projects a conical beam of ultrasound energy that rotates in a plane perpendicular to the catheter long axis. The IVUS beam is received by the transducers in the external array, to identify the location of the IVUS catheter residing in the renal artery.

The IVUS catheter may be centered in the renal artery, for example by inflating a balloon around the imaging core. The diameter of the renal artery may be determined from the IVUS image, or from quantitative angiography of the renal artery, and this information may be used to direct the external beam of ultrasound to sites that are adjacent to the artery wall, but located a short distance away from the inside of the artery wall. Recent studies of human cadavers have revealed that renal nerves can lie as close as about 0.5 mm from the lumen of a renal artery, with most renal nerves lying within about 3.5 mm of the artery lumen. Other structures of the body, such as bowel, can be as close as 4 mm from the artery wall. As a general rule, a relatively safe target zone for performing renal denervation in accordance with embodiments of the disclosure would be a zone between about 0.5 to 3.5 mm from the lumen wall of a renal artery. The size of the ablation zone considered to be safe is, of course, highly dependent on the anatomy of a particular patient. As is discussed below, human renal nerves have been found lying out as far as about 7 mm from the lumen wall of a renal artery. As such, the size of the ablation zone can be as deep as between 0.5 and 7 mm from the lumen wall of a renal artery.

According to some embodiments, the magnetic field of a magnet used to rotate a mirror of the IVUS catheter is sensed by an array of external magnetic sensors that are synchronized to the magnet rotation. The magnetic sensor data may be used to precisely localize the IVUS transducer (e.g., a component of the IVUS transducer, such as a rotating magnet of a micro-motor) relative to a fixed external reference frame of the external magnetic sensors, which is in a measured relationship relative to a reference frame of an external energy source, such as a high-intensity focused ultrasound (HIFU) array. Localizing the IVUS transducer preferably involves determining the Cartesian coordinates and orientation angle of the IVUS transducer. Data from the rotating IVUS beam and the localization of the rotating magnet are combined to precisely guide a phased array ultrasound ablation beam to perivascular renal nerve tissue adjacent the renal nerve. Ablation is performed at points around the renal artery. Two or more locations of the external array may be needed to complete a circumferential ablation. The IVUS catheter may image adjacent tissue to assess the extent and location of the ablation.

Other embodiments include guidance of an external beam of x-ray or gamma-ray radiation. According to these embodiments, a radiopaque marker on the catheter, for example the stator of an IVUS micro-motor, may be used to locate the catheter tip, for example using an external CT scanner. A second, real time localization is preferably provided by sensing the rotating magnetic field of the micro-motor. The CT scan may be displayed and co-registered with the magnetic localization system and external radiation source. Radiation may be projected from multiple angles with beams that converge at the target site of ablation.

In the context of various embodiments described herein, localizing a vascular device, such as an energy guide apparatus or an IVUS transducer, is intended to refer to localization of a component or feature of the vascular device. In some embodiments, localization of an energy guide apparatus or and IVUS transducer involves localizing a specific component of the energy guide apparatus or IVUS transducer with high precision. Suitable components or features include those that can be readily detected by an external system and allow for precise measuring of the Cartesian coordinates and orientation angle of the component or feature. Two representative examples of suitable components or features are radiopaque marker(s) and a rotating magnet of an IVUS micro-motor.

By knowing the location of the component or feature of the vascular device, the spatial relationship between the component or feature and the exterior surfaces of a housing or shaft wall that encloses the component or feature can be precisely measured. As such, localization of the component or feature can account for such distances when determining the spacing between the localized component or feature and the inner wall of the renal artery, for example.

According to various embodiments, a distal end of a catheter includes a rotating magnet, a radiopaque component such as a Pt—Ir stator, and an IVUS transducer. Localization of one or more of the IVUS beam source, the rotating magnet, or the radiopaque element can be used to guide a beam of energy from outside the patient to target ablation sites on the renal nerves adjacent the renal artery. Energy sources can include high-intensity focused ultrasound, x-ray, or gamma-ray radiation.

In various embodiments, an ultrasound beam generated at the distal end of a catheter positioned within a renal artery can be received by an external array of ultrasound transducers to locate target ablation sites around the renal artery outside artery wall. The magnetic field of the rotating magnet may be sensed by external magnetic sensors to precisely determine to Cartesian coordinates and orientation angle of the magnet, and help target the ablation. IVUS images may be obtained before, during, and after the ablation to assess the extent and location of the ablation.

According to embodiments that utilize HIFU ablation, an external HIFU array may project beams of ultrasound energy at a frequency in the range of 1 MHz to 5 MHz. In simplified embodiments, the IVUS transducer can generate an ultrasound beam with the same frequency as the external HIFU array. In this case, the HIFU array elements can receive the energy from the IVUS transducer and compute its location relative the HIFU array. In more complex embodiments, either or both of the HIFU array or the IVUS catheter may contain multiple transducers that project beams for ablation or imaging at multiple frequencies.

In some embodiments, an external HIFU array is first operated in a low-intensity imaging mode to create an image of the IVUS catheter to help target the ablation. The magnetic localization may be combined with the external array data to more precisely target ablation sites. The external HIFU array can then be operated in the high intensity HIFU mode to ablate target tissue. Meanwhile, the IVUS catheter may be generating images of the tissues surrounding renal artery to detect and assess ablated tissue. The IVUS image may be used to guide the location and intensity of the external beams. In these embodiments, the HIFU transducer elements may operate at a frequency of 1 MHz while the IVUS transducer may operate at 40 MHz.

A benefit gained by generating an ultrasound beam in the IVUS catheter that is sensed by the external HIFU array is that attenuation by tissue occurs on a single pass of the beam through the tissue. By contrast, echo imaging suffers attenuation going into and coming back out of tissue. Another benefit can be gained by using the external HIFU array for imaging and using the internal ultrasound transducer (e.g., an IVUS) to generate the beam of ultrasound energy may yield resolution high enough to identify nerve bundles. Using this approach would allow renal nerves that lie farther from the lumen of the renal artery to be targeted. For example, renal nerves have been found lying up to 7 mm away from a renal artery, especially in the direction of the renal vein. When targeting perivascular renal nerves lying relatively far from the renal arteries, it is important to image neighboring organ tissue, such as the colon or renal vein, to avoid abating such tissues.

Multiple methodologies exist for locating the tip of a catheter placed within the body. One methodology involves sensing the magnetic field of a rotating magnet at the catheter tip with an array of external magnetic sensors. Another methodology involves using an external array of ultrasound transducers in a low-intensity imaging mode to generate an image of the catheter and surrounding tissues. In this mode, the image of the catheter tip may be enhanced by inflating a tip balloon with ultrasound contrast media or constructing the distal catheter with ultrasound reflective materials. A further methodology involves projecting a rotating beam of ultrasound energy from the catheter tip that is sensed by the external array used to locate the catheter tip. Another methodology involves generating a CT scan of the region of the renal artery to image one or more radiopaque elements in the catheter tip. This image may be enhanced by injecting x-ray contrast media into the artery and/or into a balloon at the catheter tip.

Other localization methodologies may be used in accordance with other embodiments including, for example, generating magnetic fields in the region of the catheter tip from an array of external currents, and sensing these magnetic fields using magnetic sensors in the catheter tip for localization. In other embodiments, high frequency electrical currents may be conducted into the patient from strategically located leads placed on the patient's skin. Localization can be accomplished by sensing these currents with exposed electrodes at one or more sites proximate the catheter tip.

A variety of methodologies may be used for co-registering external equipment and images. Representative examples include optical, RF or radio, ultrasound and magnetic field means to send and sense signals between catheters in the body and external equipment and between external equipments. Co-registration between imaging modalities may be enhanced by attaching markers to the patient that show up in the multiple images. In some configurations, the markers are anatomical features of the patient.

Various embodiments of the disclosure are directed to apparatuses and methods for renal denervation for treating hypertension. Hypertension is a chronic medical condition in which the blood pressure is elevated. Persistent hypertension is a significant risk factor associated with a variety of adverse medical conditions, including heart attacks, heart failure, arterial aneurysms, and strokes. Persistent hypertension is a leading cause of chronic renal failure. Hyperactivity of the sympathetic nervous system serving the kidneys is associated with hypertension and its progression. Deactivation of nerves in the kidneys via renal denervation can reduce blood pressure, and may be a viable treatment option for many patients with hypertension who do not respond to conventional drugs.

The kidneys are instrumental in a number of body processes, including blood filtration, regulation of fluid balance, blood pressure control, electrolyte balance, and hormone production. One primary function of the kidneys is to remove toxins, mineral salts, and water from the blood to form urine. The kidneys receive about 20-25% of cardiac output through the renal arteries that branch left and right from the abdominal aorta, entering each kidney at the concave surface of the kidneys, the renal hilum.

Blood flows into the kidneys through the renal artery and the afferent arteriole, entering the filtration portion of the kidney, the renal corpuscle. The renal corpuscle is composed of the glomerulus, a thicket of capillaries, surrounded by a fluid-filled, cup-like sac called Bowman's capsule. Solutes in the blood are filtered through the very thin capillary walls of the glomerulus due to the pressure gradient that exists between the blood in the capillaries and the fluid in the Bowman's capsule. The pressure gradient is controlled by the contraction or dilation of the arterioles. After filtration occurs, the filtered blood moves through the efferent arteriole and the peritubular capillaries, converging in the interlobular veins, and finally exiting the kidney through the renal vein.

Particles and fluid filtered from the blood move from the Bowman's capsule through a number of tubules to a collecting duct. Urine is formed in the collecting duct and then exits through the ureter and bladder. The tubules are surrounded by the peritubular capillaries (containing the filtered blood). As the filtrate moves through the tubules and toward the collecting duct, nutrients, water, and electrolytes, such as sodium and chloride, are reabsorbed into the blood.

The kidneys are innervated by the renal plexus which emanates primarily from the aorticorenal ganglion. Renal ganglia are formed by the nerves of the renal plexus as the nerves follow along the course of the renal artery and into the kidney. The renal nerves are part of the autonomic nervous system which includes sympathetic and parasympathetic components. The sympathetic nervous system is known to be the system that provides the bodies "fight or flight" response, whereas the parasympathetic nervous system provides the "rest and digest" response. Stimulation of sympathetic nerve activity triggers the sympathetic response which causes the kidneys to increase production of hormones that increase vasoconstriction and fluid retention. This process is referred to as the renin-angiotensin-aldosterone-system (RAAS) response to increased renal sympathetic nerve activity.

In response to a reduction in blood volume, the kidneys secrete renin, which stimulates the production of angiotensin. Angiotensin causes blood vessels to constrict, resulting in increased blood pressure, and also stimulates the secretion of the hormone aldosterone from the adrenal cortex. Aldosterone causes the tubules of the kidneys to increase the reabsorption of sodium and water, which increases the volume of fluid in the body and blood pressure.

Congestive heart failure (CHF) is a condition that has been linked to kidney function. CHF occurs when the heart is unable to pump blood effectively throughout the body. When blood flow drops, renal function degrades because of insufficient perfusion of the blood within the renal corpuscles. The decreased blood flow to the kidneys triggers an increase in sympathetic nervous system activity (i.e., the RAAS becomes too active) that causes the kidneys to secrete hormones that increase fluid retention and vasorestriction. Fluid retention and vasorestriction in turn increases the peripheral resistance of the circulatory system, placing an even greater load on the heart, which diminishes blood flow further. If the deterioration in cardiac and renal functioning continues, eventually the body becomes overwhelmed, and an episode of heart failure decompensation occurs, often leading to hospitalization of the patient.

FIG. 1 is an illustration of a right kidney 10 and renal vasculature including a renal artery 12 branching laterally from the abdominal aorta 20. In FIG. 1, only the right kidney 10 is shown for purposes of simplicity of explanation, but reference will be made herein to both right and left kidneys and associated renal vasculature and nervous system structures, all of which are contemplated within the context of embodiments of the disclosure. The renal artery 12 is purposefully shown to be disproportionately larger than the right kidney 10 and abdominal aorta 20 in order to facilitate discussion of various features and embodiments of the present disclosure.

The right and left kidneys are supplied with blood from the right and left renal arteries that branch from respective right and left lateral surfaces of the abdominal aorta 20. Each of the right and left renal arteries is directed across the crus of the diaphragm, so as to form nearly a right angle with the abdominal aorta 20. The right and left renal arteries extend generally from the abdominal aorta 20 to respective renal sinuses proximate the hilum 17 of the kidneys, and branch into segmental arteries and then interlobular arteries within the kidney 10. The interlobular arteries radiate outward, penetrating the renal capsule and extending through the renal columns between the renal pyramids. Typically, the kidneys receive about 20% of total cardiac output which, for normal persons, represents about 1200 mL of blood flow through the kidneys per minute.

The primary function of the kidneys is to maintain water and electrolyte balance for the body by controlling the production and concentration of urine. In producing urine, the kidneys excrete wastes such as urea and ammonium. The kidneys also control reabsorption of glucose and amino acids, and are important in the production of hormones including vitamin D, renin and erythropoietin.

An important secondary function of the kidneys is to control metabolic homeostasis of the body. Controlling hemostatic functions include regulating electrolytes, acid-base balance, and blood pressure. For example, the kidneys are responsible for regulating blood volume and pressure by adjusting volume of water lost in the urine and releasing erythropoietin and renin, for example. The kidneys also regulate plasma ion concentrations (e.g., sodium, potassium, chloride ions, and calcium ion levels) by controlling the quantities lost in the urine and the synthesis of calcitrol. Other hemostatic functions controlled by the kidneys include stabilizing blood pH by controlling loss of hydrogen and bicarbonate ions in the urine, conserving valuable nutrients by preventing their excretion, and assisting the liver with detoxification.

Also shown in FIG. 1 is the right suprarenal gland 11, commonly referred to as the right adrenal gland. The suprarenal gland 11 is a star-shaped endocrine gland that rests on top of the kidney 10. The primary function of the suprarenal glands (left and right) is to regulate the stress response of the body through the synthesis of corticosteroids and catecholamines, including cortisol and adrenaline (epinephrine), respectively. Encompassing the kidneys 10, suprarenal glands 11, renal vessels 12, and adjacent perirenal fat is the renal fascia, e.g., Gerota's fascia, (not shown), which is a fascial pouch derived from extraperitoneal connective tissue.

The autonomic nervous system of the body controls involuntary actions of the smooth muscles in blood vessels, the digestive system, heart, and glands. The autonomic nervous system is divided into the sympathetic nervous system and the parasympathetic nervous system. In general terms, the parasympathetic nervous system prepares the body for rest by lowering heart rate, lowering blood pressure, and stimulating digestion. The sympathetic nervous system effectuates the body's fight-or-flight response by increasing heart rate, increasing blood pressure, and increasing metabolism.

In the autonomic nervous system, fibers originating from the central nervous system and extending to the various ganglia are referred to as preganglionic fibers, while those extending from the ganglia to the effector organ are referred to as postganglionic fibers. Activation of the sympathetic nervous system is effected through the release of adrenaline (epinephrine) and to a lesser extent norepinephrine from the suprarenal glands 11. This release of adrenaline is triggered by the neurotransmitter acetylcholine released from preganglionic sympathetic nerves.

Figure 2B:
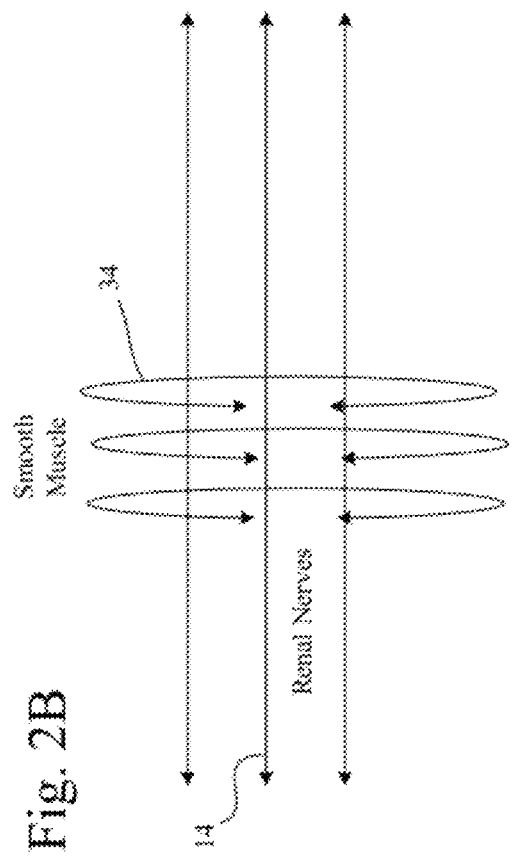

The kidneys and ureters (not shown) are innervated by the renal nerves 14. FIGS. 1 and 2A-2B illustrate sympathetic innervation of the renal vasculature, primarily innervation of the renal artery 12. The primary functions of sympathetic innervation of the renal vasculature include regulation of renal blood flow and pressure, stimulation of renin release, and direct stimulation of water and sodium ion reabsorption.

Most of the nerves innervating the renal vasculature are sympathetic postganglionic fibers arising from the superior mesenteric ganglion 26. The renal nerves 14 extend generally axially along the renal arteries 12, enter the kidneys 10 at the hilum 17, follow the branches of the renal arteries 12 within the kidney 10, and extend to individual nephrons. Other renal ganglia, such as the renal ganglia 24, superior mesenteric ganglion 26, the left and right aorticorenal ganglia 22, and celiac ganglia 28 also innervate the renal vasculature. The celiac ganglion 28 is joined by the greater thoracic splanchnic nerve (greater TSN). The aorticorenal ganglia 26 is joined by the lesser thoracic splanchnic nerve (lesser TSN) and innervates the greater part of the renal plexus.

Sympathetic signals to the kidney 10 are communicated via innervated renal vasculature that originates primarily at spinal segments T10-T12 and L1. Parasympathetic signals originate primarily at spinal segments S2-S4 and from the medulla oblongata of the lower brain. Sympathetic nerve traffic travels through the sympathetic trunk ganglia, where some may synapse, while others synapse at the aorticorenal ganglion 22 (via the lesser thoracic splanchnic nerve, i.e., lesser TSN) and the renal ganglion 24 (via the least thoracic splanchnic nerve, i.e., least TSN). The postsynaptic sympathetic signals then travel along nerves 14 of the renal artery 12 to the kidney 10. Presynaptic parasympathetic signals travel to sites near the kidney 10 before they synapse on or near the kidney 10.

With particular reference to FIG. 2A, the renal artery 12, as with most arteries and arterioles, is lined with smooth muscle 34 that controls the diameter of the renal artery lumen 13. Smooth muscle, in general, is an involuntary non-striated muscle found within the media layer of large and small arteries and veins, as well as various organs. The glomeruli of the kidneys, for example, contain a smooth muscle-like cell called the mesangial cell. Smooth muscle is fundamentally different from skeletal muscle and cardiac muscle in terms of structure, function, excitation-contraction coupling, and mechanism of contraction.

Smooth muscle cells can be stimulated to contract or relax by the autonomic nervous system, but can also react on stimuli from neighboring cells and in response to hormones and blood borne electrolytes and agents (e.g., vasodilators or vasoconstrictors). Specialized smooth muscle cells within the afferent arteriole of the juxtaglomerular apparatus of kidney 10, for example, produces renin which activates the angiotension II system.

The renal nerves 14 innervate the smooth muscle 34 of the renal artery wall 15 and extend lengthwise in a generally axial or longitudinal manner along the renal artery wall 15. The smooth muscle 34 surrounds the renal artery circumferentially, and extends lengthwise in a direction generally transverse to the longitudinal orientation of the renal nerves 14, as is depicted in FIG. 2B.

The smooth muscle 34 of the renal artery 12 is under involuntary control of the autonomic nervous system. An increase in sympathetic activity, for example, tends to contract the smooth muscle 34, which reduces the diameter of the renal artery lumen 13 and decreases blood perfusion. A decrease in sympathetic activity tends to cause the smooth muscle 34 to relax, resulting in vessel dilation and an increase in the renal artery lumen diameter and blood perfusion. Conversely, increased parasympathetic activity tends to relax the smooth muscle 34, while decreased parasympathetic activity tends to cause smooth muscle contraction.

Figure 3B:
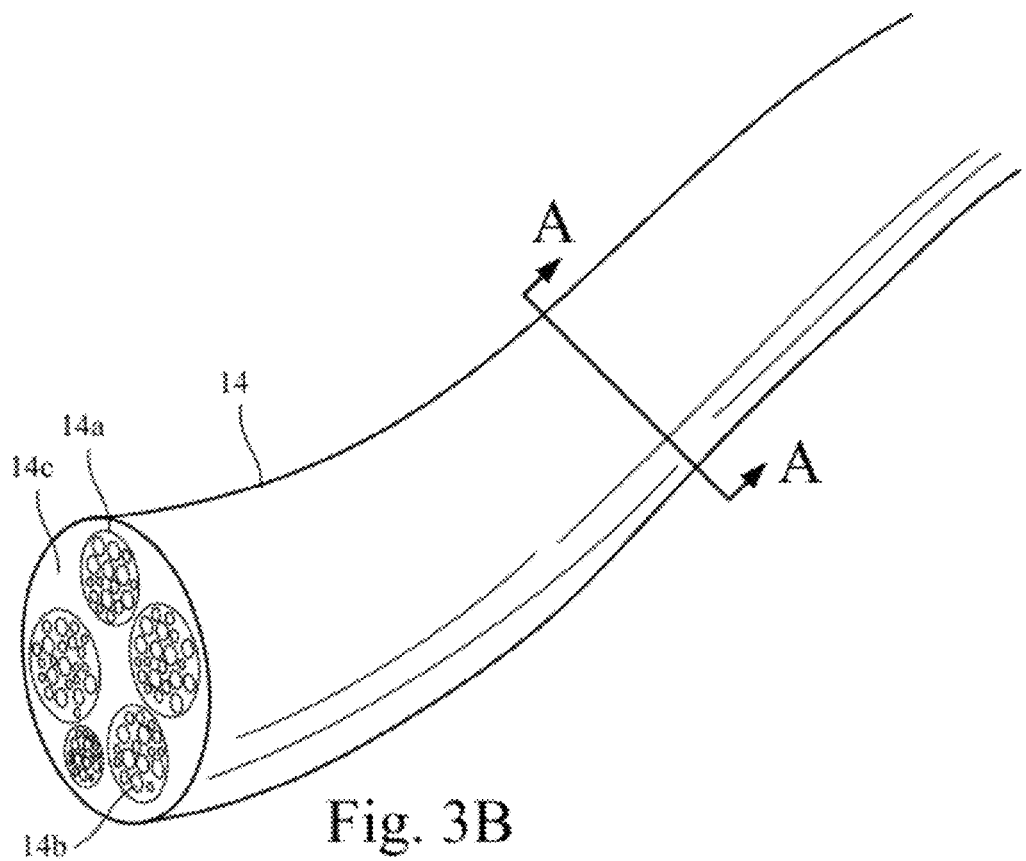
FIGS. 3B and 3C illustrate a portion of a renal nerve.

FIG. 3A shows a segment of a longitudinal cross-section through a renal artery, and illustrates various tissue layers of the wall 15 of the renal artery 12. The innermost layer of the renal artery 12 is the endothelium 30, which is the innermost layer of the intima 32 and is supported by an internal elastic membrane. The endothelium 30 is a single layer of cells that contacts the blood flowing though the vessel lumen 13. Endothelium cells are typically polygonal, oval, or fusiform, and have very distinct round or oval nuclei. Cells of the endothelium 30 are involved in several vascular functions, including control of blood pressure by way of vasoconstriction and vasodilation, blood clotting, and acting as a barrier layer between contents within the lumen 13 and surrounding tissue, such as the membrane of the intima 32 separating the intima 32 from the media 34, and the adventitia 36. The membrane or maceration of the intima 32 is a fine, transparent, colorless structure which is highly elastic, and commonly has a longitudinal corrugated pattern.

Adjacent the intima 32 is the media 33, which is the middle layer of the renal artery 12. The media is made up of smooth muscle 34 and elastic tissue. The media 33 can be readily identified by its color and by the transverse arrangement of its fibers. More particularly, the media 33 consists principally of bundles of smooth muscle fibers 34 arranged in a thin plate-like manner or lamellae and disposed circularly around the arterial wall 15. The outermost layer of the renal artery wall 15 is the adventitia 36, which is made up of connective tissue. The adventitia 36 includes fibroblast cells 38 that play an important role in wound healing.

A perivascular region 37 is shown adjacent and peripheral to the adventitia 36 of the renal artery wall 15. A renal nerve 14 is shown proximate the adventitia 36 and passing through a portion of the perivascular region 37. The renal nerve 14 is shown extending substantially longitudinally along the outer wall 15 of the renal artery 12. The main trunk of the renal nerves 14 generally lies in or on the adventitia 36 of the renal artery 12, often passing through the perivascular region 37, with certain branches coursing into the media 33 to enervate the renal artery smooth muscle 34.

Embodiments of the disclosure may be implemented to provide varying degrees of denervation therapy to innervated renal vasculature. For example, embodiments of the disclosure may provide for control of the extent and relative permanency of renal nerve impulse transmission interruption achieved by denervation therapy delivered using a treatment apparatus of the disclosure. The extent and relative permanency of renal nerve injury may be tailored to achieve a desired reduction in sympathetic nerve activity (including a partial or complete block) and to achieve a desired degree of permanency (including temporary or irreversible injury).

Figure 3C:
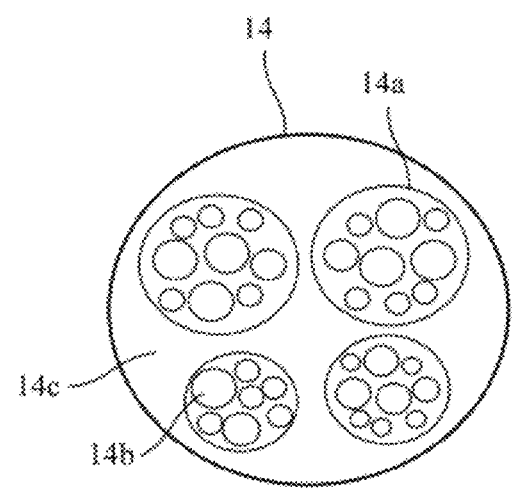

Returning to FIGS. 3B and 3C, the portion of the renal nerve 14 shown in FIGS. 3B and 3C includes bundles 14a of nerve fibers 14b each comprising axons or dendrites that originate or terminate on cell bodies or neurons located in ganglia or on the spinal cord, or in the brain. Supporting tissue structures 14c of the nerve 14 include the endoneurium (surrounding nerve axon fibers), perineurium (surrounds fiber groups to form a fascicle), and epineurium (binds fascicles into nerves), which serve to separate and support nerve fibers 14b and bundles 14a. In particular, the endoneurium, also referred to as the endoneurium tube or tubule, is a layer of delicate connective tissue that encloses the myelin sheath of a nerve fiber 14b within a fasciculus.

Major components of a neuron include the soma, which is the central part of the neuron that includes the nucleus, cellular extensions called dendrites, and axons, which are cable-like projections that carry nerve signals. The axon terminal contains synapses, which are specialized structures where neurotransmitter chemicals are released in order to communicate with target tissues. The axons of many neurons of the peripheral nervous system are sheathed in myelin, which is formed by a type of glial cell known as Schwann cells. The myelinating Schwann cells are wrapped around the axon, leaving the axolemma relatively uncovered at regularly spaced nodes, called nodes of Ranvier. Myelination of axons enables an especially rapid mode of electrical impulse propagation called saltation.

In some embodiments, a treatment apparatus of the disclosure may be implemented to deliver denervation therapy that causes transient and reversible injury to renal nerve fibers 14b. In other embodiments, a treatment apparatus of the disclosure may be implemented to deliver denervation therapy that causes more severe injury to renal nerve fibers 14b, which may be reversible if the therapy is terminated in a timely manner. In preferred embodiments, a treatment apparatus of the disclosure may be implemented to deliver denervation therapy that causes severe and irreversible injury to renal nerve fibers 14b, resulting in permanent cessation of renal sympathetic nerve activity. For example, a treatment apparatus may be implemented to deliver a denervation therapy that disrupts nerve fiber morphology to a degree sufficient to physically separate the endoneurium tube of the nerve fiber 14b, which can prevent regeneration and re-innervation processes.

By way of example, and in accordance with Seddon's classification as is known in the art, a treatment apparatus of the disclosure may be implemented to deliver a denervation therapy that interrupts conduction of nerve impulses along the renal nerve fibers 14b by imparting damage to the renal nerve fibers 14b consistent with neruapraxia. Neurapraxia describes nerve damage in which there is no disruption of the nerve fiber 14b or its sheath. In this case, there is an interruption in conduction of the nerve impulse down the nerve fiber, with recovery taking place within hours to months without true regeneration, as Wallerian degeneration does not occur. Wallerian degeneration refers to a process in which the part of the axon separated from the neuron's cell nucleus degenerates. This process is also known as anterograde degeneration. Neurapraxia is the mildest form of nerve injury that may be imparted to renal nerve fibers 14b by use of a treatment apparatus according to embodiments of the disclosure.

A treatment apparatus may be implemented to interrupt conduction of nerve impulses along the renal nerve fibers 14b by imparting damage to the renal nerve fibers consistent with axonotmesis. Axonotmesis involves loss of the relative continuity of the axon of a nerve fiber and its covering of myelin, but preservation of the connective tissue framework of the nerve fiber. In this case, the encapsulating support tissue 14c of the nerve fiber 14b is preserved. Because axonal continuity is lost, Wallerian degeneration occurs. Recovery from axonotmesis occurs only through regeneration of the axons, a process requiring time on the order of several weeks or months. Electrically, the nerve fiber 14b shows rapid and complete degeneration. Regeneration and re-innervation may occur as long as the endoneural tubes are intact.

A treatment apparatus may be implemented to interrupt conduction of nerve impulses along the renal nerve fibers 14b by imparting damage to the renal nerve fibers 14b consistent with neurotmesis. Neurotmesis, according to Seddon's classification, is the most serious nerve injury in the scheme. In this type of injury, both the nerve fiber 14b and the nerve sheath are disrupted. While partial recovery may occur, complete recovery is not possible. Neurotmesis involves loss of continuity of the axon and the encapsulating connective tissue 14c, resulting in a complete loss of autonomic function, in the case of renal nerve fibers 14b. If the nerve fiber 14b has been completely divided, axonal regeneration causes a neuroma to form in the proximal stump.

A more stratified classification of neurotmesis nerve damage may be found by reference to the Sunderland System as is known in the art. The Sunderland System defines five degrees of nerve damage, the first two of which correspond closely with neurapraxia and axonotmesis of Seddon's classification. The latter three Sunderland System classifications describe different levels of neurotmesis nerve damage.

The first and second degrees of nerve injury in the Sunderland system are analogous to Seddon's neurapraxia and axonotmesis, respectively. Third degree nerve injury, according to the Sunderland System, involves disruption of the endoneurium, with the epineurium and perineurium remaining intact. Recovery may range from poor to complete depending on the degree of intrafascicular fibrosis. A fourth degree nerve injury involves interruption of all neural and supporting elements, with the epineurium remaining intact. The nerve is usually enlarged. Fifth degree nerve injury involves complete transection of the nerve fiber 14b with loss of continuity.

Figure 4:
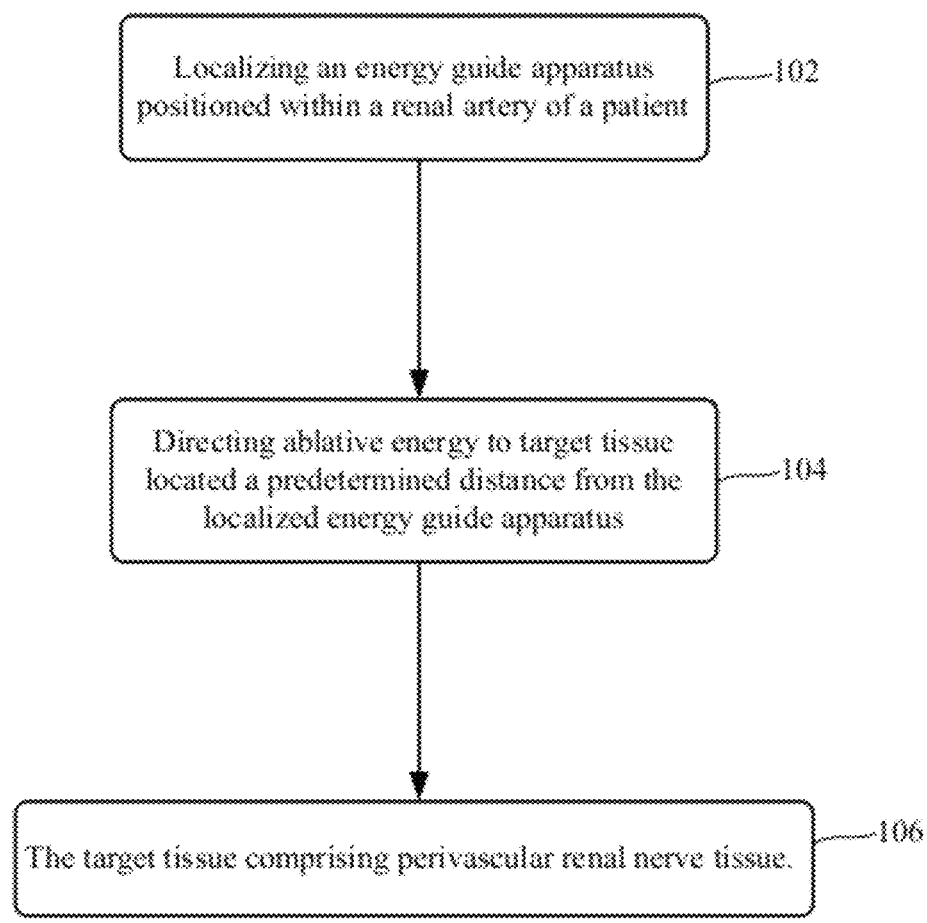
FIG. 4 is a flow chart illustrating various processes of a method for guiding externally generated ablative energy to target tissue of the body in accordance with various embodiments.

In accordance with various embodiments, and as illustrated in FIG. 4, methods of the disclosure involve localizing 102 an energy guide apparatus positioned within a renal artery of a patient. Methods of the disclosure involve directing 104 ablative energy to target tissue located a predetermined distance from the localized energy guide apparatus. The target tissue includes perivascular renal nerve tissue 106 adjacent the renal artery.

Figure 5:
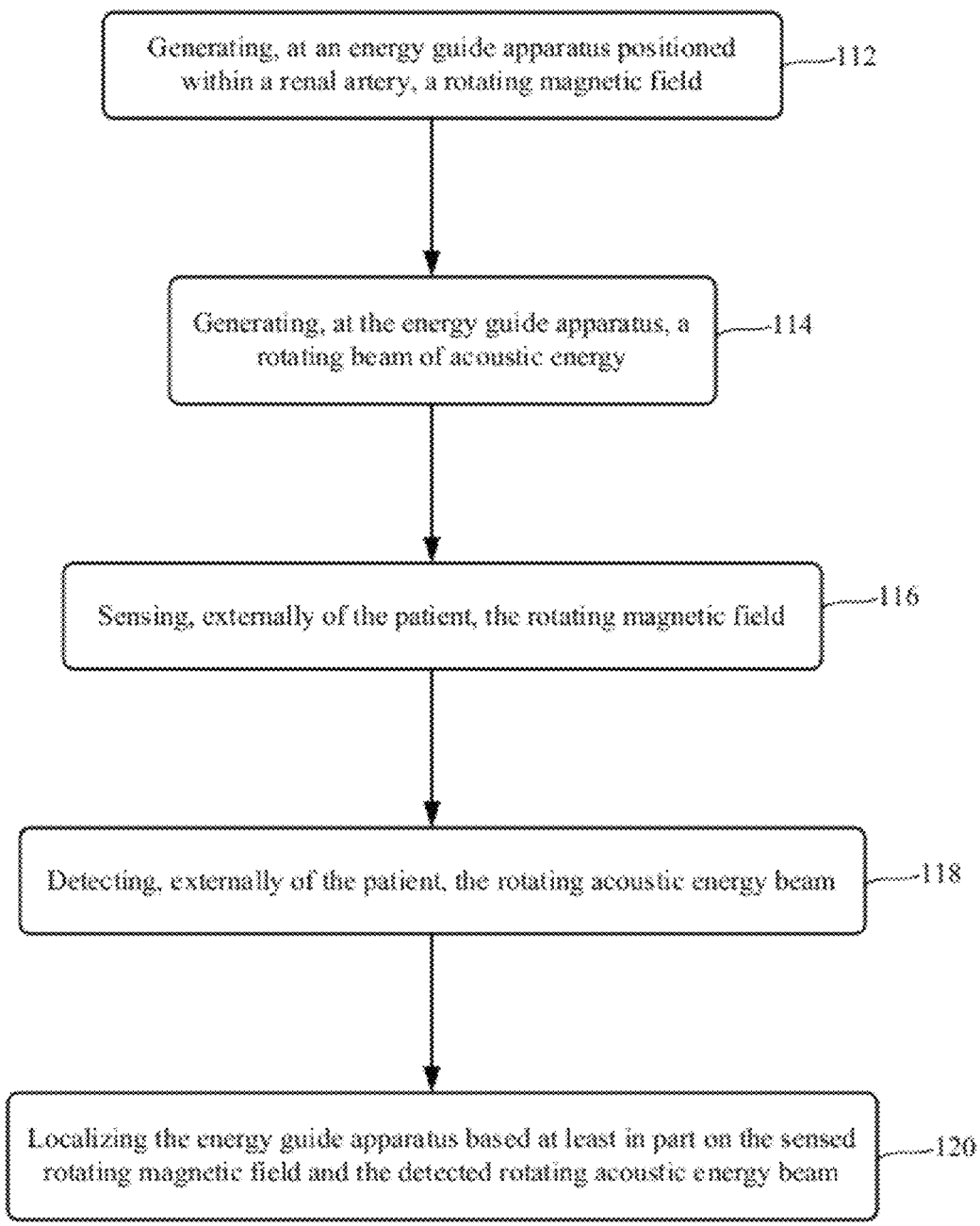
FIG. 5 is a flow chart illustrating various processes of a method for guiding externally generated ablative energy to target tissue of the body based on a rotating magnetic field and a rotating beam of acoustic energy generated from within a patient's renal artery in accordance with various embodiments.

As shown in FIG. 5, various method embodiments involve generating, at an energy guide apparatus positioned within a renal artery, a rotating magnetic field 112 and a rotating beam of acoustic energy 114. Methods also involve externally sensing 116 the rotating magnetic field and detecting 118 the rotating acoustic energy beam. Methods further involve localizing 120 the energy guide apparatus based at least in part on the sensed rotating magnetic field and the detected rotating acoustic energy beam.

Figure 6:
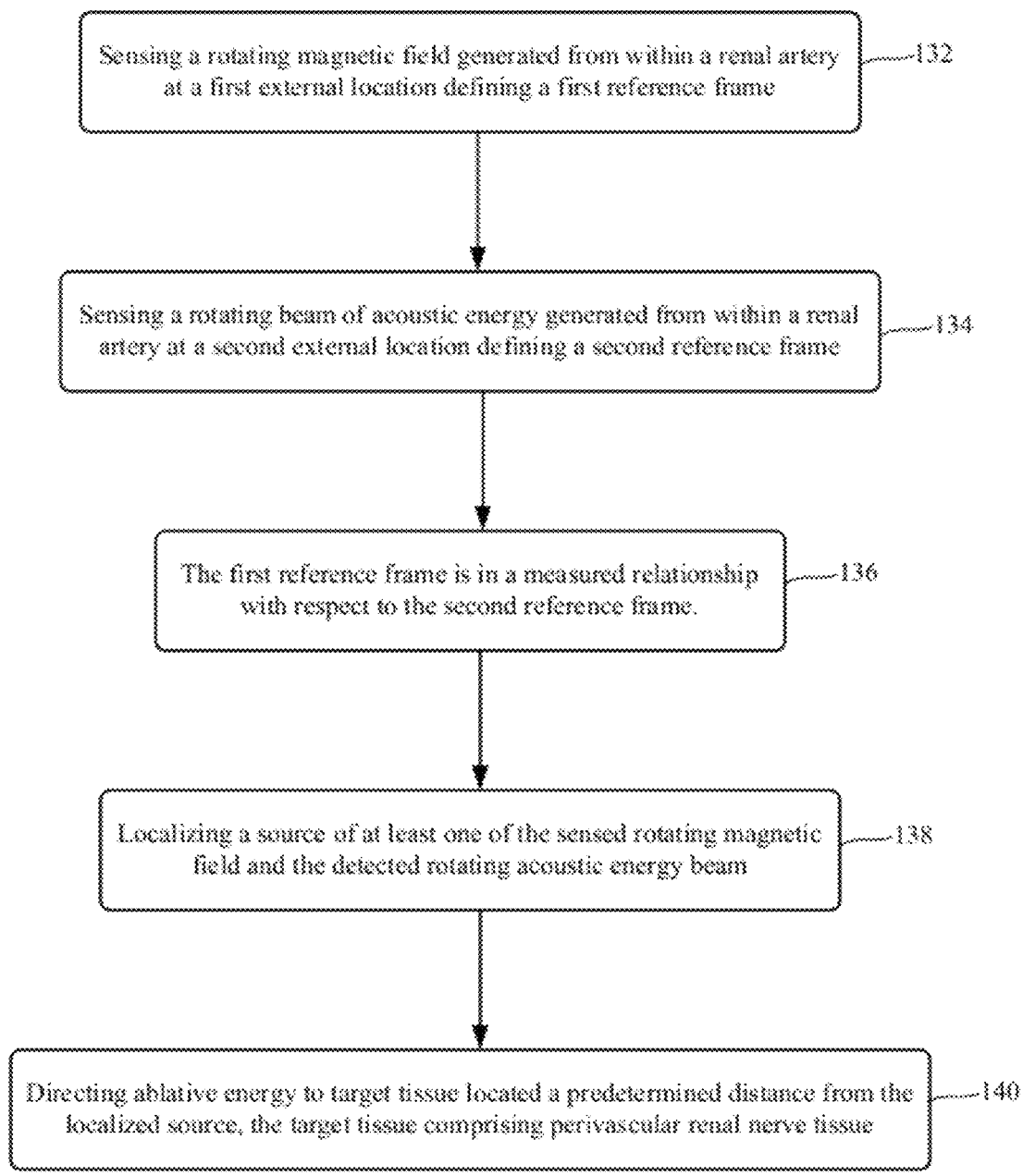
FIG. 6 is a flow chart illustrating various processes of a method for guiding externally generated ablative energy to target tissue of the body based on a rotating magnetic field and a rotating beam of acoustic energy generated from within a patient's renal artery in accordance with various embodiments.

According to other embodiments, and as illustrated in FIG. 6, methods of the disclosure involve sensing 132 a rotating magnetic field generated from within a renal artery at a first external location defining a first reference frame. Methods involve sensing 130 for a rotating beam of acoustic energy generated from within the renal artery at a second external location defining a second reference frame. The first reference frame is in a measured relationship 136 with respect to the second reference frame. Methods also involve localizing 138 a source of at least one of the sensed rotating magnetic field and the detected rotating acoustic energy beam. Methods further involve directing 140 ablative energy to target tissue located a predetermined distance from the localized source, the target tissue including perivascular renal nerve tissue.

Figure 7:
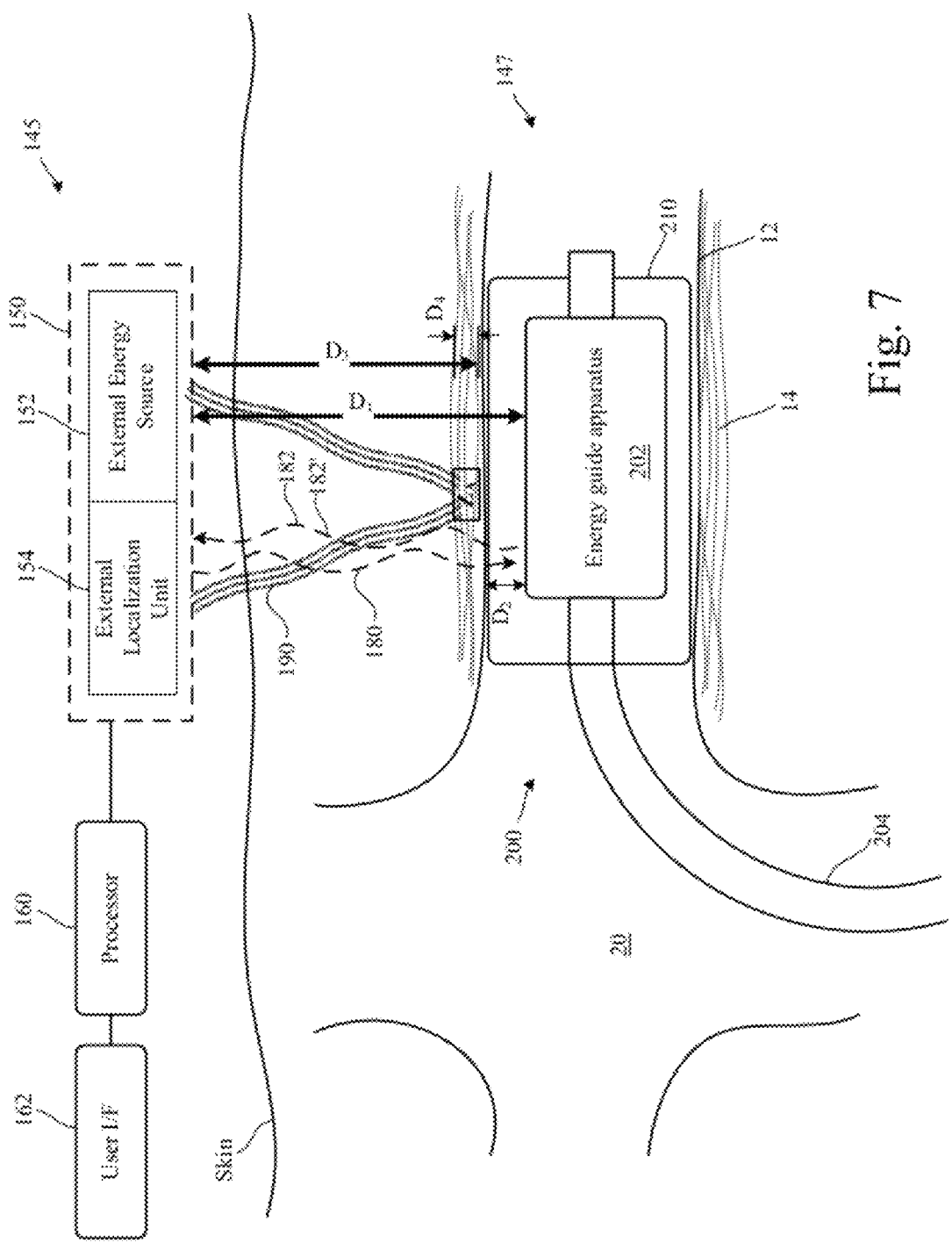
FIG. 7 illustrates an apparatus for guiding externally generated ablative energy to target tissue of the body in accordance with various embodiments.

Turning now to FIG. 7, there is illustrated and apparatus for directing externally generated ablative energy to target tissue within the body in accordance with various embodiments. The apparatus shown in FIG. 7 includes an ex vivo apparatus 145 and an in vivo apparatus 147. The in vivo apparatus 147 includes a catheter 200 which includes a flexible shaft 204 having a proximal end, a distal end, and a length sufficient to access a patient's renal artery 12 relative to a percutaneous access location. The in vivo apparatus 147 also includes an energy guide apparatus 202 provided at the distal end of the shaft 204 and dimension for deployment within the renal artery 12. A support structure 210 is preferably provided at the distal end of the shaft 204 and is transformable between a low-profile introduction configuration and a deployed configuration (e.g., a centering balloon or a centering basket). In some embodiments, the support structure 210 includes a centering basket with four struts, which allows flowing blood to cool the artery wall and the heat producing components (e.g., acoustic transducer) of the energy guide apparatus 202. The support structure 210 serves to center the energy guide apparatus 202 within the renal artery 12 when in the deployed configuration.

The ex vivo apparatus 145 includes an arrangement 150, 160 configured to localize the energy guide apparatus 202 positioned within the renal artery 12. The arrangement 150 includes an external localization unit 154 and an external energy source 152. The external energy source 152 is configured to direct ablative energy to target tissue located a predetermined distance from the localized energy guide apparatus 202 (e.g., a localized component or feature of the energy guide apparatus 202), the target tissue including perivascular renal nerve tissue.

In some embodiments, the external localization unit 154 is configured to generate localization energy 180 that propagates to the energy guide apparatus 202 through the skin and intervening body tissue. In the case of the energy guide apparatus 202 being configured as a passive apparatus, the external localization unit 154 receives a response 182 reflected from, or otherwise responsively produced by, the energy guide apparatus 202. Localization of the energy guide apparatus 202, in this scenario, is performed by the external localization unit 154 and processor 160. According to a representative embodiment employing a passive energy guide apparatus 202, the external localization unit 154 can include a CT scanner and the passive energy guide apparatus 202 may include one or more radiopaque markers.

In other embodiments, the energy guide apparatus 202 is configured as an active apparatus that generates a beacon 182 which can be detected by the external localization unit 154. The energy guide apparatus 202 may be configured to generate a beacon 182 or a multiplicity of beacons 182, 182'. In some embodiments, a single acoustic energy beacon 182 may be generated by the energy guide apparatus 202, which is received by an array of acoustic transducers provided at the external localization unit 154. The energy guide apparatus 202 may be configured to generate an acoustic energy beacon 182 and a magnetic field which also serves as an energy beacon 182'. In this scenario, the external localization unit 154 includes an array of magnetic fields sensors and an array of acoustic transducers for detecting the acoustic and magnetic field energy beacons 182 and 182', respectively. It is understood that various combinations of active and passive components can be incorporated in one or both of the ex vivo and in vivo apparatuses 145 and 147.

The external localization unit 154 cooperates with the processor 160 to determine the precise position and orientation of the energy guide apparatus 202 positioned within the renal artery 12. For purposes of simplicity of explanation, the localization of the energy guide apparatus 202 shown in FIG. 7, which typically involves determining three-dimensional Cartesian coordinates and an orientation angle, is depicted as a distance, $D_1$, between the external localization unit 154 and the energy guide apparatus 202. A distance, $D_2$, between the energy guide apparatus 202 and an inner wall surface of the renal artery 12, is measured either by the apparatus of FIG. 7 (e.g., low-intensity ultrasound imaging) or a separate procedure such as quantitative angiography of the renal artery 12. The difference between the two distances $D_1$ and $D_2$ provides a precise location of the renal artery's inner wall relative to the external localization unit 154. The difference between these two distances is offset by a small distance to avoid ablating the renal artery wall.

The offset can be selected based on the anatomy of a particular patient (e.g., by imaging a region from 0 mm to about 1 mm away from the renal artery lumen wall) or on patient population data. As discussed previously, human renal nerves are typically found lying within 3.5 mm of a renal artery lumen wall, but have been found lying as close as about 0.5 mm and as far out as about 7 mm from the renal artery lumen wall. As such, an offset of about 0.5 mm would provide a high likelihood that renal nerves closest to a renal artery will be ablated, although an offset between about 1 to 2 mm may be acceptable in many cases. A minimum safe offset is preferably one that ensures that the artery wall is not subjected to ablative energy 190 produced by the external energy source 152.

In some embodiments, an additional offset, D4, may be included to define a zone of ablation, shown as $Z_A$, which, in actuality, is a three-dimensional volume. A maximum additional offset, D4, may be based on the maximum depth (a distance from the renal artery lumen wall projecting normal from the wall into adjacent perivascular space) of the ablation zone $Z_A$, not exceeding about 7 mm from the renal artery lumen wall. Imaging perivascular space within 7 mm from the renal artery lumen wall can be useful for establishing the additional offset, D4.

The external energy source 152 directs high-intensity energy or radiation 192 to the target perivascular renal nerves 14. The external energy source 152 typically produces spot lesions, and a multiplicity of spot lesions may be produced within an ablation zone, $Z_A$. Ablation is preferably performed at points around the periphery of the renal artery 12. The external energy source 152 may need to be moved to two or more positions relative to the patient's renal artery 12 to complete a circumferential ablation. As discussed previously, the energy guide apparatus 202 may include an ultrasound transducer (alone or in conjunction with an external imaging array) that can be used to image adjacent tissue to assess the extent and location of the ablation. Images, data, and other information about the ablation procedure can be displayed on a user interface 162, which is coupled to the processor 160.

Figure 8:
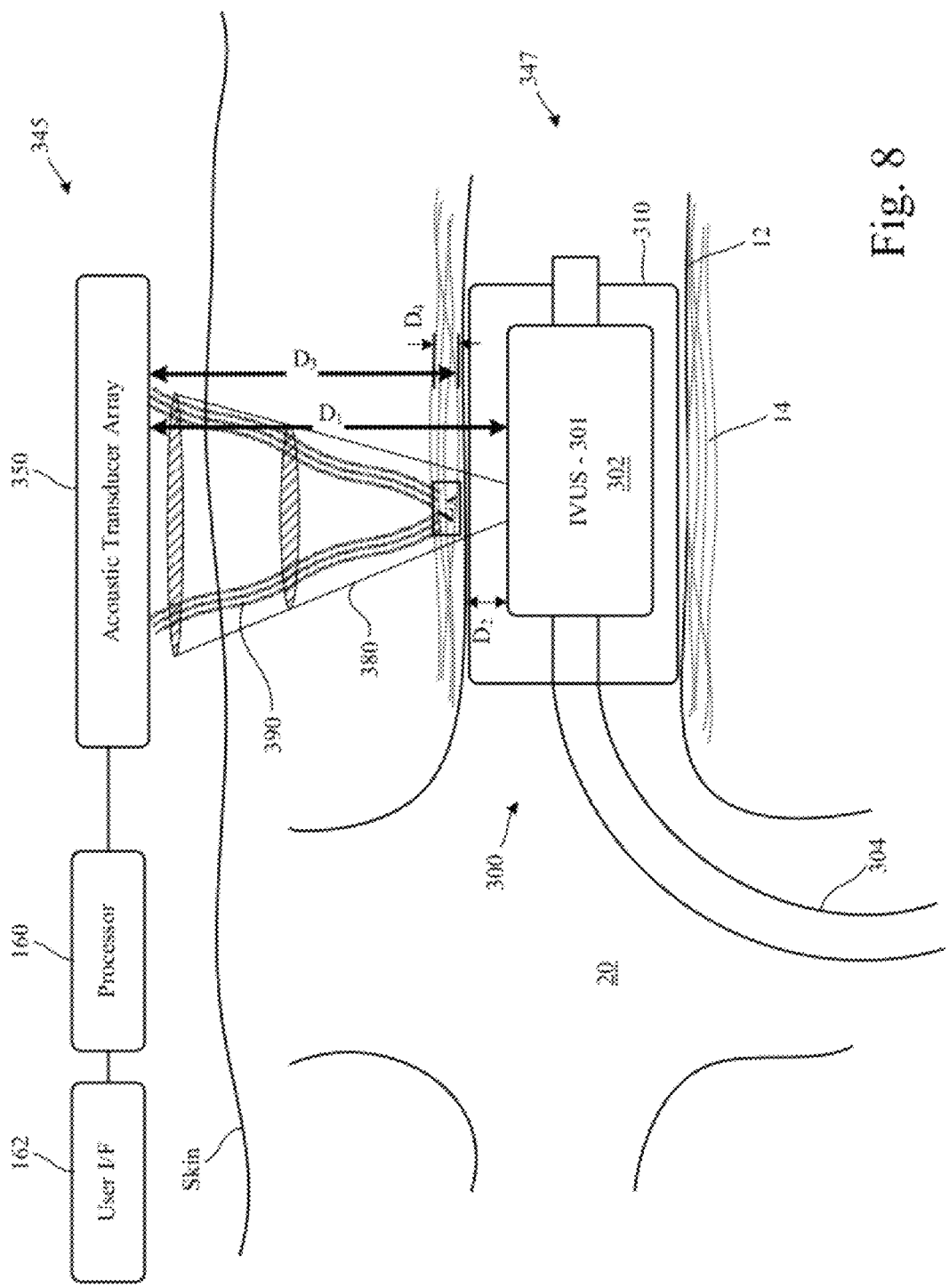
FIG. 8 illustrates an apparatus for guiding externally generated, high-intensity ablative acoustic energy to target tissue of the body in accordance with various embodiments.

FIG. 8 illustrates an apparatus for directing externally generated high-intensity acoustic energy to target tissue of the body, such as perivascular renal nerves adjacent a patient's renal artery. In the embodiment shown in FIG. 8, an in vivo apparatus 347 includes a catheter 300 comprising a flexible shaft 304 having a length sufficient to extend between a patient's renal artery 12 and a percutaneous access location. An energy guide apparatus 302 is provided at a distal end of the shaft 304. The distal end of the shaft 304 further includes a support structure 310 which is transformable between a low-profile introduction configuration and a deployed configuration. As previously discussed, the support structure 310 serves to center the energy guide apparatus 302 within the lumen of the renal artery 12.

The energy guide apparatus 302 includes an intravascular ultrasound device 301 configured to generate a rotating beam of acoustic energy. A micro-motor of the IVUS 301 causes a mirror (acoustic reflector) to rotate at a precisely known target frequency. A stationary ultrasound transducer emits ultrasound energy which is reflected by the rotating mirror in a direction perpendicular to a longitudinal axis of the IVUS housing/shaft's distal end. According to this configuration, the IVUS 301 generates a conical beam of acoustic energy that rotates at the precisely known target frequency. This rotating acoustic energy beam can be detected externally of the patient.

In the embodiment illustrated in FIG. 8, the ex vivo apparatus 345 includes an acoustic transducer array 350 which is configured to detect the rotating beam of acoustic energy emitted by the IVUS 301. The acoustic transducers of the array 350 may operate at the same frequency as that/those of the IVUS 301, allowing for identification and synchronous detection of the IVUS 301 (e.g., the rotating magnet of the IVUS 301). The processor 160 cooperates with the acoustic transducer array 350 to determine the position and orientation of the IVUS 301, and to compute the distance $D_1$, between the array 350 and the IVUS 301, and the distance $D_2$, between the inner wall of the renal artery 12 and the IVUS 301. Based on these distances, which in actuality are Cartesian coordinates and an orientation angle, the distance $D_3$ between the array 350 and target perivascular renal nerve tissue 14 is computed. As discussed previously, an offset between about 0.5 and 2 or 3 mm is included to avoid ablating the wall of the renal artery 12. An additional offset, shown as the distance $D_4$, can be included to define a region of ablation, $Z_A$. According to some embodiments, the acoustic transducer array 350 is configured to operate as an acoustic detector array for detecting the rotating beam of acoustic energy emitted by the IVUS 301. The acoustic transducer array 350 is also configured to operate as a high-intensity acoustic ablation array that directs high-intensity acoustic energy to the target tissue for ablating the target tissue.

Figure 9:
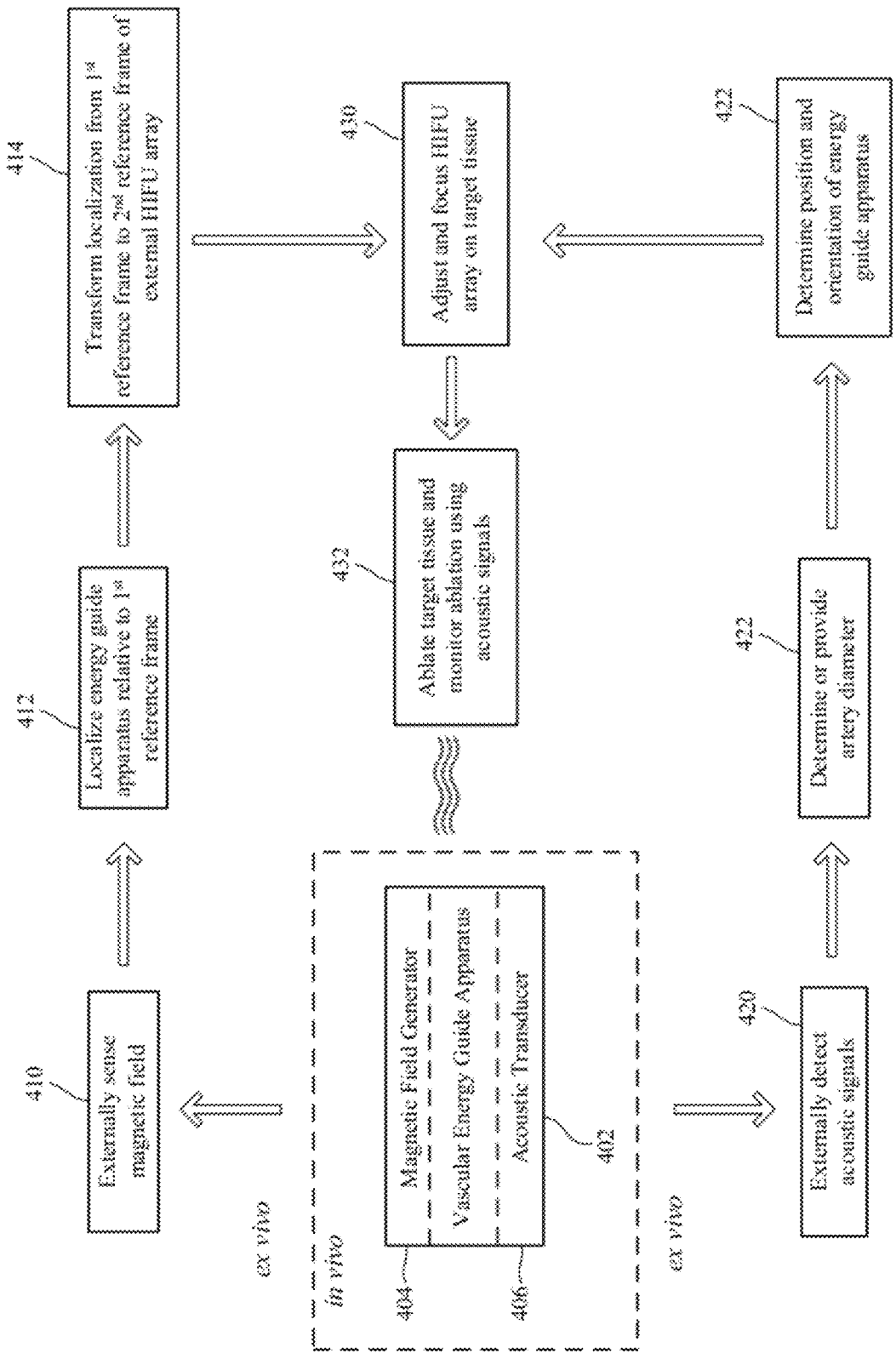
FIG. 9 illustrates an apparatus for guiding externally generated ablative energy to target tissue of the body in accordance with various embodiments.
Figure 10:
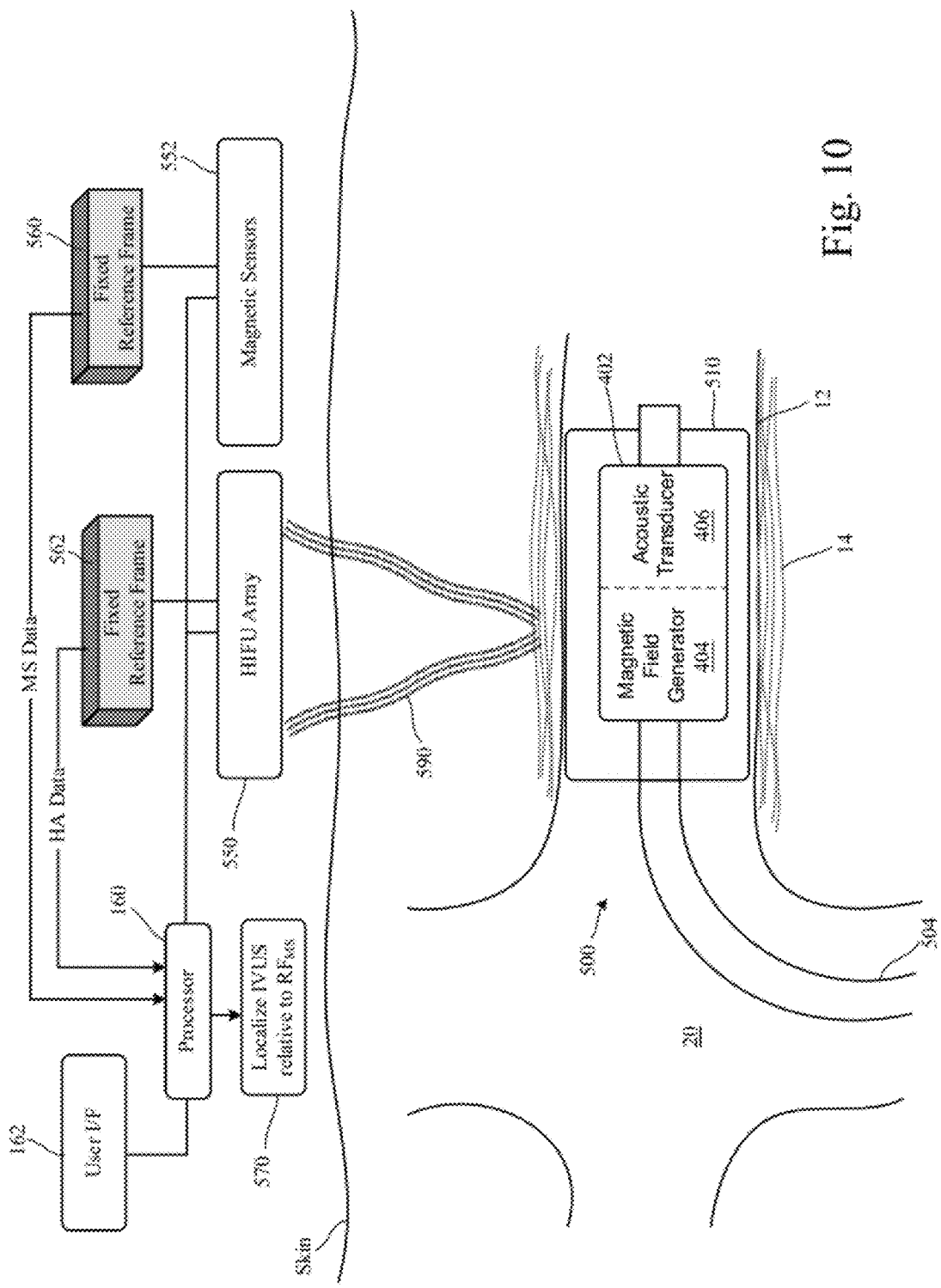
FIG. 10 illustrates an apparatus for guiding externally generated ablative ultrasound energy to target tissue of the body based on a rotating magnetic field and a rotating beam of acoustic energy generated from within a patient's renal artery in accordance with various embodiments.

Referring now to FIGS. 9 and 10, there is illustrated a flow block diagram (FIG. 9) and a system block diagram (FIG. 10) illustrating various apparatuses and processes for guiding externally generated high-intensity energy to target tissue of the body. In the embodiment shown in FIGS. 9 and 10, an energy guide apparatus 402 is provided at a distal end of the shaft 504 of a catheter 500. The energy guide apparatus 402 includes an acoustic transducer 406 and a magnetic field generator 404. The acoustic transducer 406 is preferably configured to generate a rotating beam of acoustic energy at a target frequency which can be externally detected 420, such as by an external HIFU array 550. The acoustic transducer 406 may be configured as an IVUS, such as the IVUS 700 shown in FIG. 12. The externally detected acoustic signals 420 may be used to determine the diameter of the renal artery 12. In some embodiments, optical magnetometers can be used to facilitate measuring of the renal artery's diameter. The artery diameter measurement can be used to determine a distance between the energy guide apparatus 402 and inner wall of the renal artery 12. The externally detected acoustic signals 420 may also be used to determine the position and orientation of the energy guide apparatus 402 for purposes of enhancing localization accuracy (shown as HA data communicated to the processor 160).

The magnetic field generator 404 of the energy guide apparatus 402 is configured to generate a rotating magnetic field which can be sensed externally 410, such as by an array of magnetic sensors 552 defining a first reference frame 560. Suitable magnetic sensors for the array 552 include, for example, magnetic induction (wire wound around a magnetic core) sensors, flux gate magnetometers, saturable core magnetometers, Hall effect sensors, Superconducting Quantum Interference Device ("SQUID") magnetometers, and giant magnetoresistance ("GMR") sensors. The externally sensed magnetic field 410 is communicated as magnetic sensor data (MS data) to the processor 160. The processor 160 uses the magnetic sensor data to localize 412/570 the energy guide apparatus 402 relative to the first reference frame 560. The processor 160 may also use localization data produced by the HIFU array 550 in response to detecting the rotating beam of acoustic energy produced by the acoustic transducer 406 to enhance the accuracy of localization measurements as discussed previously.

The external HIFU array 550 is configured to produce high-intensity ultrasound energy that can be focused at target tissue of the body. In order to positionally synchronize the first reference frame 560 of the magnetic sensor array 552 with a second reference frame 562 of the HIFU array 550, one approach involves transforming the Cartesian coordinates and orientation angle of the energy guide apparatus localized with respect to the first reference frame to corresponding Cartesian coordinates and orientation angle of the second reference frame. Using the transformed localization of the energy guide apparatus 412, 414 and (optionally) the position and orientation of the energy guide apparatus determined 422 using the detected acoustic signals, the external HIFU array 550 is adjusted to focus high-intensity ultrasound energy at the target tissue. The target tissue is ablated, and the ablated tissue and surrounding tissue may be monitored using the acoustic signals 432 generated by the acoustic transducer 406 and/or the HIFU array 562 operating in a low-intensity imaging mode.

According to other embodiments, and with continued reference to FIG. 9, the energy guide apparatus 402 can be positioned and operated at a location outside of the renal artery, such as from within a nearby organ or other anatomical structure. Various organs and structures of the body near the renal arteries can be suitable sites for guiding externally generated ablative energy to perivascular renal nerves. Suitable organs and structures include the patient's renal colon (e.g., transverse colon) and a renal vein or other blood vessel in proximity to the renal artery, such as the hepatic portal vein. Access to such alternative sites within the body may be gained preferably via a minimally-invasive body pathway beginning at a natural orifice (e.g., mouth, anus, urethra). For some patients, a more invasive percutaneous access procedure may be required. Additional details concerning embodiments that involve positioning and operating an energy guide apparatus from a location outside of the renal arteries are provided toward the end of the detailed description.

Figure 11:
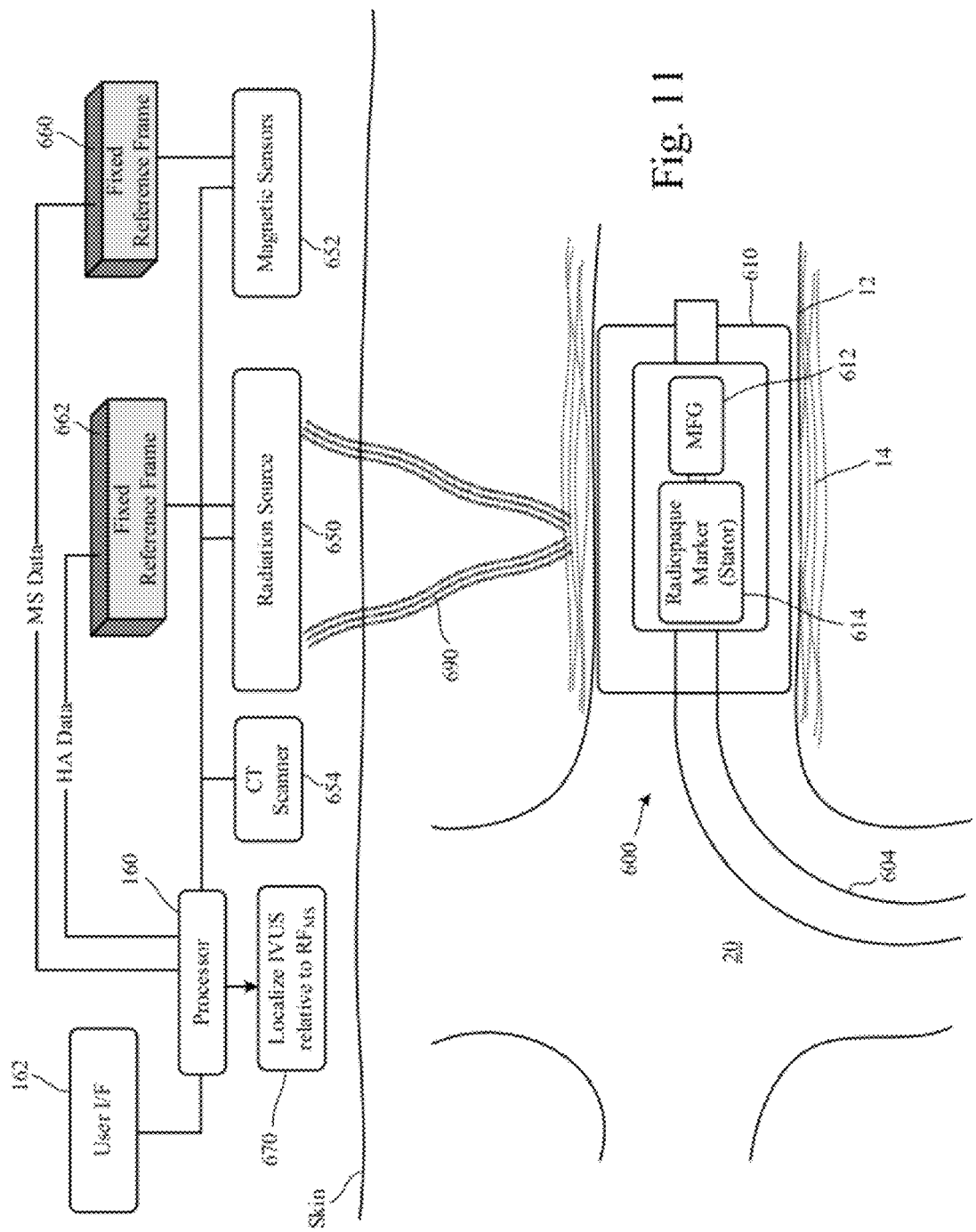
FIG. 11 illustrates an apparatus for guiding externally generated ablative radiation to target tissue of the body based on a rotating magnetic field generated from within a patient's renal artery and a radiopaque marker positioned within the patient's renal artery in accordance with various embodiments.

In the embodiment illustrated in FIG. 11, the external energy source is preferably a radiation source 650, such as an x-ray radiation source or a gamma-ray radiation source. According to the embodiment shown in FIG. 11, the energy guide apparatus 602 includes a magnetic field generator (MFG) 612 configured to generate a rotating magnetic field and at least one radiopaque marker 614. In this embodiment, the MFG 612 need not be a component of an IVUS, but may instead be a stand-alone device. In other embodiments, the MFG 612 can be a component of an IVUS. The radiopaque marker 614 is preferably situated on a component structure that is not rotating, and is readily detectable by an external CT scanner 654. For example, the MFG 612 may include a Pt—Ir stator.

According to some embodiments, the CT scanner 654 is used to localize the energy guide apparatus 602. In other embodiments, the rotating magnetic field sensed by the array of magnetic sensors 652 is used to provide real-time localization of the energy guide apparatus 602, in addition to localization provided by the scan produced by the CT scanner 654. The CT scan may be displayed on the user interface 162 and co-registered with the reference frame 660 of the magnetic localization system 652 and the reference frame 662 of the external radiation source 650. Upon completion of energy guide apparatus localization, radiation is emitted from the radiation source 650 and directed to the computed target tissue. The radiation may be emitted from multiple angles with beams that converge on the target site of the ablation (e.g., perivascular renal nerves 14).

Figure 12:
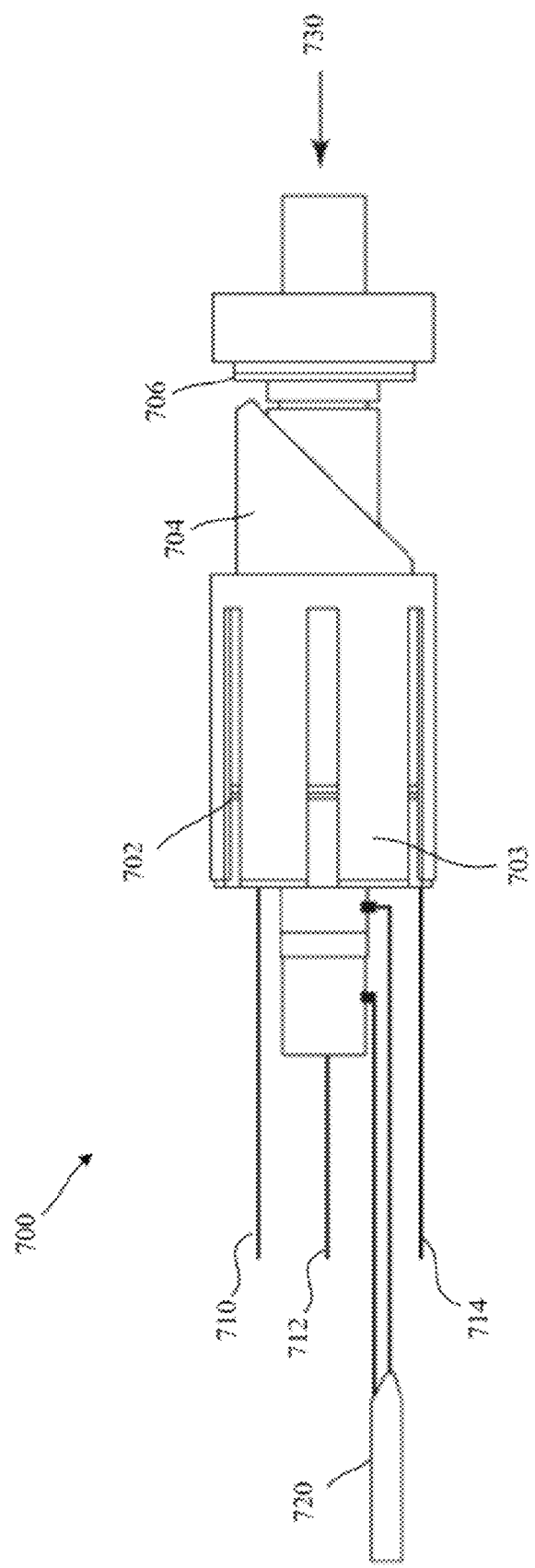
FIG. 12 illustrates an intravascular ultrasound device useful in an apparatus for guiding externally generated ablative energy to target tissue of the body.

FIG. 12 illustrates an embodiment of an IVUS 700 in accordance with various embodiments. The IVUS 700 shown in FIG. 12 is well-suited for incorporation in energy guide apparatuses according to previously described embodiments. FIG. 12 illustrates a micro-motor driven IVUS imaging core. A micro-motor 702 comprises a slotted tube stator 703 into which three phase current, for example, is injected to create a rotating magnetic field within the stator 703. The rotating magnetic field rotates a magnet and an attached mirror 704 to reflect a beam of ultrasound energy from the transducer 706 into tissue in the plane perpendicular to the longitudinal axis of the device 700.

The magnet of the IVUS 700 is driven to rotate at a precisely known target frequency by a magnetic field generated by, for example, the stator windings (e.g., air core) of the slotted tube stator 703. According to some embodiments, while the externally sensed magnetic field is a combination of those created by the stator windings and the rotating magnet, the magnetic field of the rotating magnet is orders of magnitude larger than the magnetic field of the stator windings. The magnetic field rotates at the precisely known frequency of the stator drive currents supplied to current lines 710, 712, and 714. The current lines extend along the length of a flexible shaft that supports the IVUS 700 to a proximal connection interface.

The ultrasound transducer 706 can include one or more ultrasound transducer elements. The ultrasound transducer 706 is positioned to remain stationary relative to a rotatably mounted mirror 704, which serves as an acoustic reflector. Rotation of the magnet of the micro-motor 702 causes corresponding rotation of the mirror 704 at the target frequency. The ultrasound transducer 706 includes coaxial cable 720 that extends along the length of the IVUS catheter shaft. As previously discussed, the stationary ultrasound transducer 704 emits ultrasound energy which is reflected by the rotating mirror 704 in a direction perpendicular to a longitudinal axis of the IVUS device.

According to the configuration shown in FIG. 12, the IVUS 700 generates a conical beam of acoustic energy that rotates at the target frequency. This rotating acoustic energy beam can be detected externally of the patient. Additionally, the micromotor components generate a magnetic field which can be externally detected as a magnetic field that rotates at the precisely known frequency of the stator drive currents. In some embodiments, one of the rotating acoustic energy beam and the rotating magnetic field is used by an ex vivo apparatus to localize the IVUS 700 (e.g., the rotating magnet of the micro-motor 702. In other embodiments, both the rotating acoustic energy beam and the rotating magnetic field are used for IVUS localization. According to some embodiments, the IVUS 700 includes a guidewire lumen 730 dimensioned to receive a guidewire to facilitate navigation and deployment of the IVUS 700 in the renal artery. For renal denervation, a centering balloon may cover the imaging core and be inflated to center the imaging core within the renal artery.

A spinning magnet generates a rotating magnetic field at points in the space surrounding the magnet. The strength of the magnetic field may be approximately half of the magnet's magnetization at the surface of the magnet, and decreases with the cube of the distance from the spinning magnet. In at least some embodiments, the external localization system includes an array of magnetic sensors positioned outside the patient that synchronously detects the magnetic field created by the magnet as the magnet rotates. In some embodiments, the currents driving the rotating magnet may be used as a reference to provide high resolution measurements. There are many ways to sense a magnetic field. A coil of wire can sense AC magnetic fields. The sensitivity, or signal-to-noise ratio, of the induction coil increases with the coil volume. Thus, large coils can be more sensitive than relatively smaller coils. If compact, small-volume sensors are desired for a given application, then modem sensors, such as GMR sensors, may increase sensitivity.

The magnetic gradient tensor is measured and inverted using a known algorithm to produce the Cartesian coordinates and orientation of the rotating magnet. According to various representative examples, calculations using commercially available magnetic field sensors show that a location of a magnet may be localized to sub-millimeter accuracy when the rotating magnet has an 0.8 mm diameter and a 5 mm length and an array of magnetic sensors is located up to 0.5 meters from the rotating magnet. The accuracy may be improved using many different techniques including, for example, increasing the size of the rotating magnet, increasing the saturation magnetization of the magnet material, increasing the speed of the rotation of the magnet, increasing the interval over which data are averaged (i.e., reducing the sampling rate), increasing the volume of the sensors, increasing the sensitivity of the sensors, reducing the distance between the rotating magnet and the sensor array, increasing the number of magnetic sensors, improving the relative locations of the sensors in the sensor array, sensing the angular position of the magnet as it rotates and providing this data as a reference for a lock in amplifier whose input is a magnetic field sensor, or the like or combinations thereof.

Many sensor arrays are possible, in addition to a tensor array. A minimum of five independent magnetic field measurements are needed to find the three Cartesian coordinates and two orientation angles of the rotor magnet. More redundant sensor outputs may be combined to improve the measurement accuracy. There are many mathematical approaches to inversion of an array of sensor data. One simplification is to note that during one revolution of the rotor (e.g., $1/500$ sec at 500 Hz), the position of the distal end of a catheter upon which a rotating magnet is disposed cannot change appreciably. If many magnetic field data samples are collected in a revolution, the assumption that the Cartesian coordinates are the same for all of these samples, simplifies and linearizes the solution for the components of the magnetic moment vector (orientation angles). This data may be combined to solve for the vector that is perpendicular to all of the moment vectors, namely the vector defining a longitudinal axis of the catheter.

Selected features and functionality of an IVUS suitable for incorporation in energy guide apparatuses and in external localization systems and methods described herein are described in commonly owned, co-pending U.S. patent application Ser. Nos. 13/225,962 filed Sep. 6, 2011; and U.S. Patent Publication Nos. 20100249604; 20110071400; 20110071401; and 20110144479, each of which is incorporated herein by reference in its respective entirety.

The embodiments disclosed herein are generally described in the context of an energy guide apparatus positioned within a lumen of the renal artery. Alternative embodiments are directed to an energy guide apparatus that can be positioned and operated at a location outside of the renal artery, such as from within a nearby organ or other anatomical structure, as previously discussed. For example, an energy guide apparatus can be positioned within the transverse colon at a first location near the left renal artery to guide externally generated ablative energy to perivascular renal nerves proximate the left renal artery. The energy guide apparatus can be repositioned to a second location within the transverse colon near the right renal artery to guide externally generated ablative energy to perivascular renal nerves proximate the right renal artery. The transverse colon can be as close as about 4 mm from the wall of the renal arteries.

According to a minimally-invasive delivery approach, a catheter supporting an energy guide apparatus can be advanced through the mouth and along an upper gastrointestinal access path to a location proximate the renal arteries. In this delivery scenario, the catheter is advanced through the patient's esophagus, stomach, duodenum, small intestine (jejunum and ileum), ascending colon of the large intestine, and to a proximal location (relative to the direction of catheter advancement) within the transverse colon.

The energy guide apparatus is preferably positioned and/or oriented relative to the patient's left renal artery in a manner best suited for guiding externally generated ablative energy to innervated tissue of the left renal artery. After completion of the ablation (and imaging, if desired) procedure for the left renal artery, the catheter is advanced through the transverse colon to a distal location (relative to the direction of catheter advancement) in proximity to the patient's right renal artery. The energy guide apparatus is preferably positioned and/or oriented relative to the patient's right renal artery in a manner best suited for guiding externally generated ablative energy to innervated tissue of the right renal artery. In an alternative delivery approach, the catheter can be advanced through the rectum, into the descending colon of the large intestine, and to appropriate locations within the transverse colon. It is noted that anatomical variations between patient's may require positioning of the energy guide apparatus at locations of the large intestine other than within the transverse colon, such as at or near a distal portion of the ascending colon or proximal portion of the descending colon, for example.

Other organs and structures of the body near the renal arteries can be appropriate sites for guiding externally generated ablative energy to perivascular renal nerves. Suitable organs and structures include the patient's renal vein or other blood vessel in proximity to the renal artery, such as the hepatic portal vein. In some embodiments, renal nerve access can be achieved using a trans-hepatic route via the inferior vena cava and hepatic vein, similar to a TIPS procedure. In various embodiments, renal nerve access can be achieved using a body pathway that includes the inferior vena cava, hepatic vein, liver, and intraperitoneum. Other renal artery access approaches are contemplated, including those disclosed in commonly owned, co-pending U.S. patent application Ser. No. 13/243,134 filed Sep. 23, 2011, which is incorporated herein by reference.

The embodiments disclosed herein are generally described in the context of ablation of perivascular renal nerves for control of hypertension. It is understood, however, that embodiments of the disclosure have applicability in other contexts, such as performing ablation from within other vessels of the body, including other arteries, veins, and vasculature (e.g., cardiac and urinary vasculature and vessels), and other tissues of the body, including various organs.

What is claimed is:

1. An apparatus, comprising:
   an in vivo apparatus comprising:
      a flexible shaft having a proximal end a distal end; and
      an energy guide apparatus provided at the distal end of the shaft and configured to generate a rotating energy beacon including a rotating magnetic field and a rotating beam of acoustic energy;
   an ex vivo apparatus comprising:
      a localizing arrangement configured to localize the energy guide apparatus within a renal artery, wherein the localizing arrangement is configured to:
      sense the rotating magnetic field;
      detect the rotating beam of acoustic energy; and
      localize the energy guide apparatus using at least the sensed rotating magnetic field and the detected rotating beam of acoustic energy; and
      an energy source configured to direct ablative energy to a position that is adjacent to and offset from the localized energy guide apparatus;
   wherein the localizing arrangement comprises an array of ultrasound transducers configured to receive the rotating beam of acoustic energy and operable in a low-intensity imaging mode to generate an image of the energy guide apparatus; and
   wherein the localizing arrangement is configured to localize the energy guide apparatus within the renal artery using at least the generated image.

* * * * *